(12) United States Patent
Sun et al.

(10) Patent No.: US 11,158,814 B2
(45) Date of Patent: Oct. 26, 2021

(54) 9,10-DIHYDRO-ACRIDINE DERIVATIVE, AND PREPARATION METHOD AND USE THEREOF

(71) Applicant: Ningbo Lumilan Advanced Materials., Ltd., Ningbo (CN)

(72) Inventors: Hua Sun, Ningbo (CN); Wenming Zhu, Ningbo (CN); Kunshan Xie, Ningbo (CN); Zhi Kuan Chen, Ningbo (CN)

(73) Assignee: NINGBO LUMILAN ADVANCED MATERIALS CO., LTD, Ningbo (CN)

( * ) Notice: Subject to any disclaimer, the term of this patent is extended or adjusted under 35 U.S.C. 154(b) by 0 days.

(21) Appl. No.: 16/261,885

(22) Filed: Jan. 30, 2019

(65) Prior Publication Data

US 2020/0091437 A1     Mar. 19, 2020

(30) Foreign Application Priority Data

Sep. 17, 2018   (CN) .......................... 201811084418.X

(51) Int. Cl.
| | |
|---|---|
| *C07D 403/04* | (2006.01) |
| *H01L 51/00* | (2006.01) |
| *C07D 219/02* | (2006.01) |
| *C07D 219/14* | (2006.01) |
| *C07D 401/04* | (2006.01) |
| *C07D 401/14* | (2006.01) |
| *C07D 405/10* | (2006.01) |
| *C07D 405/14* | (2006.01) |
| *C07D 409/10* | (2006.01) |
| *C07D 409/14* | (2006.01) |
| *H01L 51/50* | (2006.01) |

(52) U.S. Cl.
CPC ........ *H01L 51/0072* (2013.01); *C07D 219/02* (2013.01); *C07D 219/14* (2013.01); *C07D 401/04* (2013.01); *C07D 401/14* (2013.01); *C07D 405/10* (2013.01); *C07D 405/14* (2013.01); *C07D 409/10* (2013.01); *C07D 409/14* (2013.01); *H01L 51/006* (2013.01); *H01L 51/0061* (2013.01); *H01L 51/0073* (2013.01); *H01L 51/0074* (2013.01); *H01L 51/0085* (2013.01); *H01L 51/5016* (2013.01); *H01L 51/5056* (2013.01); *H01L 51/5096* (2013.01)

(58) Field of Classification Search
CPC .................................................... C07D 403/04
See application file for complete search history.

(56) References Cited

U.S. PATENT DOCUMENTS

| | | | | |
|---|---|---|---|---|
| 8,384,068 B2 * | 2/2013 | Kahle | ................ | H01L 51/0061 257/40 |
| 2010/0219406 A1 | 9/2010 | Kahle et al. | | |
| 2015/0060803 A1 | 3/2015 | Yokoyama et al. | | |
| 2018/0138429 A1 | 5/2018 | Fuchiwaki | | |
| 2018/0155617 A1 | 6/2018 | Nakano et al. | | |
| 2018/0201632 A1 | 7/2018 | Fuchiwaki | | |
| 2018/0237460 A1 | 8/2018 | Ahn et al. | | |

FOREIGN PATENT DOCUMENTS

| | | |
|---|---|---|
| CN | 103864789 A | 6/2014 |
| CN | 104203920 A | 12/2014 |
| CN | 107986975 A | 5/2018 |
| CN | 108516959 A | 9/2018 |
| CN | 108586430 A | 9/2018 |
| CN | 108658941 A | 10/2018 |
| EP | 2182040 A2 | 5/2010 |
| KR | 20110114230 A | 10/2011 |

(Continued)

OTHER PUBLICATIONS

American Chemical Society. Chemical Abstract Service. RN 1531619-50-7. First entered into STN/firstdate of public availability: Jan. 27, 2014 (Year: 2014).*
Pope et al., Electroluminescence in Organic Crystals, The Journal of Chemical Physics 38, pp. 2042 (1963).
Tang et al., Organic Electroluminescent Diodes, Appl. Phys. Lett. 51, pp. 913-915 (Sep. 21, 1987).
Lee et al., Effect of hole transporting materials in phosphorescent white polymer light-emitting diodes, Organic Electronics 11, pp. 427-433 (2010).
Fang, et al., Improved efficiency by a fluorescent dye in red organic light-emitting devices based on a europium complex, Chemical Physics Letters 392, pp. 11-16 (2004).

(Continued)

*Primary Examiner* — John S Kenyon
(74) *Attorney, Agent, or Firm* — Miles & Stockbridge P.C.; Ajay Jagtiani

(57) ABSTRACT

The present invention discloses a 9,10-dihydro-acridine derivative having a structure of Formula (I). The compound has a suitable HOMO energy level that matches that of an anode and light emitting layer when used as a material of a hole transport layer, thus reducing the potential barrier needed to overcome when holes are transported to the light emitting layer, and reducing the operating voltage of the device. Moreover, the 9,10-dihydro-acridine derivative has high triplet energy level and LUMO level, to avoid the returning of energy from the light emitting layer, retain the electrons in the light emitting layer, increase the probability of recombination of electrons and holes in the light emitting layer, and enhance the luminescence efficiency of the device. The compound of Formula (I) has high glass transition temperature, good film forming performance, and high thermal stability. The present invention further discloses an organic light-emitting device having at least one functional layer containing the 9,10-dihydro-acridine derivative. When the compound is used as a material of the hole transport layer, a light-emitting device of high luminescence efficiency and low driving voltage is obtained.

10 Claims, 2 Drawing Sheets

(56) References Cited

FOREIGN PATENT DOCUMENTS

KR   201200221215 A   3/2012
KR   20130142967 A   12/2013

OTHER PUBLICATIONS

Shirota, et al., Charge Carrier Transporting Molecular Materials and Their Applications in Devices, Chem. Rev. 2007, vol. 107, pp. 953-1010.
Goushi, et al., Triplet exciton confinement and unconfinement by adjacent hole-transport layers, Journal of Applied Physics, vol. 95, No. 12, pp. 7798-7802 (Jun. 15, 2004).
Notification of First Office Action from counterpart Chinese Patent Application No. 201811084418.X, dated Jan. 20, 2020.
Ya-Kun Wang, et al., "A facile way to synthesize high-triplet-energy hosts for blue phosphorescent organic light-emitting diodes with high glass transition temperature and low driving voltage", Dyes and Pigments, 122 (2015) pp. 6-12.
Xiang-Yang Liu, et al., "A new synthesis strategy for acridine derivatives to constructing novel host for phosphorescent organic light-emitting diodes", Dyes and Pigments, 126 (2016) pp. 131-137.
Mounggon Kim, et al., "Improved power efficiency in deep blue phosphorescent organic light-emitting diodes using an acridine core based hole transport material", Organic Electronics 13 (2012) pp. 12-45-1249.
International Search Report and Written Opinion based on PCT/CN2018/113121 dated Jun. 17, 2019.
Second Office Action of Chinese Application No. 201811084418.X, issued in corresponding application dated Aug. 10, 2020.

* cited by examiner

9,10-DIHYDRO-ACRIDINE DERIVATIVE, AND PREPARATION METHOD AND USE THEREOF

CROSS-REFERENCE TO RELATED APPLICATION

This application claims the priority to Chinese Patent Application No. 201811084418.X filed on Sep. 17, 2018 with the State Intellectual Property Office of the People's Republic of China, and entitled "9,10-dihydro-acridine derivative and preparation method and use thereof", which is incorporated herein by reference in its entirety.

TECHNICAL FIELD

The present invention relates to the field of display technologies, and particularly to a 9,10-dihydro-acridine derivative, and a preparation method and use thereof.

RELATED ART

Organic light-emitting diodes (OLEDs) have broad application prospects in the field of display and illumination due to the advantages of self-lighting, high contrast, ultrathin thickness, light weight, low power consumption, wide viewing angle, rich color, and fast response time, thus receiving more and more attention.

OLEDs are ambipolar carrier injection-type light-emitting devices. The light-emission mechanism is as follows. Driven by an external electric field, electrons and holes are injected into an organic light-emitting layer respectively from a cathode and an anode, and recombined to form excitons in the organic light-emitting layer, and then the excitons go back to the ground state by radiation transition and emit light. In the 1960s, Pope et al. initially discovered the electroluminescence properties of organic crystalline anthracene as a luminescent material. However, the device having a light-emitting layer of this material has a high driving voltage (400 V), a low brightness, an efficiency and lifetime of the device that are not as good as those of existing devices made of inorganic materials, so organic electroluminescence does not attract much attention.

Until 1987, 8-hydroxyquinoline capable of transporting electrons was initially used as a luminescent material and the device structure was optimized by C. W. Tang (Deng Qingyun) and S. A. VanSlyke from Kodak Company (US) by using an arylamine derivative as a hole transport layer. As such, the hole injection efficiency is greatly improved, a high brightness and luminescence efficiency are achieved, and the driving voltage is reduced to below 10 V, thus breaking through the bottleneck in research of the organic light-emitting device and becoming a milestone in its development history.

The introduction of a functional layer such as the hole transport layer optimizes the structure of the OLED device, improves the efficiency of carrier transport to the light emitting layer, and promotes the formation of excitons by carriers in a desirable recombination region, thereby improving the luminescence efficiency of the OLED device. Triarylamine materials are currently widely used materials for hole transport layer, among which triphenylamines and carbazoles are the most widely used. N,N'-diphenyl-N,N'-(3-methylphenyl)-1,1'-biphenyl-4,4'-diamine (TPD), and N,N'-diphenyl-N, N'-(1-naphthyl)-1,1'-biphenyl-4,4'-diamine (NPB) are two common triarylamine materials. The structure of triarylamine makes TPD and NPB have good hole transport performance. However, the glass transition temperature of TPD is around 60° C., and the glass transition temperature of NPB is also less than 100° C. The TPD and NPB molecules tend to be arranged closely to cause crystallization, thus having no good amorphous film forming ability and heat stability. On the other hand, the increase in molecular weight of the hole transport material can improve the thermal stability of the material, but reduce the triplet energy level of the material, and aggravate the returning of energy from the light emitting layer to the hole transport layer at the same time, thus affecting the luminescence efficiency and service life of the device.

SUMMARY

Therefore, the technical problem to be solved by the present invention is that the hole transport material in the prior art has a low glass transition temperature, poor thermal stability, and cannot have both good thermal stability and high triplet energy level.

To this end, the present invention provides the following technical solutions.

The present invention provides a 9,10-dihydro-acridine derivative having a structure of Formula (I):

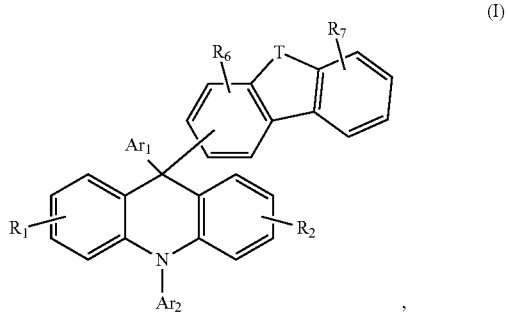

wherein T is selected from O, S, $C(R_3)(R_4)$ or $N(R_5)$;

$R_1$-$R_5$ are each independently selected from hydrogen, deuterium, halo, cyano, a C1-C30 substituted or unsubstituted alkyl group, a C2-C30 substituted or unsubstituted alkenyl group, a C2-C30 substituted or unsubstituted alkynyl group, a C3-C30 substituted or unsubstituted cycloalkyl group, a C1-C30 substituted or unsubstituted alkoxy group, a C1-C30 substituted or unsubstituted silyl group, a C6-C60 substituted or unsubstituted aryl group, or a C3-C30 substituted or unsubstituted heteroaryl group;

$R_6$-$R_7$ are each independently selected from hydrogen, deuterium, halo, cyano, a C1-C30 substituted or unsubstituted alkyl group, a C2-C30 substituted or unsubstituted alkenyl group, a C2-C30 substituted or unsubstituted alkynyl group, a C3-C30 substituted or unsubstituted cycloalkyl group, a C1-C30 substituted or unsubstituted alkoxy group, a C1-C30 substituted or unsubstituted silyl group, a C6-C60 substituted or unsubstituted aryl group, a C3-C30 substituted or unsubstituted heteroaryl group, or a ring A that shares a side with the adjacent phenyl group to form a fused ring, in which the ring A is selected from a phenyl ring, a 3- to 7-membered saturated or partially unsaturated carbocyclic ring, a 3- to 7-membered saturated or partially heterocyclic ring, a fused C6-C60 aryl group or a fused C3-C30 heteroaryl group;

$Ar_1$ and $Ar_2$ are each independently selected from hydrogen, deuterium, halo, cyano, a C1-C30 substituted or unsubstituted alkyl group, a C2-C30 substituted or unsubstituted alkenyl group, a C2-C30 substituted or unsubstituted alkynyl group, a C3-C30 substituted or unsubstituted cycloalkyl group, a C1-C30 substituted or unsubstituted alkoxy group, a C1-C30 substituted or unsubstituted silyl group, a C6-C60 substituted or unsubstituted aryl group, or a C3-C30 substituted or unsubstituted heteroaryl group, where the heteroaryl, heterocyclic ring and fused heteroaryl each independently have at least one heteroatom independently selected from nitrogen, sulfur, oxygen, phosphorus, boron or silicon.

Optionally, in the 9,10-dihydro-acridine derivative, $Ar_1$ and $Ar_2$ are each independently selected from a C6-C60 substituted or unsubstituted aryl group, or a C3-C30 substituted or unsubstituted heteroaryl group.

Optionally, in the 9,10-dihydro-acridine derivative, $Ar_2$ is selected from any of the following groups:

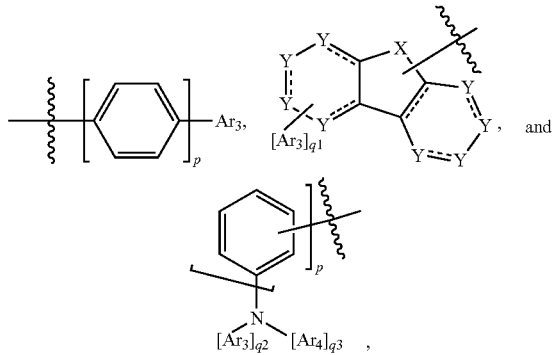

in which, p is an integer from 0 to 5, $q_1$ is an integer from 0 to 6, $q_2$ is an integer from 0 to 4, $q_3$ is an integer from 0 to 4, ====== is selected from a single or double bond; and in

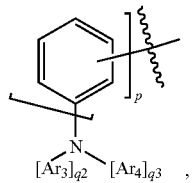

p, $q_2$ and $q_3$ are not all 0;

X is selected from O, S, $C(R_3)(R_4)$ or $N(R_5)$, and Y are each independently selected from carbon or nitrogen; and $Ar_3$ and $Ar_4$ are each independently selected from hydrogen, and the following groups that are unsubstituted or substituted with 1-4 $R_{1a}$:

phenyl, biphenylyl, terphenylyl, indenyl, fluorenyl, naphthyl, azulenyl, pentalenyl, heptalenyl, octalenyl, benzodiindenyl, acenaphthylenyl, phenalenyl, phenanthrenyl, anthracenyl, triindenyl, fluoranthenyl, acephenanthrenyl, aceanthrylenyl, 9,10-benzophenanthrenyl, pyrenyl, 1,2-benzophenanthrenyl, butylphenyl, naphthacenyl, pleiadenyl, picenyl, perylenyl, pentaphenyl, pentacenyl, tetraphenylene, cholanthrenyl, helicenyl, hexaphenyl, rubicenyl, coronenyl, trinaphthylenyl, heptaphenyl, pyranthrenyl, ovalenyl, corannulenyl, anthanthrenyl, truxenyl, furyl, benzofuryl, isobenzofuryl, oxanthracenyl, oxazolinyl, dibenzofuryl, peri-xanthenoxanthenyl, thienyl, thioxanthenyl, thianthrenyl, phenoxathiinyl, thionaphthenyl, isothionaphthenyl, benzothienyl, thiophanthrenyl, dibenzothienyl, pyrrolyl, pyrazolyl, tellurazolyl, selenazolyl, thiazolyl, isothiazolyl, oxazolyl, furazanyl, pyridinyl, pyrazinyl, pyrimidinyl, pyridazinyl, triazinyl, indolizinyl, indolyl, isoindolyl, indazolyl, purinyl, quinolizinyl, isoquinolyl, carbazolyl, indolocarbazolyl, imidazolyl, naphthyridinyl, phthalazinyl, quinazolinyl, benzodiazepinyl, quinoxalinyl, cinnolinyl, quinolyl, pteridinyl, phenanthridinyl, acridinyl, perimidinyl, phenanthrolinyl, phenazinyl, carbolinyl, phenotellurazinyl, phenoselenazinyl, phenothiazinyl, phenoxazinyl, triphenodithiazinyl, triphenodioxazinyl, anthrazinyl, benzothiazolyl, benzoimidazolyl, benzoxazolyl, benzisoxazolyl, benzoisothiazolyl, or a fused cyclic group, a spirocyclic group or a bicyclic group formed by the aforesaid groups;

in which $R_{1a}$ is a $C_1$-$C_6$ alkyl group.

Optionally, in the 9,10-dihydro-acridine derivative, $Ar_1$ is selected from hydrogen or any of the following groups:

phenyl, biphenylyl, terphenylyl, indenyl, fluorenyl, naphthyl, azulenyl, pentalenyl, heptalenyl, octalenyl, benzodiindenyl, acenaphthylenyl, phenalenyl, phenanthrenyl, anthracenyl, triindenyl, fluoranthenyl, acephenanthrenyl, aceanthrylenyl, 9,10-benzophenanthrenyl, pyrenyl, 1,2-benzophenanthrenyl, butylphenyl, naphthacenyl, pleiadenyl, picenyl, perylenyl, pentaphenyl, pentacenyl, tetraphenylene, cholanthrenyl, helicenyl, hexaphenyl, rubicenyl, coronenyl, trinaphthylenyl, heptaphenyl, pyranthrenyl, ovalenyl, corannulenyl, anthanthrenyl, truxenyl, furyl, benzofuryl, isobenzofuryl, oxanthracenyl, oxazolinyl, dibenzofuryl, peri-xanthenoxanthenyl, thienyl, thioxanthenyl, thianthrenyl, phenoxathiinyl, thionaphthenyl, isothionaphthenyl, benzothienyl, thiophanthrenyl, dibenzothienyl, pyrrolyl, pyrazolyl, tellurazolyl, selenazolyl, thiazolyl, isothiazolyl, oxazolyl, furazanyl, pyridinyl, pyrazinyl, pyrimidinyl, pyridazinyl, triazinyl, indolizinyl, indolyl, isoindolyl, indazolyl, purinyl, quinolizinyl, isoquinolyl, carbazolyl, indolocarbazolyl, imidazolyl, naphthyridinyl, phthalazinyl, quinazolinyl, benzodiazepinyl, quinoxalinyl, cinnolinyl, quinolyl, pteridinyl, phenanthridinyl, acridinyl, perimidinyl, phenanthrolinyl, phenazinyl, carbolinyl, phenotellurazinyl, phenoselenazinyl, phenothiazinyl, phenoxazinyl, triphenodithiazinyl, triphenodioxazinyl, anthrazinyl, benzothiazolyl, benzoimidazolyl, benzoxazolyl, benzisoxazolyl, benzoisothiazolyl, or a fused cyclic group, a spirocyclic group or a bicyclic group formed by the aforesaid groups.

Optionally, in the 9,10-dihydro-acridine derivative, $R_1$-$R_5$ are each independently selected from hydrogen, a $C_1$-$C_6$ alkyl group, phenyl, biphenylyl, naphthyl, anthracenyl, phenanthrenyl, fluorenyl, pyrenyl, perylenyl, corranulenyl, triphenylene, fluoranthenyl, pyridinyl, pyrimidinyl, pyranyl, thiopyranyl, pyrazinyl, pyridazinyl, triazinyl, phthalazinyl, phenazinyl, thienyl, furyl, pyrrolyl, pyrazolyl, imidazolyl, oxazolyl, thiazolyl, indolyl, carbazolyl, indolocarbazolyl, triarylamino, diarylamino, phenanthridinyl, acridinyl, perimidinyl, pteridinyl, quinazolinyl, quinoxalinyl, cinnolinyl, quinolyl, phenanthrolinyl or carbolinyl;

$R_6$-$R_7$ are each independently selected from hydrogen, a $C_1$-$C_6$ alkyl group, phenyl, biphenylyl, naphthyl, anthracenyl, phenanthrenyl, fluorenyl, pyrenyl, perylenyl, corranulenyl, triphenylene, fluoranthenyl, pyridinyl, pyrimidinyl, pyranyl, thiopyranyl, pyrazinyl, pyridazinyl, triazinyl, phthalazinyl, phenazinyl, thienyl, furyl, pyrrolyl, pyrazolyl, imidazolyl, oxazolyl, thiazolyl, indolyl, carbazolyl, indolocarbazolyl, triarylamino, diarylamino, phenanthridinyl, acridinyl, perimidinyl, pteridinyl, quinazolinyl, quinoxalinyl, cinnolinyl, quinolyl, phenanthrolinyl, carbolinyl, or a ring A that shares a side with the adjacent phenyl group to form a fused ring, where the ring A is selected from

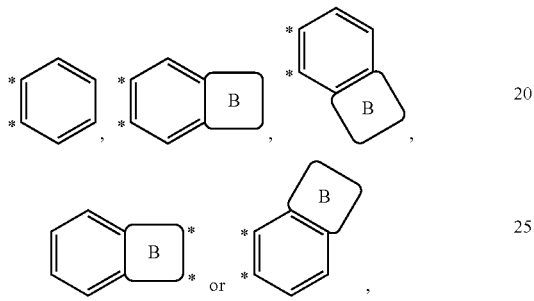

in which the ring B is selected from a benzene ring, a biphenyl ring, a naphthalene ring, an anthracene ring, a phenanthrene ring, a fluorene ring, a pyrene ring, a perylene ring, a corranulene ring, a triphenylene ring, a fluoranthene ring, a pyridine ring, a pyrimidine ring, a pyran ring, a thiapyran ring, a pyrazine ring, a pyridazine ring, a triazine ring, a phthalazine ring, a phenazine ring, a thiophene ring, a furan ring, a pyrrole ring, a pyrazole ring, an imidazole ring, an oxazole ring, a thiazole ring, an indole ring, a carbazole ring, an ndolocarbazole ring, a triarylamine ring, a diarylamine ring, a phenanthridine ring, an acridine ring, a perimidine ring, a pteridine ring, a quinazoline ring, a quinoxaline ring, a cinnoline ring, a quinoline ring, a phenanthroline ring or a carboline ring.

Optionally, the 9,10-dihydro-acridine derivative has any of the following molecular structures:

(C-1)

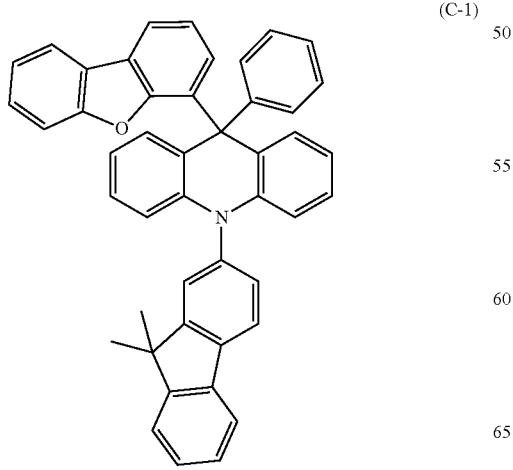

(C-2)

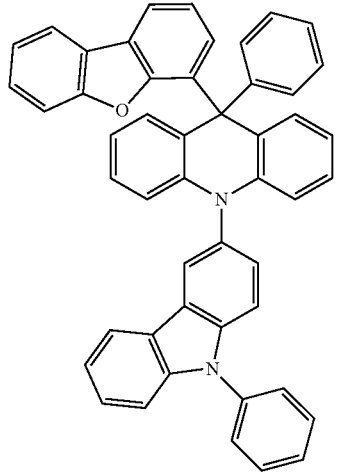

(C-3)

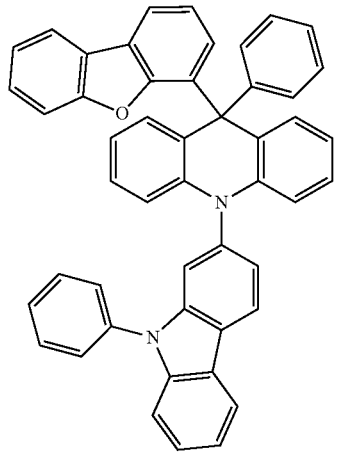

(C-4)

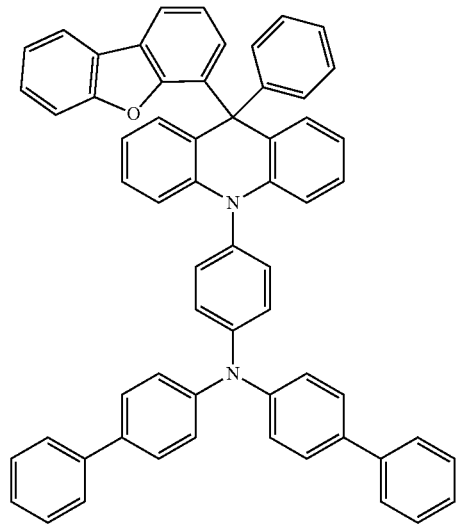

(C-5)
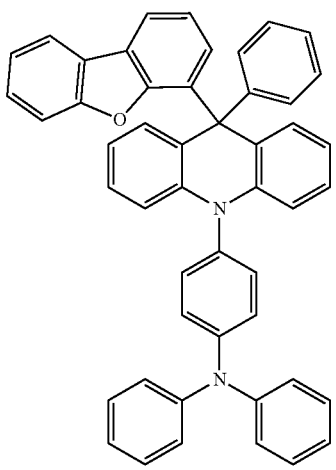
(C-6)
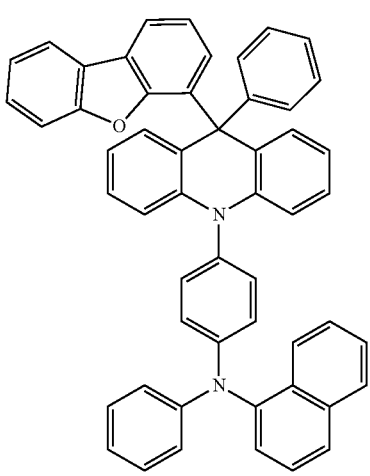
(C-7)
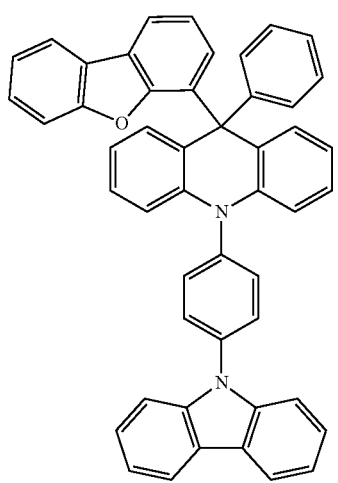
(C-8)
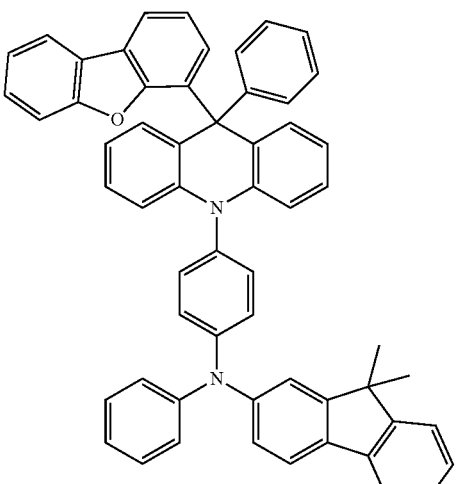
(C-9)
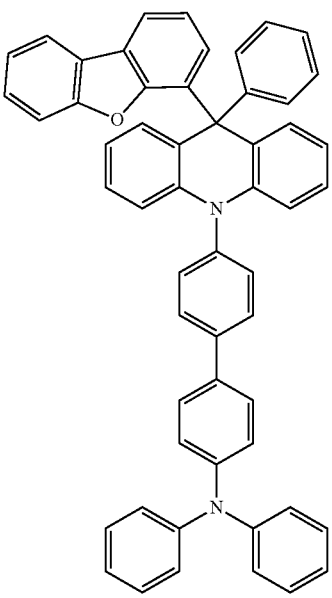

(C-10)
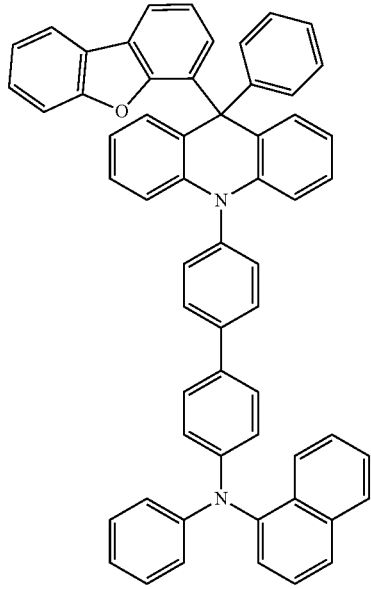
(C-11)
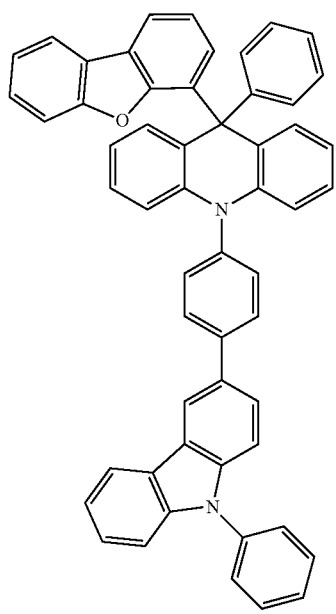
(C-12)
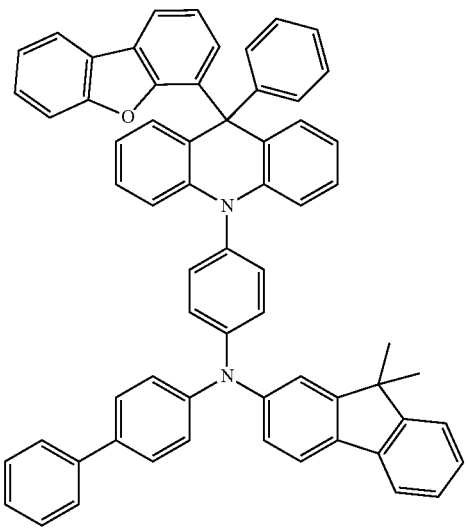
(C-13)
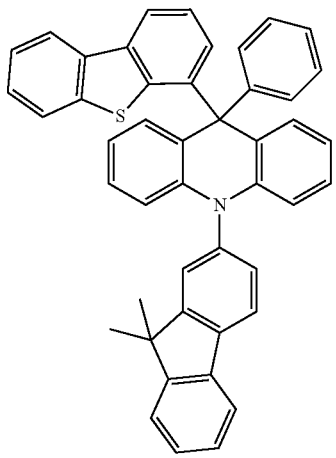
(C-14)
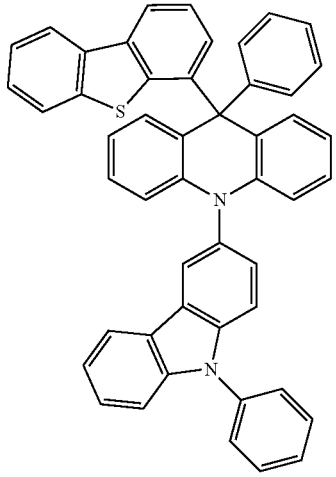

-continued
(C-15)
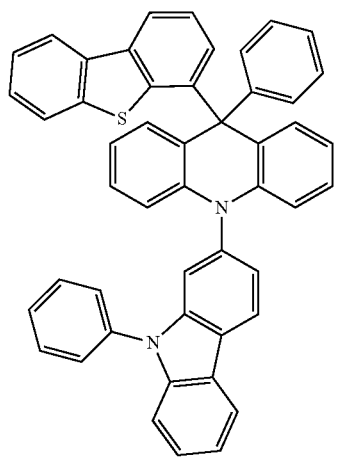
(C-18)
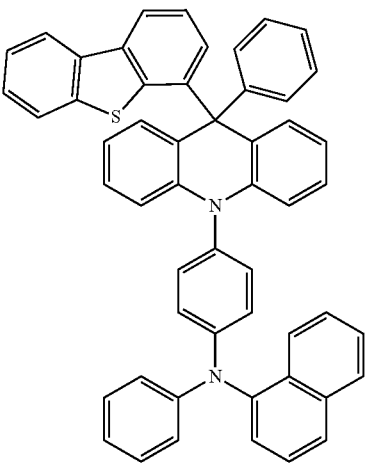
(C-16)
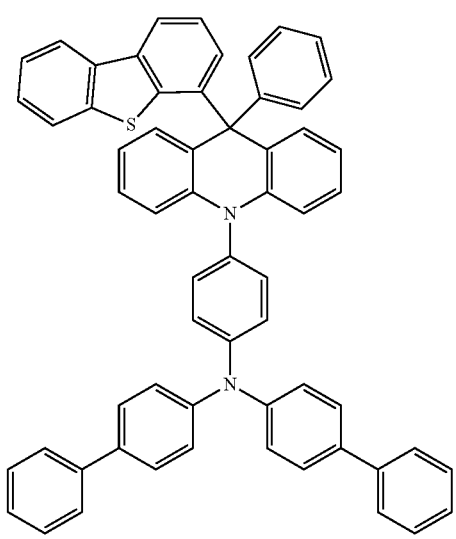
(C-19)
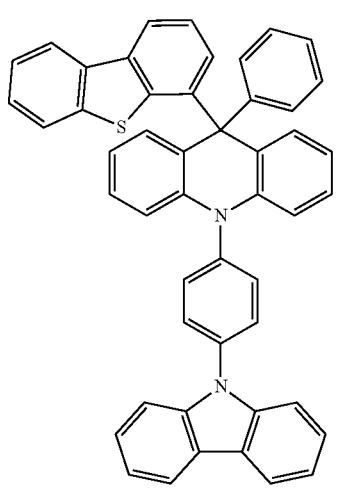
(C-17)
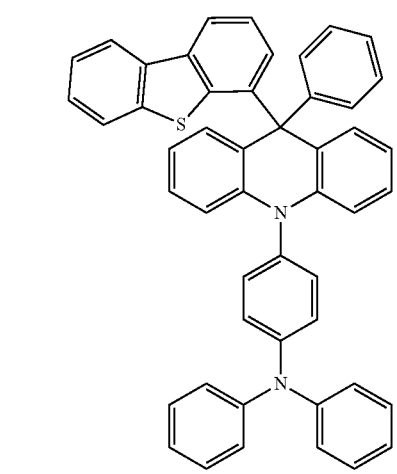
(C-20)
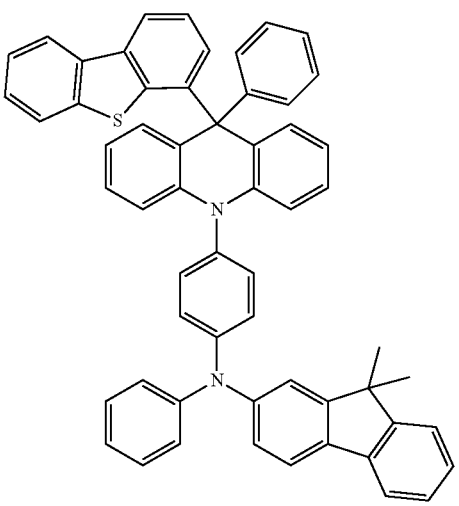

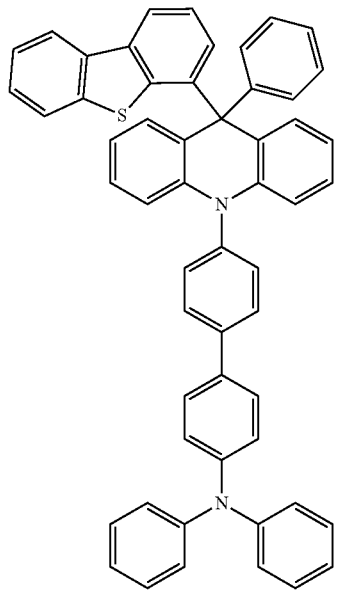
(C-21)
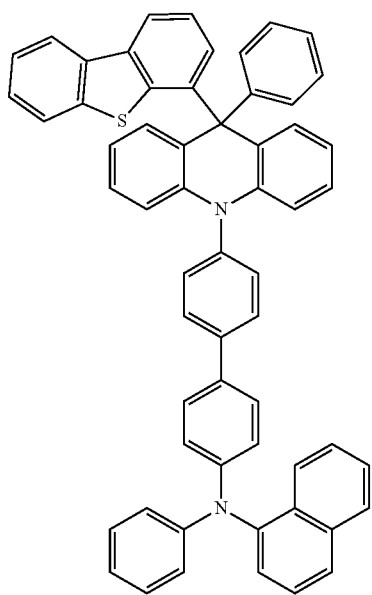
(C-22)
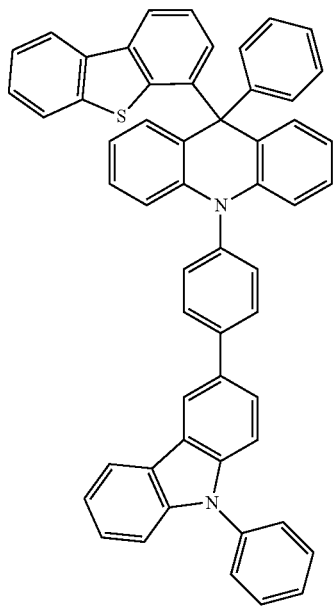
(C-23)
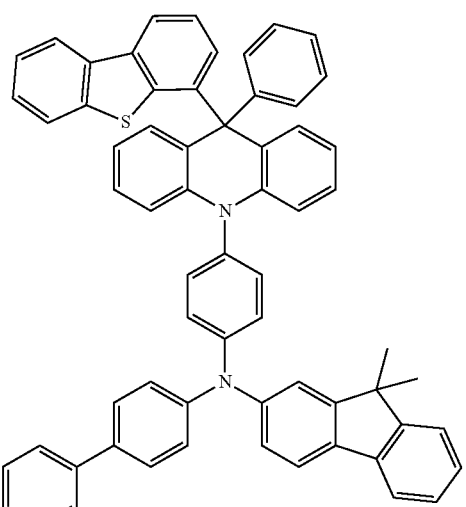
(C-24)
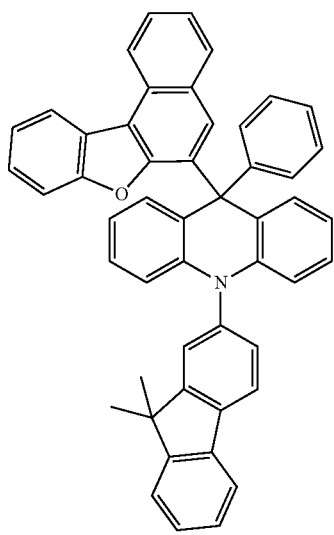
(C-25)

(C-26)
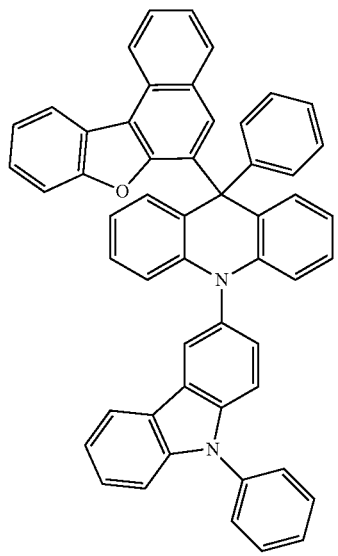
(C-27)
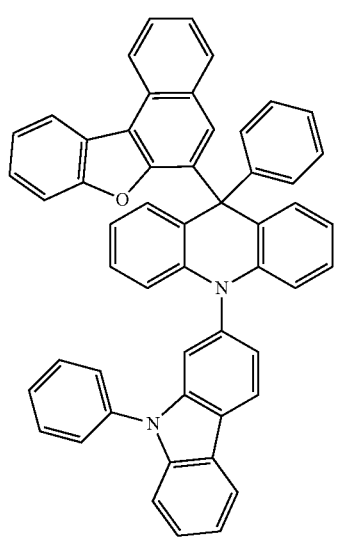
(C-28)
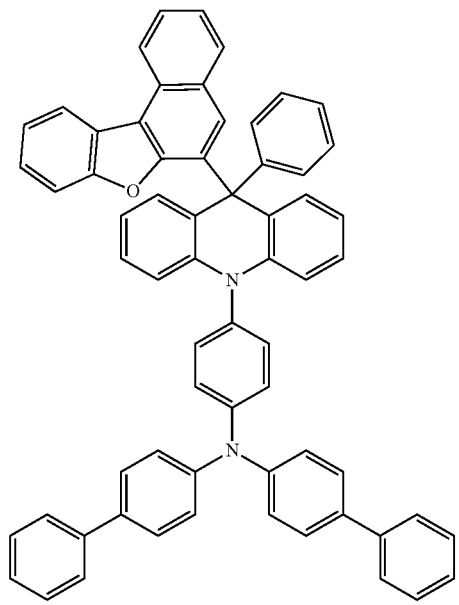
(C-29)
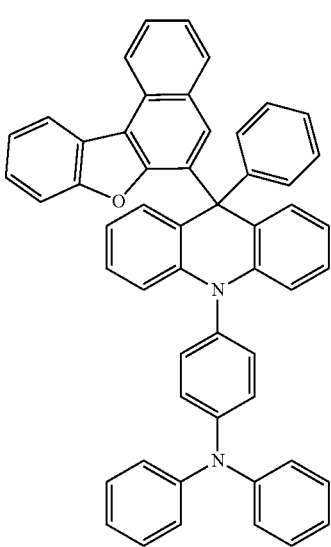

-continued
(C-30)
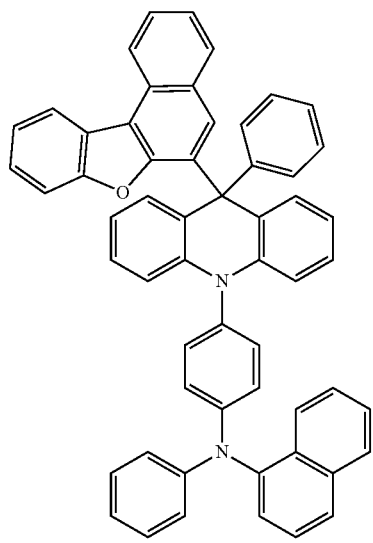
(C-31)
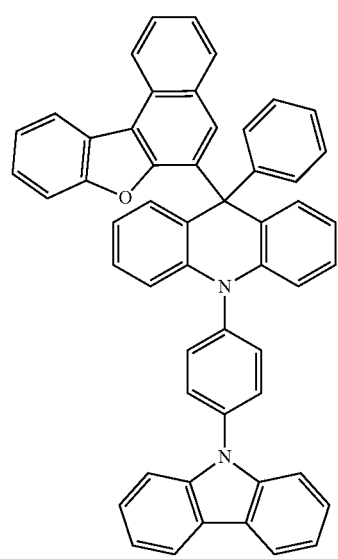
(C-32)
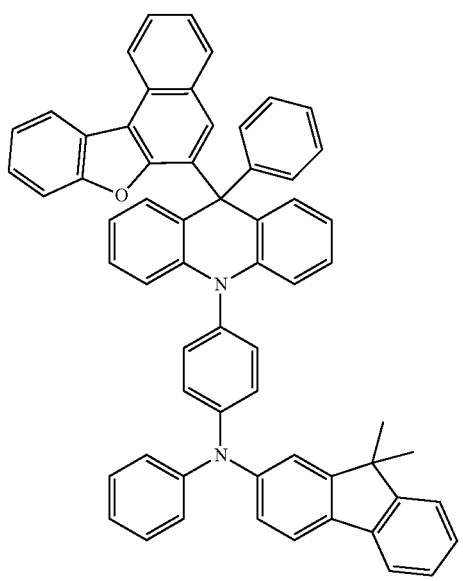
(C-33)
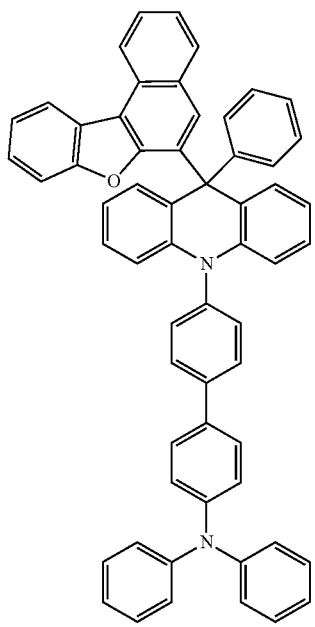
(C-34)
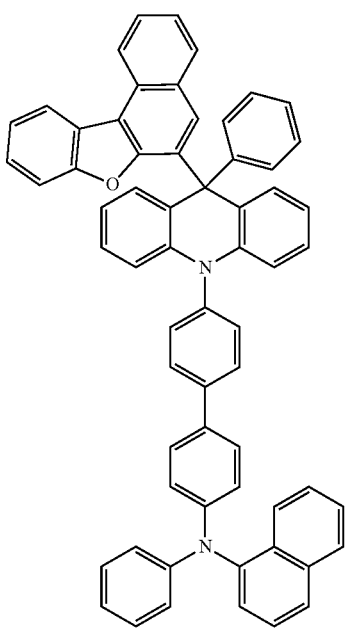

(C-35)
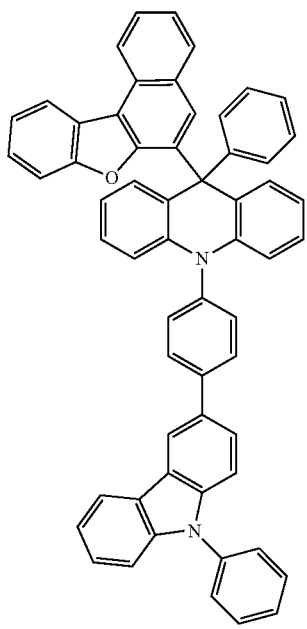
(C-36)
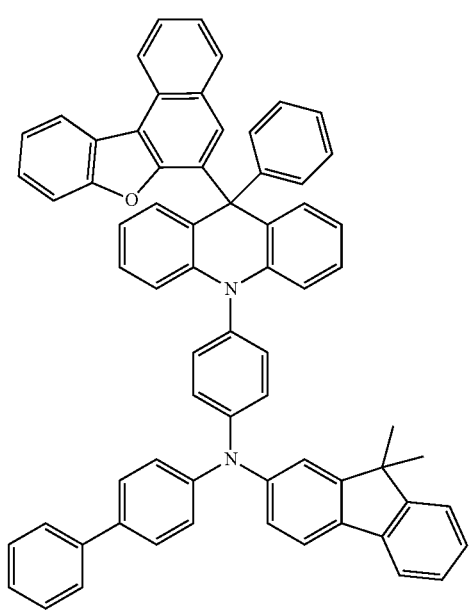
(C-37)
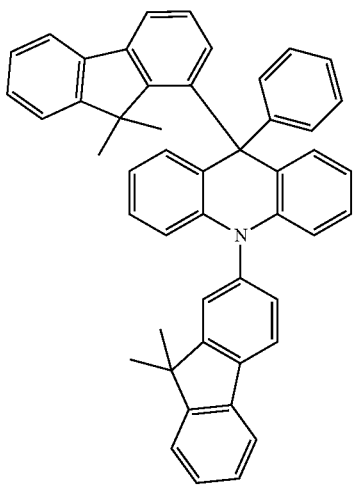
(C-38)
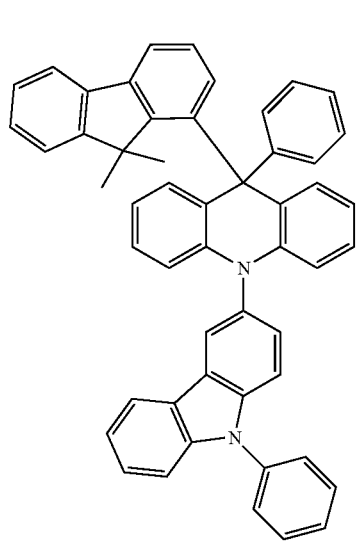
(C-39)
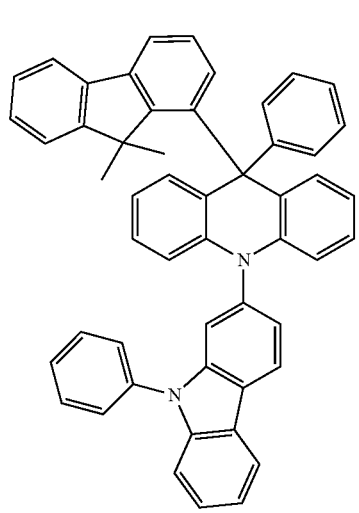

(C-40)
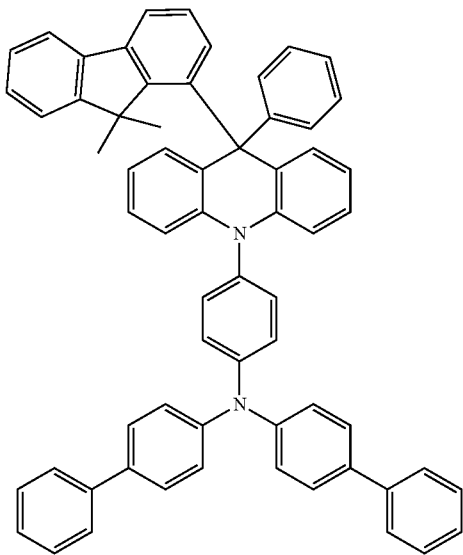
(C-41)
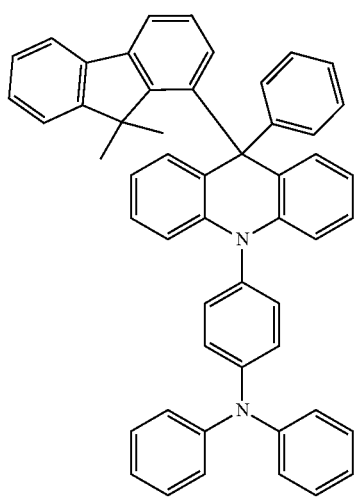
(C-42)
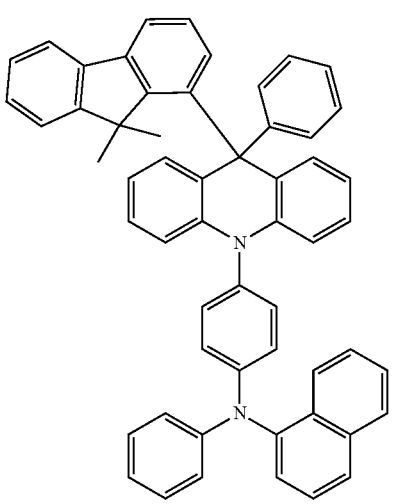
(C-43)
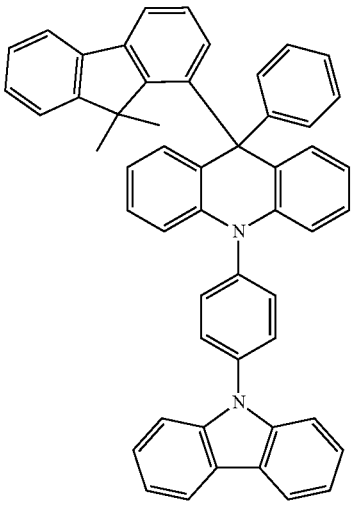
(C-44)
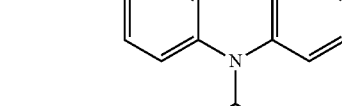
(C-45)
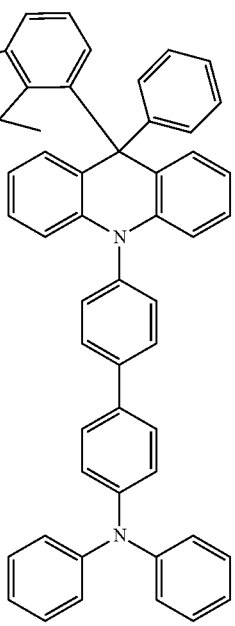

(C-46)
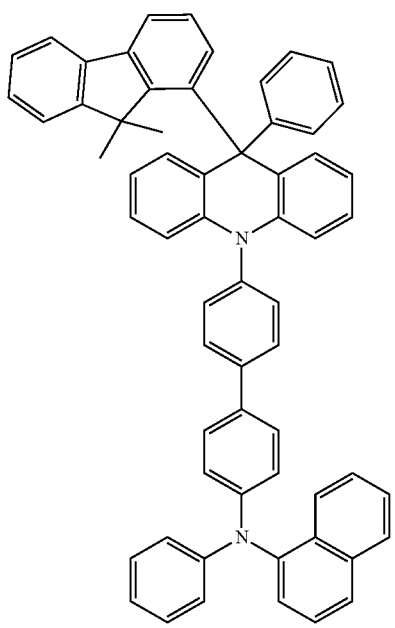
(C-47)
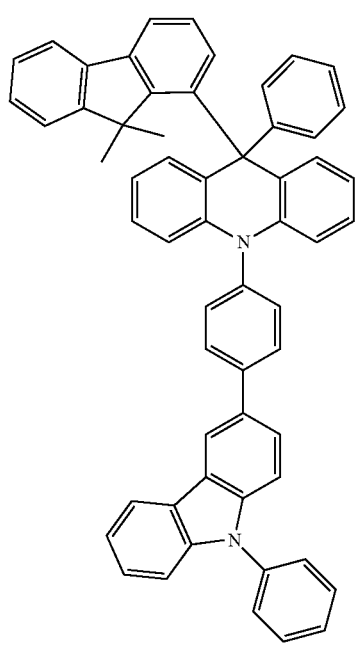
(C-48)
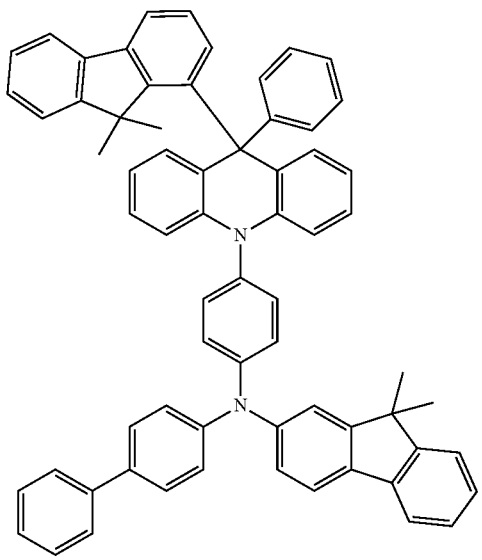
(C-49)
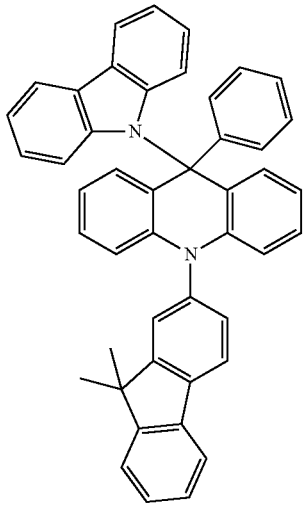
(C-50)
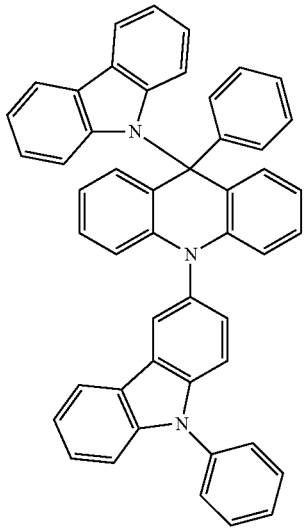

(C-51)
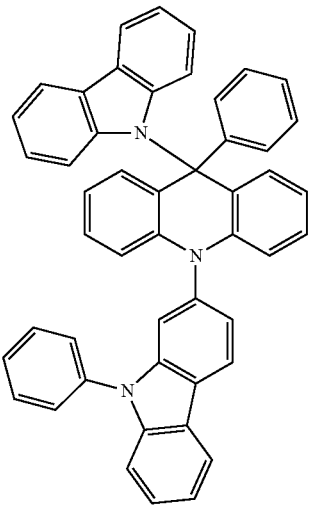
(C-52)
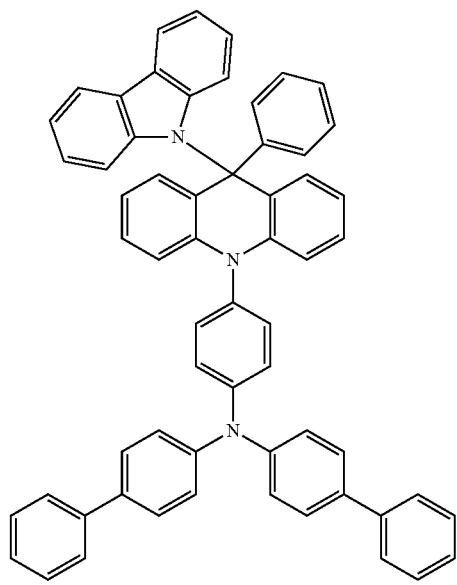
(C-53)
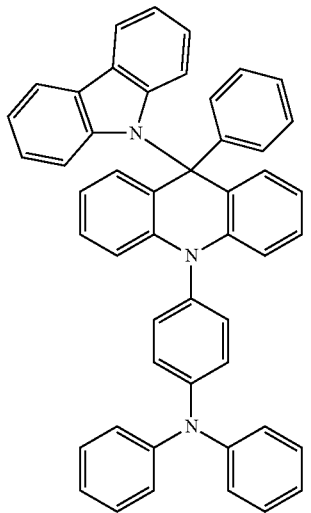
(C-54)
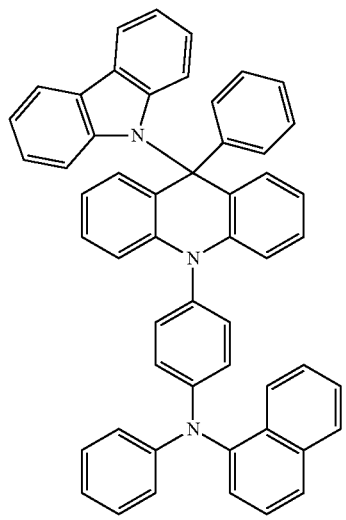
(C-55)
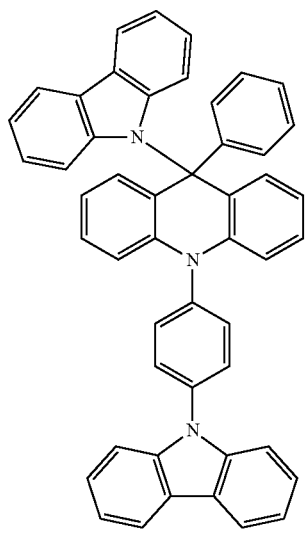
(C-56)
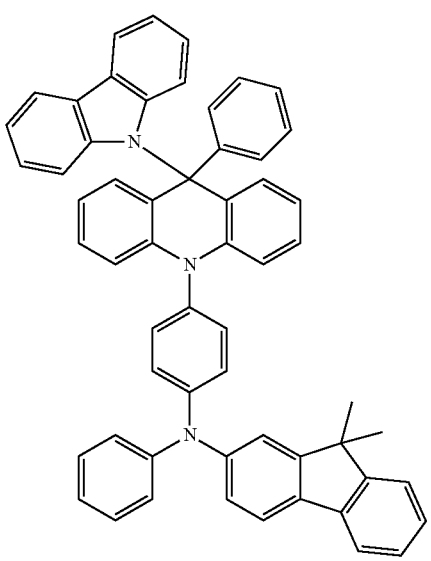

(C-57)
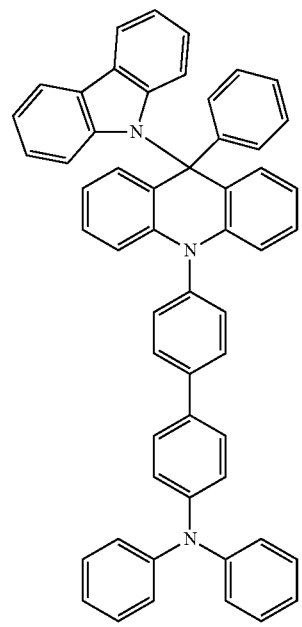
(C-58)
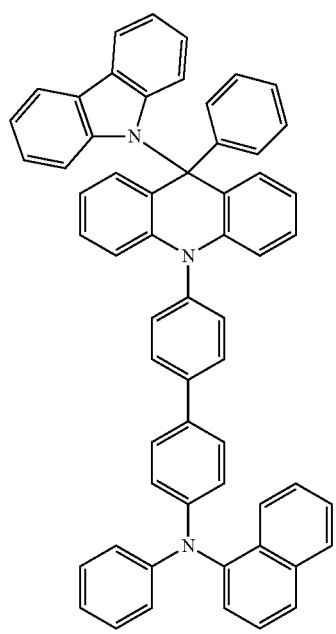
(C-59)
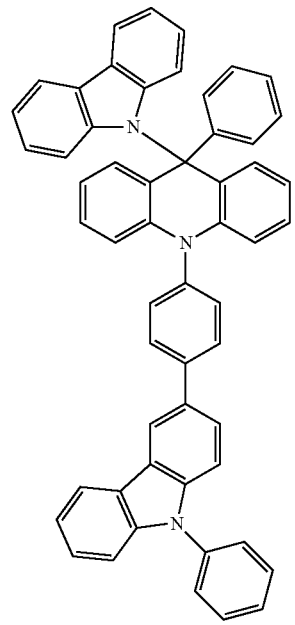
(C-60)
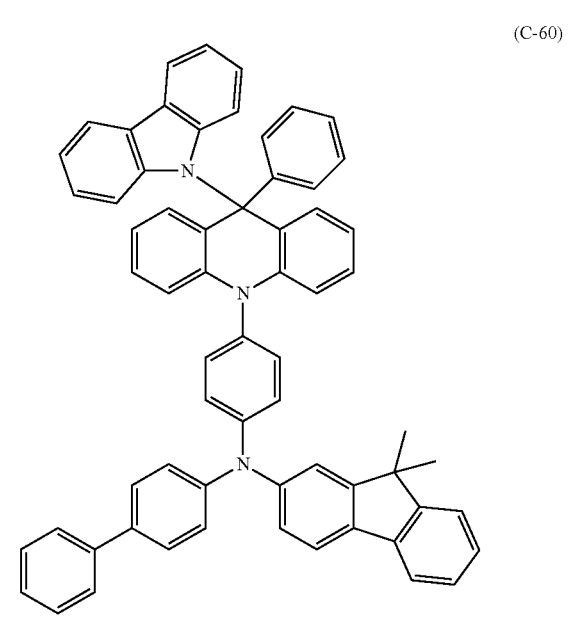

(C-61)
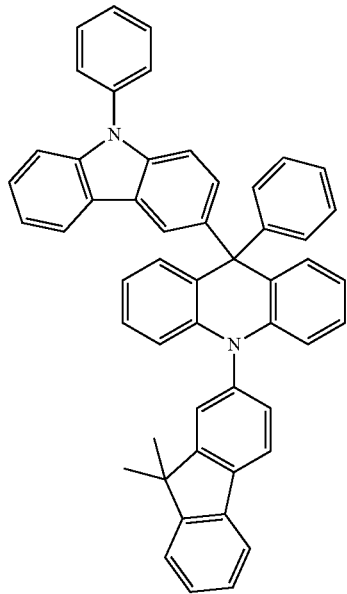
(C-63)
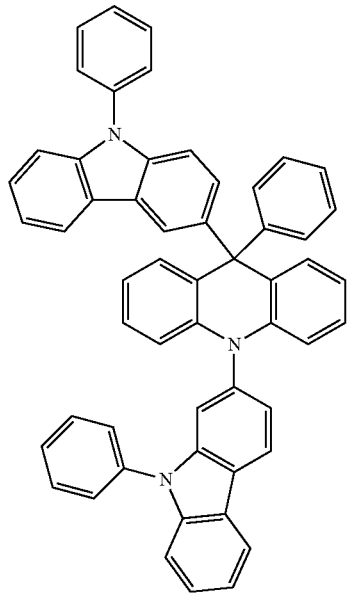
(C-62)
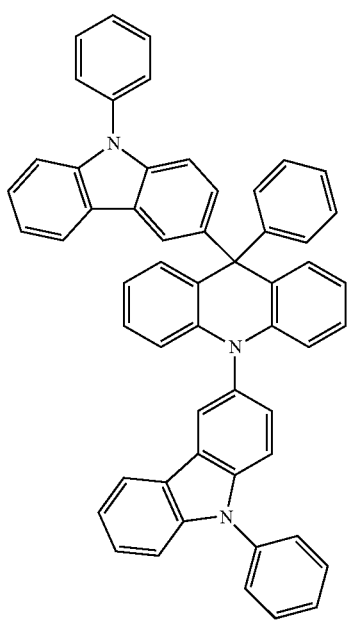
(C-64)
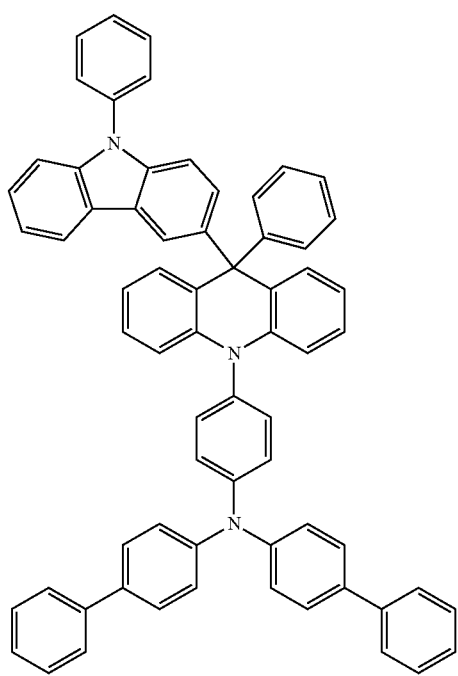

(C-65)
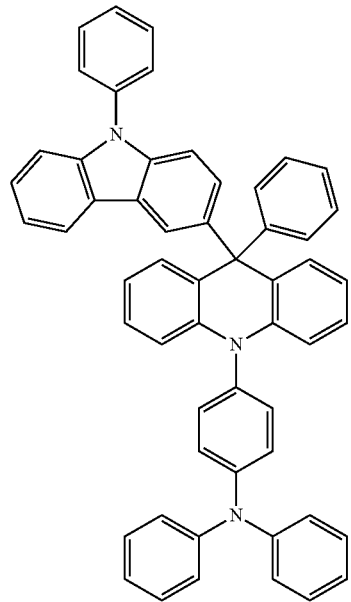
(C-67)
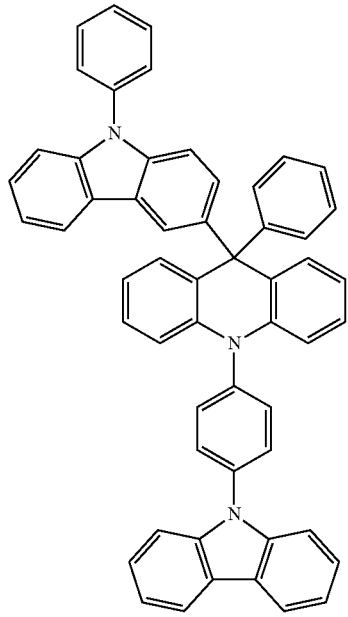
(C-66)
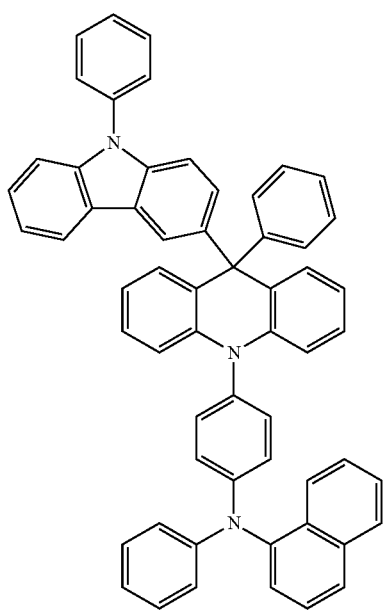
(C-68)
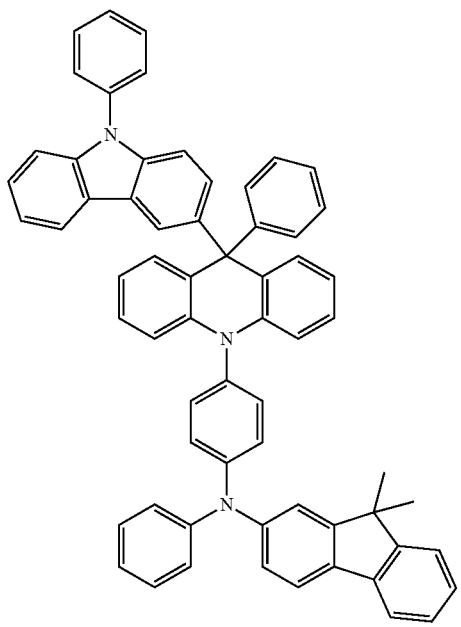

-continued
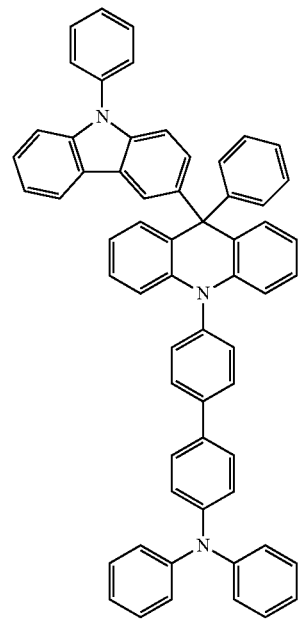
(C-69)
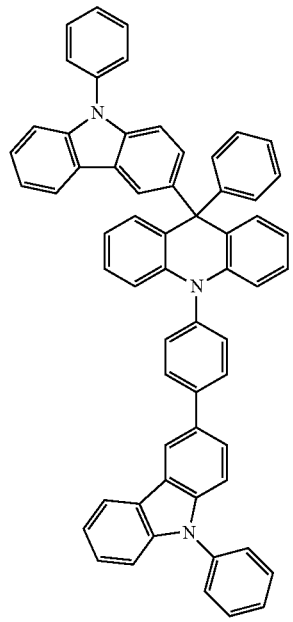
(C-71)
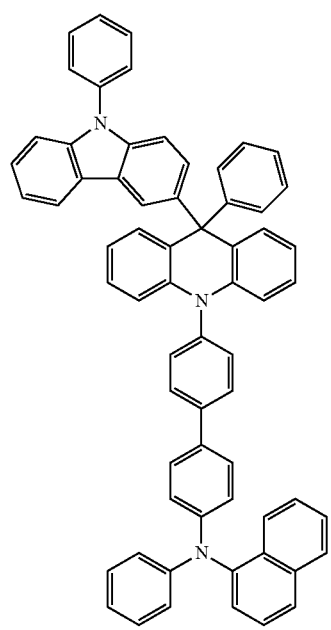
(C-70)
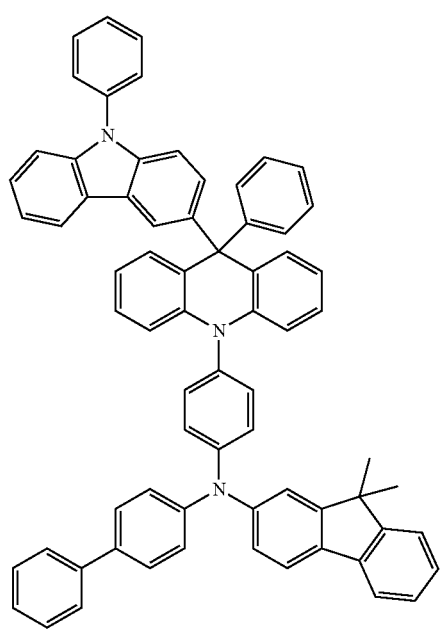
(C-72)

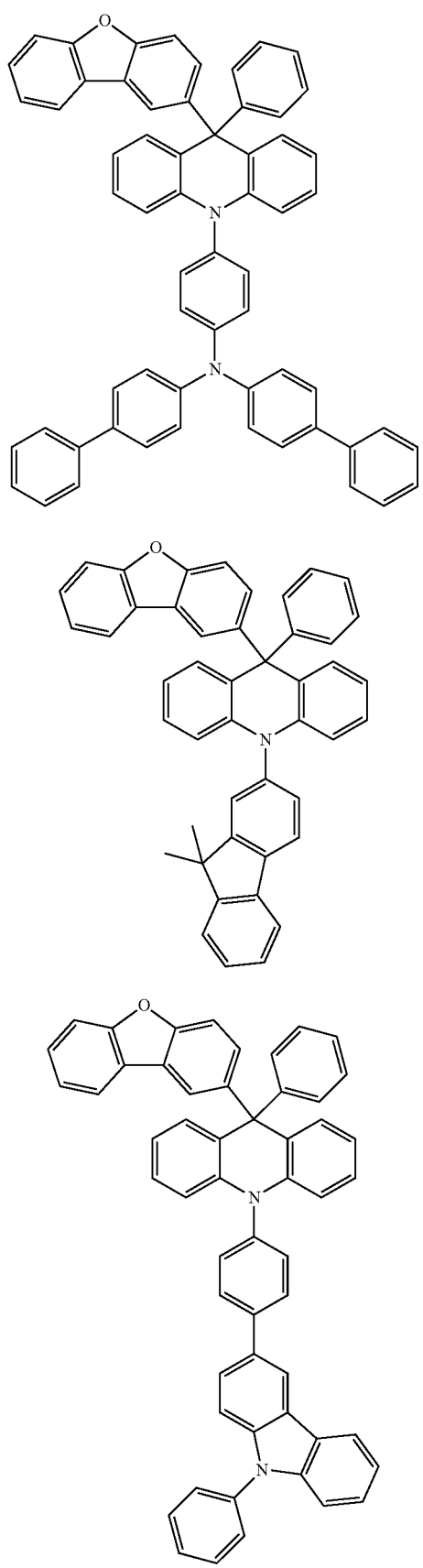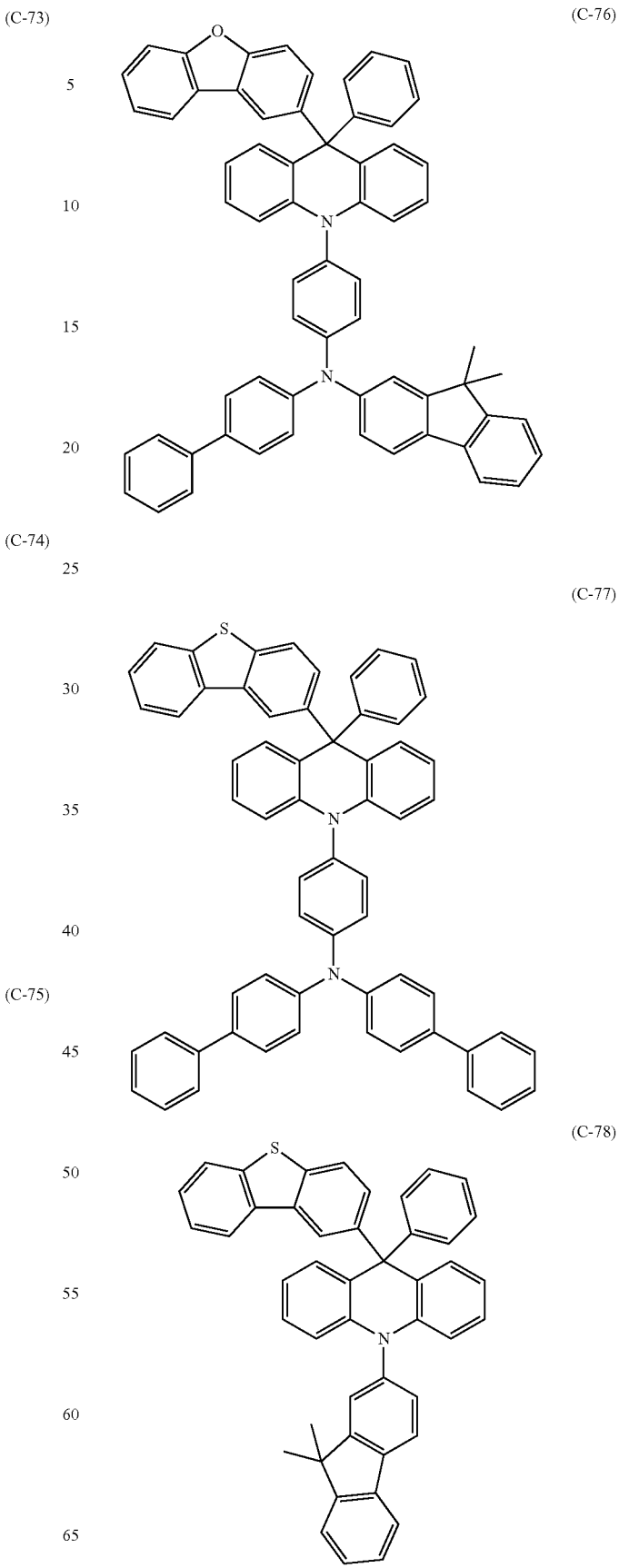

(C-79)
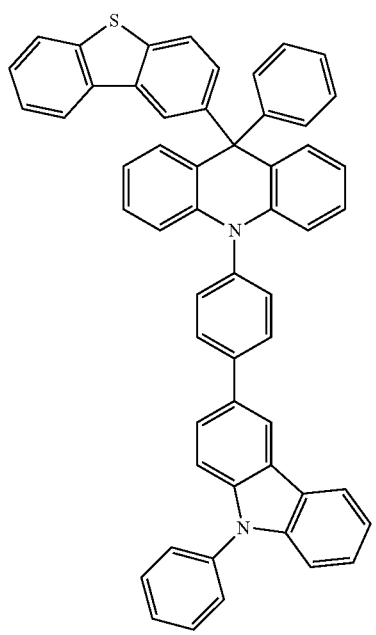
(C-81)
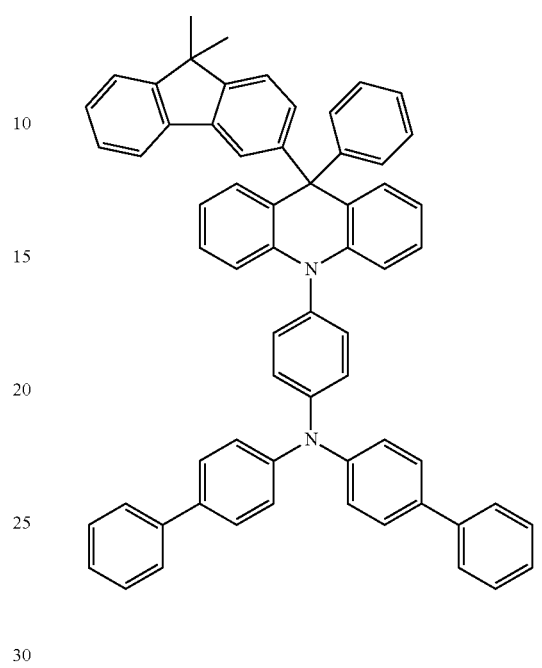
(C-80)
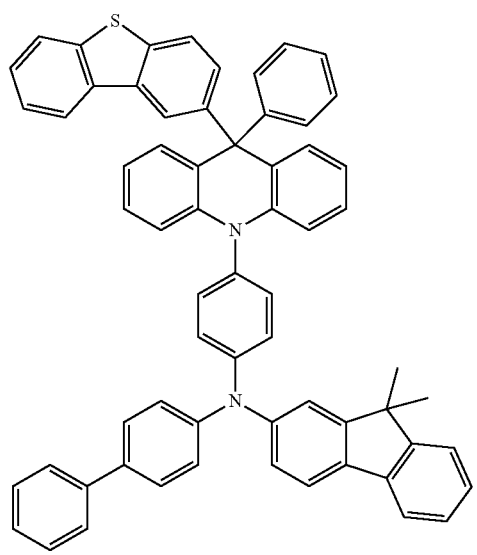
(C-82)
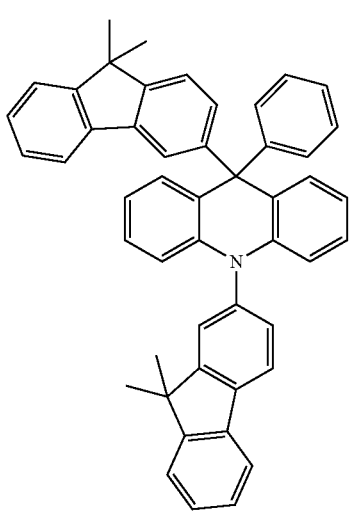

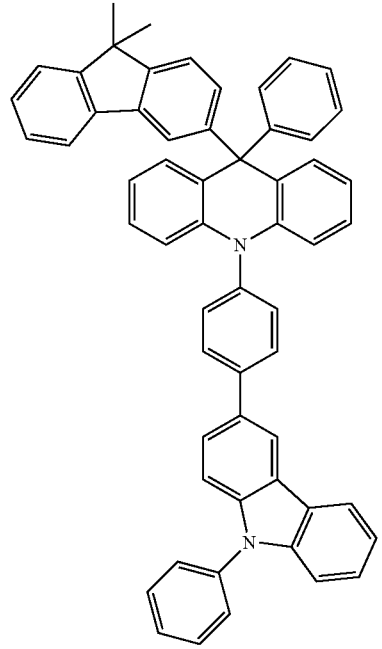
(C-83)
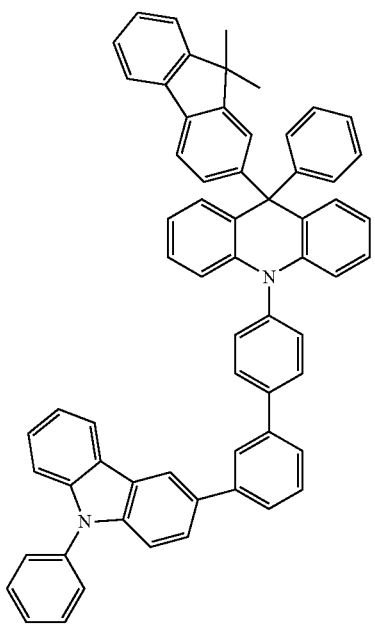
(C-85)
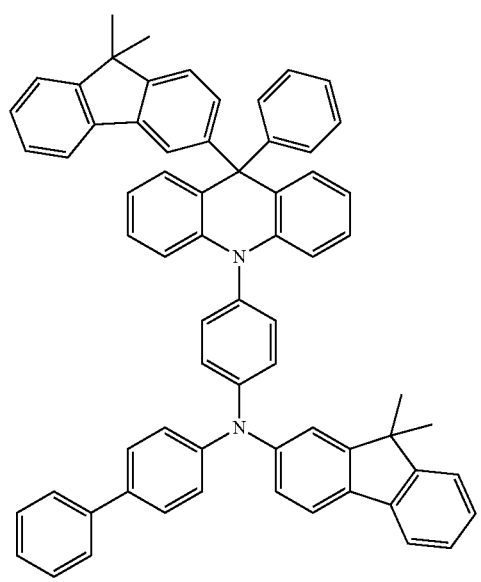
(C-84)
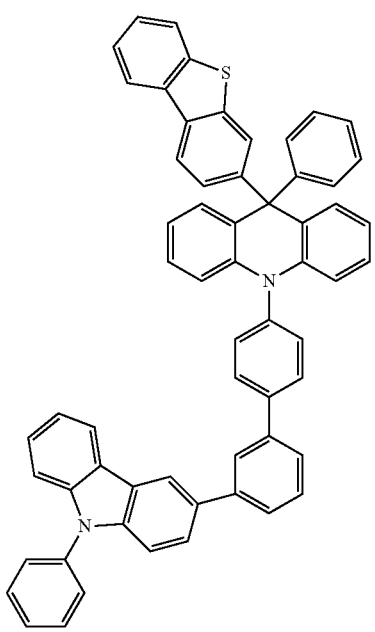
(C-86)

(C-87)
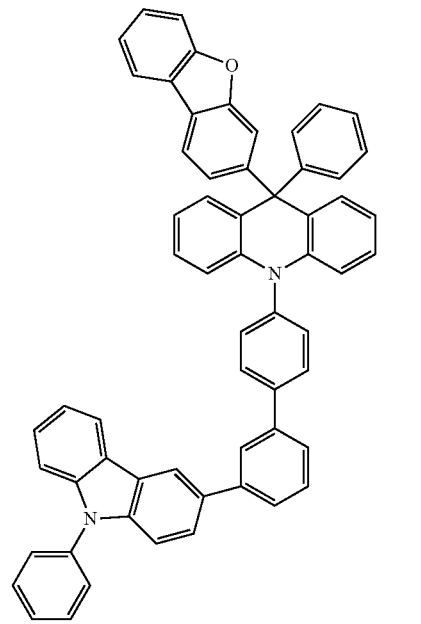
(C-88)
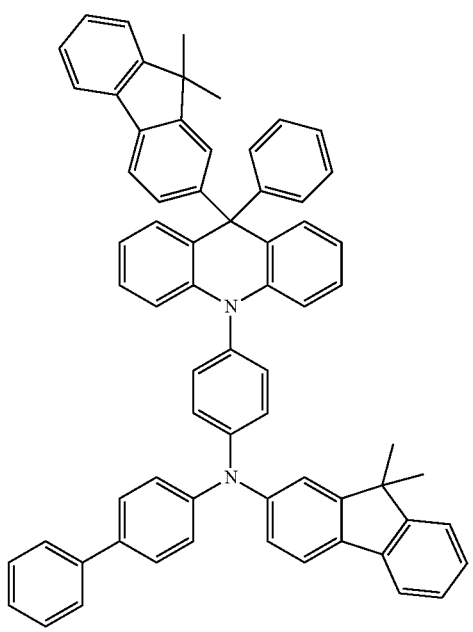
(C-89)
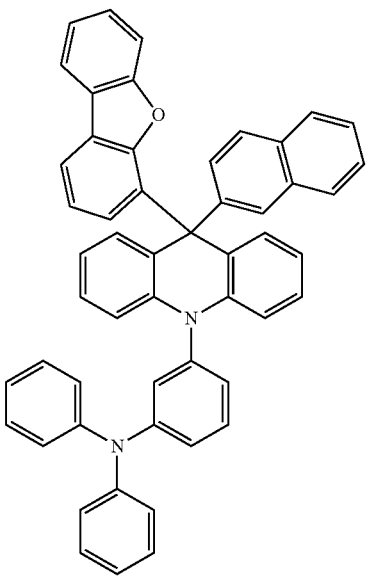
(C-90)
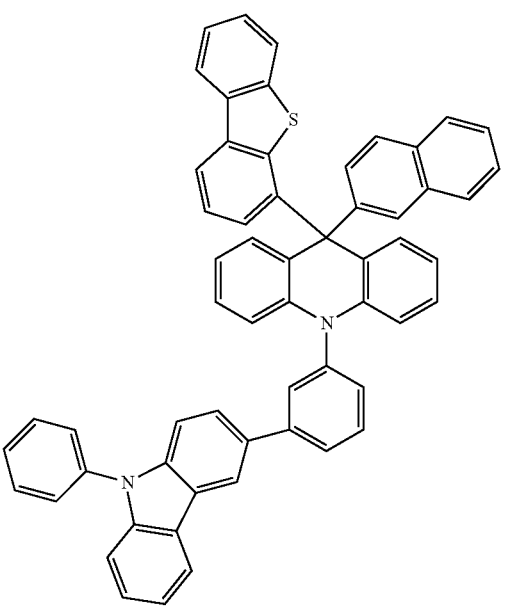

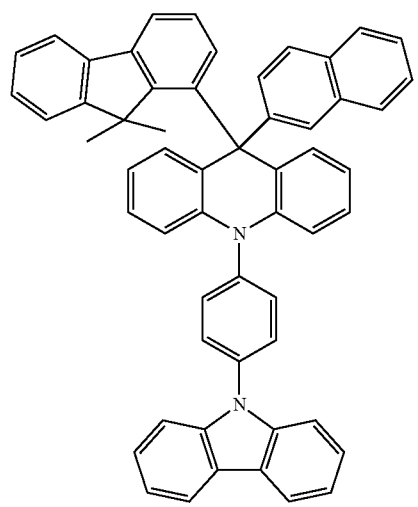
(C-91)
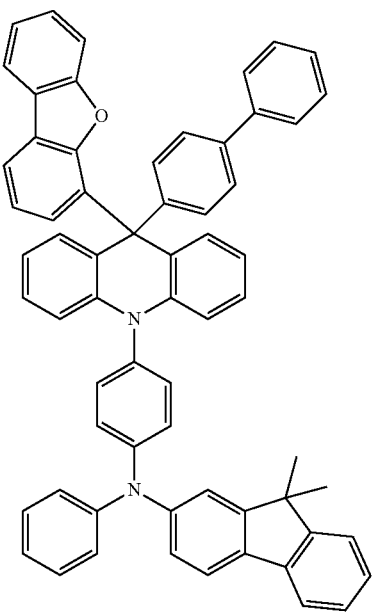
(C-93)
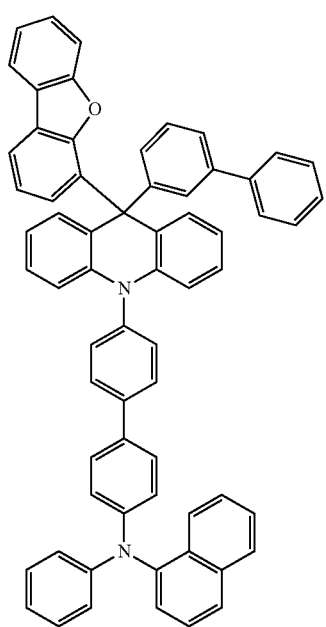
(C-92)
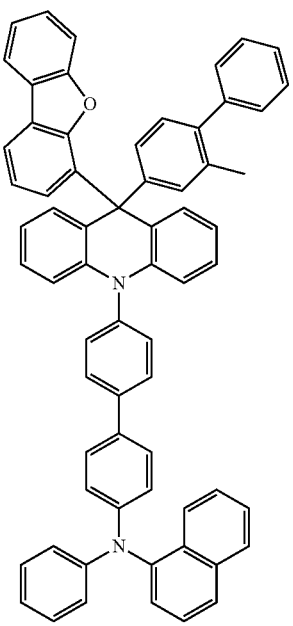
(C-94)

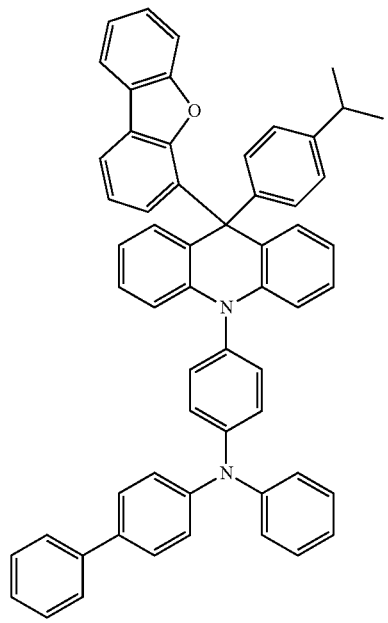
(C-95)
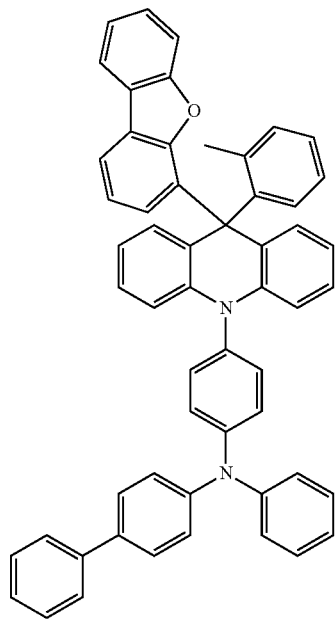
(C-97)
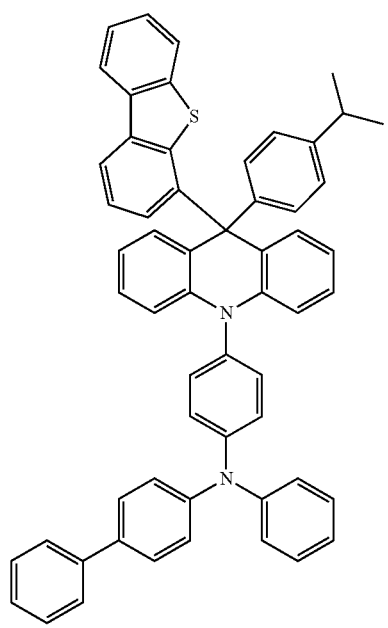
(C-96)
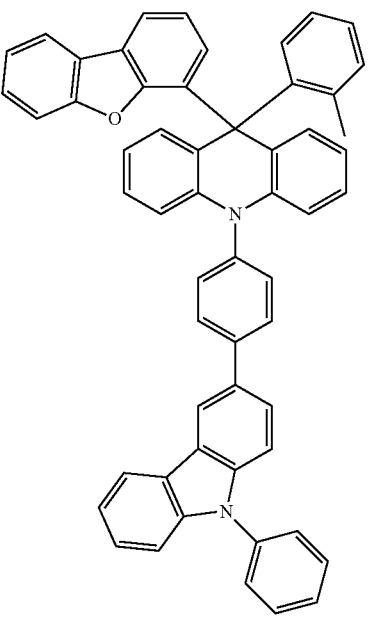
(C-98)

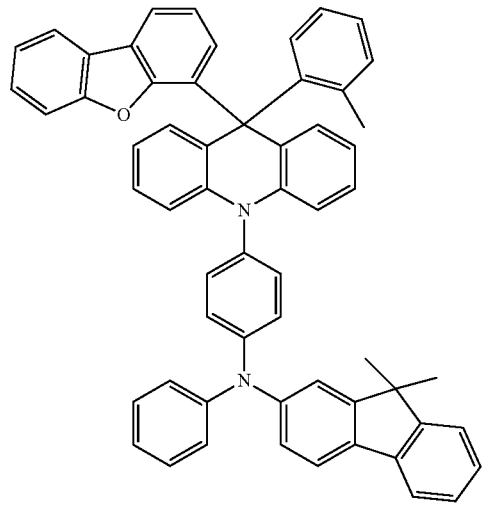
(C-99)
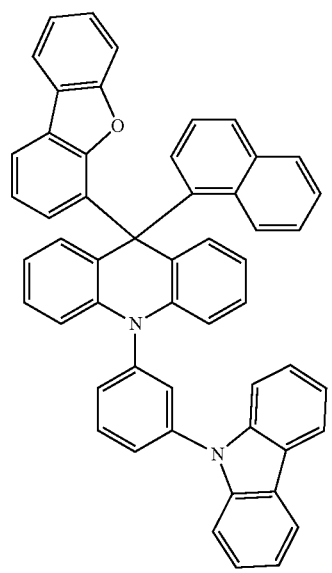
(C-100)
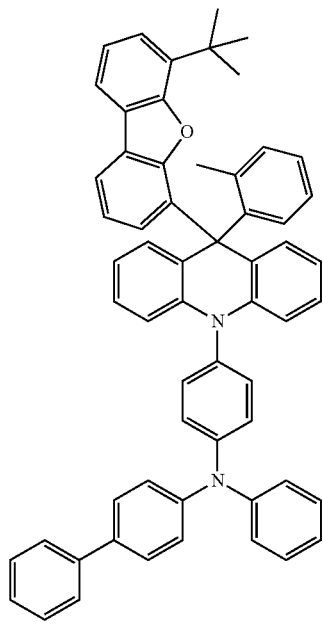
(C-101)
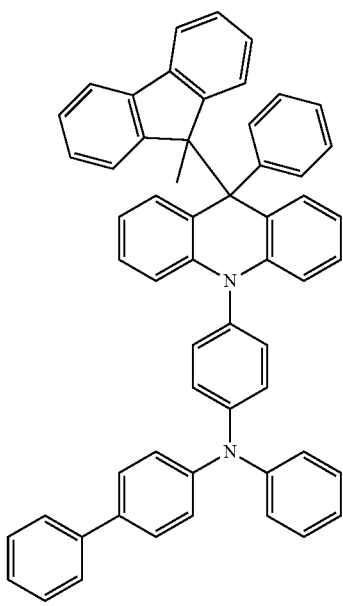
(C-102)

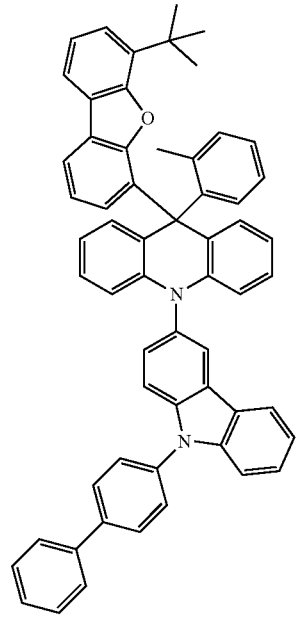
(C-103)
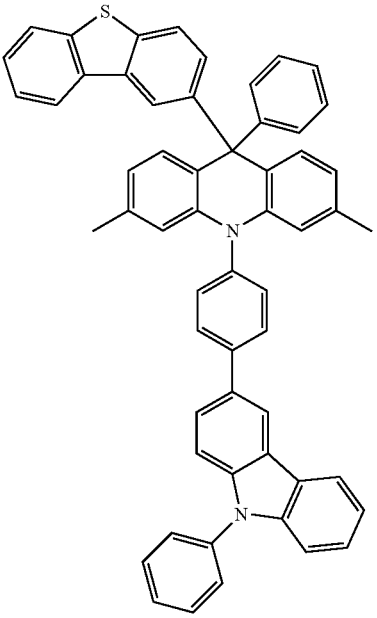
(C-105)
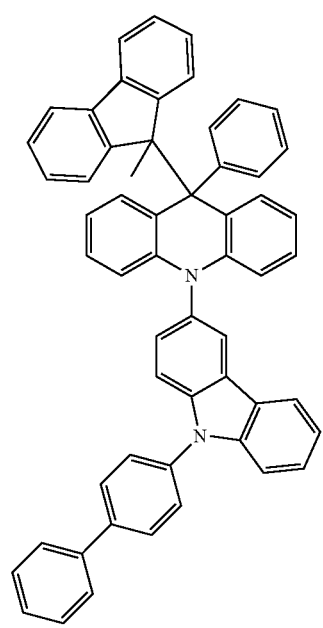
(C-104)
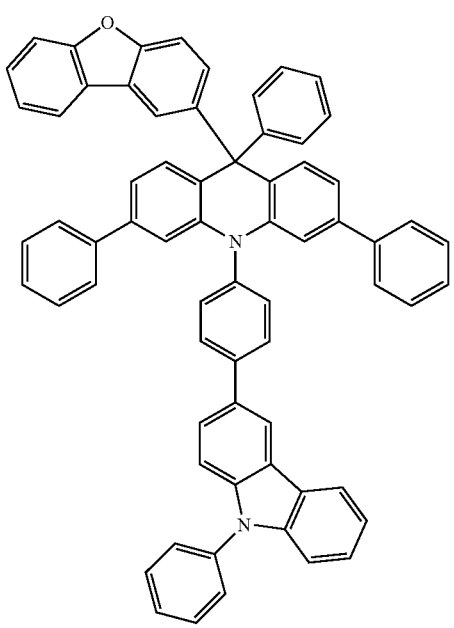
(C-106)

(C-107)

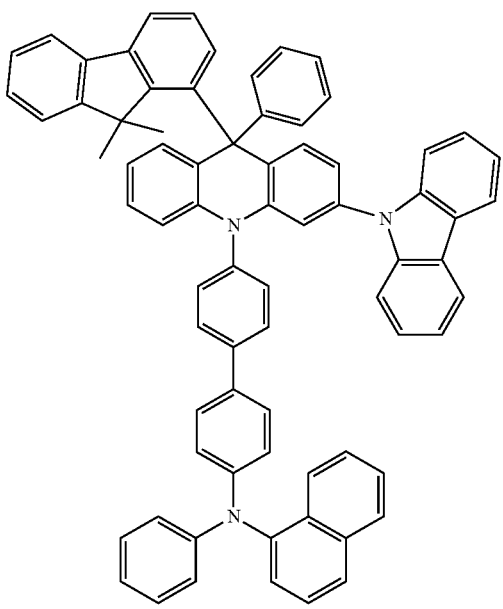

(C-108)

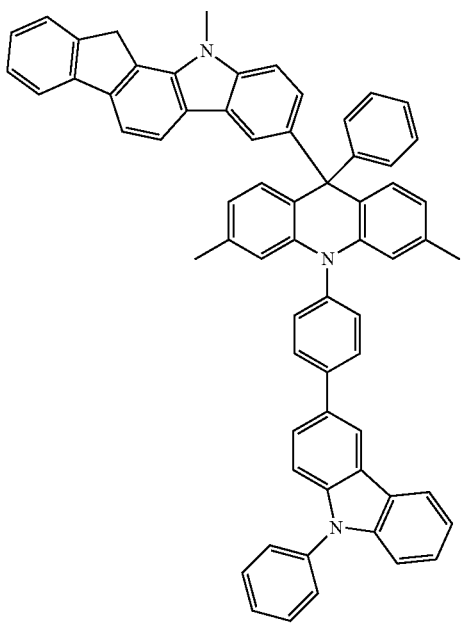

(C-109)

The present invention provides a method for preparing the 9,10-dihydro-acridine derivative. The compound of Formula (I) is synthesized through the following steps:

subjecting a compound of Formula (A) and a compound of Formula (B) as starting materials to a nucleophilic addition reaction, to obtain an intermediate 1; subjecting the intermediate 1 and a compound of Formula (D) to a dehydration-condensation reaction in the presence of Eaton's Reagent, to obtain an intermediate 2; and subjecting the intermediate 2 and a compound of Formula (E) to a coupling reaction in the presence of a catalyst, to obtain the compound of Formula (I);

where the synthesis route for the compound of Formula (I) is shown below:

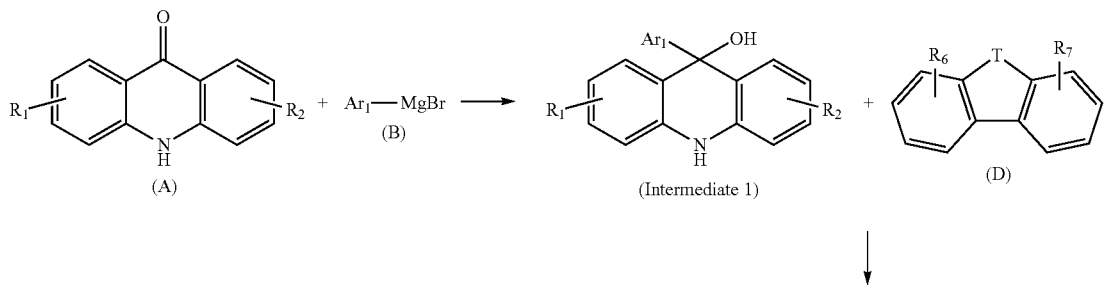

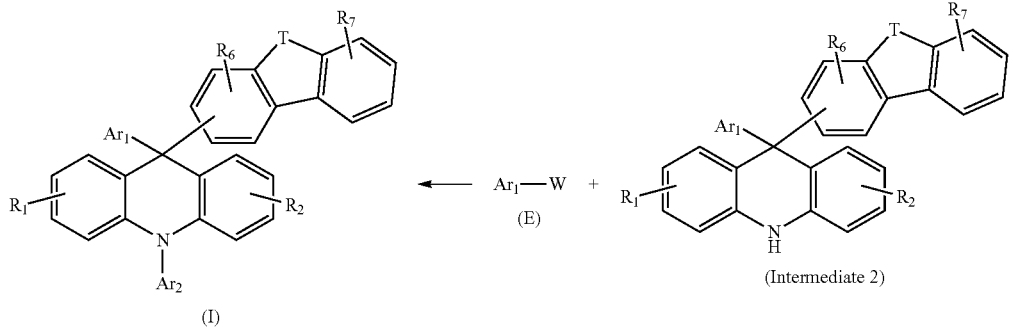

or subjecting the compound of Formula (A) and the compound of Formula (E) as starting materials to a nucleophilic addition reaction, to obtain an intermediate 3; subjecting the intermediate 3 to a nucleophilic substitution reaction, to obtain an intermediate 3'; subjecting the intermediate 3' and a compound of Formula (G) to a Suzuki reaction, to obtain an intermediate 4; and subjecting the intermediate 4 and the compound of Formula (E) to a coupling reaction in the presence of a catalyst, to obtain the compound of Formula (I);

where the synthesis route for the compound of Formula (I) is shown below:

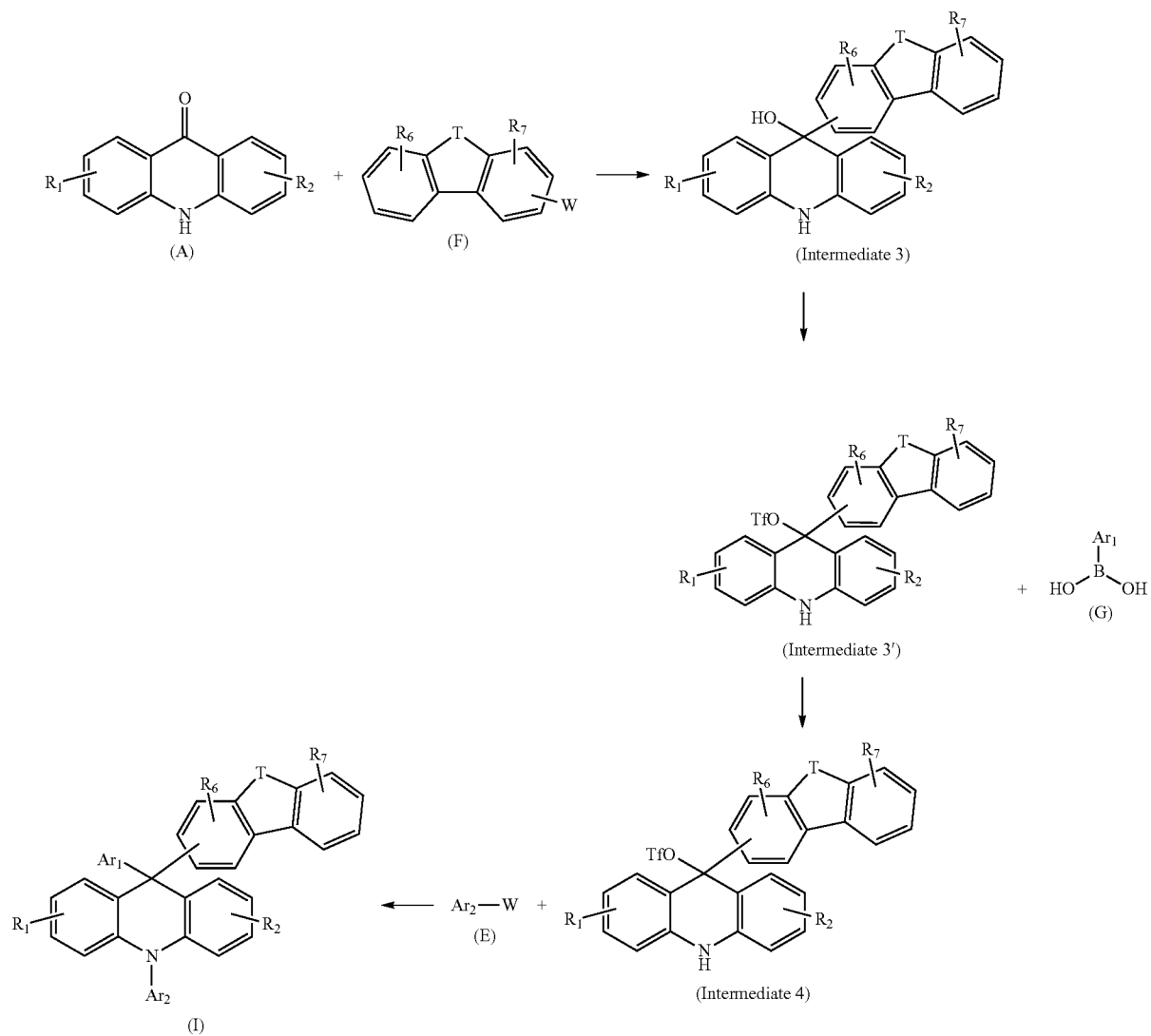

in which W is selected from hydrogen, fluoro, chloro, bromo or iodo, and —OTf is triflate.

The present invention provides use of the 9,10-dihydro-acridine derivative as a hole transport material.

The present invention provides an organic light-emitting device, having at least one functional layer containing the 9,10-dihydro-acridine derivative.

Optionally, in the organic light-emitting device, the functional layer is a hole transport layer and/or an electron blocking layer.

Optionally, in the organic light-emitting device, the functional layer is a light emitting layer.

The technical solution of the invention has the following advantages.

1. The 9,10-dihydro-acridine derivative provided in the present invention has a structure of Formula (I), and the dihydro-acridinyl group is designed to be attached with a dibenzoheterocyclic structure, to form a group having strong electron donating performance. The nitrogen atom in the dihydro-acridinyl group forms an aminium radical under the action of an electric field, thus creating a good hole mobility. At the same time, the compound having a structure of Formula (I) has a suitable HOMO level, and the HOMO level of the hole transport layer formed therewith matches that of the anode and light emitting layer on both sides, thus reducing the potential barrier needed to overcome when holes are injected from the anode to the light emitting layer, increasing the proportion of holes injected into the light emitting layer, and reducing the operating voltage of the OLED device. Compared with the existing triarylamine-based hole transport materials, the HOMO level of the compound having a structure of Formula (I) is optimized to further match the work function of the anode, whereby the potential barrier upon injection of holes from the anode is further reduced, and the effective injection of holes is increased.

In the 9,10-dihydro-acridine derivative of Formula (I), the dihydro-acridinyl group having a high triplet energy level ($T_1$) is linked to a dibenzoheterocyclic ring via a σ bond, in which the dibenzoheterocyclic ring is dibenzofuran, carbazole, or fluorene having a high triplet energy level, to further enhance the triplet energy level of the 9,10-dihydro-acridine derivative. Moreover, the introduction of modifying groups by both of them via a σ bond allows the further adjustment of the triplet energy level ($T_1$) of the compound, and enables the 9,10-dihydro-acridine derivative to have a high triplet energy level ($T_1$), thus facilitating the confining of excitons formed by recombination of electrons and holes in a light emitting region of the light emitting layer of an OLED device, and avoiding the returning of energy from the light emitting layer to the adjacent hole transport layer. Furthermore, the connection mode of the molecule allows for an elevated LUMO level of the 9,10-dihydro-acridine derivative, and thus increases the blocking effect for electrons, and makes the electrons retained in the light emitting layer effectively, thereby increasing the probability of recombination of electrons and holes.

The 9,10-dihydro-acridine derivative of Formula (I) has high glass transition temperature, good film-forming performance, and good thermal stability and morphological stability after film formation, and is not amenable to crystallization during the film formation process or during the operation of the OLED device due to heat generation after film formation, thus improving the performance and service life of the device.

2. In the 9,10-dihydro-acridine derivative provided in the present invention, electron-donating groups (for example, carbazolyl, fluorenyl, and aromatic amine such as diphenylamine, triphenylamine) are introduced by adjusting the $Ar_1$ and $Ar_2$ group in the structure of Formula (I), to further enhance the hole transport performance of the material molecule, adjust the HOMO and LUMO levels of the 9,10-dihydro-acridine derivative, increase the triplet energy level of the 9,10-dihydro-acridine derivative, and improve the hole transport rate of the material molecule. The molecular packing is also reduced by configuring the $Ar_1$ and $Ar_2$ group, to improve the thermal stability of the 9,10-dihydro-acridine derivative.

3. The preparation method of the 9,10-dihydro-acridine derivative provided in the present invention has the advantages of readily available starting materials, mild reaction conditions, and simple operation steps, so a simple and easy-to-implement preparation method is provided for the mass production of the above 9,10-dihydro-acridine derivative.

4. The organic light-emitting device provided in the present invention has at least one functional layer containing the 9,10-dihydro-acridine derivative.

The functional layer is a hole transport layer, the hole transport layer formed with the 9,10-dihydro-acridine derivative as a hole transport material has a HOMO level matching that of the light emitting layer and anode on both sides because the 9,10-dihydro-acridine derivative has a suitable HOMO level and LUMO level, thus reducing the potential barrier needed to overcome when holes are injected from the anode to the light emitting layer, and increasing the proportion of holes injected. The 9,10-dihydro-acridine derivative has good hole transport performance, and can increase the effective transport of holes in the transport layer. Furthermore, the 9,10-dihydro-acridine derivative has a relatively high LUMO level, and can block electrons from diffusing out of the light emitting layer, so as to avoid the loss of electrons and enhance the probability of recombination of electrons and holes, thereby improving the luminescence efficiency of the OLED device. In addition, the 9,10-dihydro-acridine derivative has a high triplet energy level ($T_1$), by which the returning of energy from the light emitting layer to the hole transport layer can be avoided, thereby ensuring the effective luminescence of the device and improving the luminescence efficiency of the device.

The 9,10-dihydro-acridine derivative has high glass transition temperature, good film-forming performance, and good thermal stability, and can prevent the recrystallization in the film layer during the formation of the film layer of the OLED device and during the operation of the device caused by elevated temperature, such that the OLED device can maintain stable working performance, and the service life of the device is prolonged.

The functional layer may also be a light emitting layer. The 9,10-dihydro-acridine derivative can be used as a host material in the light emitting layer alone or as a host material in the light emitting layer by forming an exciplex with a material having electron transporting performance. The 9,10-dihydro-acridine derivative has a high triplet energy level, which can promote the energy transfer of the host material to the guest material, avoid the returning of energy, and improve the luminescence efficiency of the OLED device. The high glass transition temperature of the 9,10-dihydro-acridine derivative gives the light emitting layer formed therefrom good thermal stability, thereby increasing the lifetime of the OLED device.

BRIEF DESCRIPTION OF THE DRAWINGS

In order to more clearly explain the technical solutions in the specific embodiments of the present invention or in the prior art, the drawings used in the description of the specific embodiments or the prior art will be briefly described below. Obviously, the drawings depicted below are merely some embodiments of the present invention, and those skilled in the art can obtain other drawings based on these drawings without any creative efforts.

Figure 1:
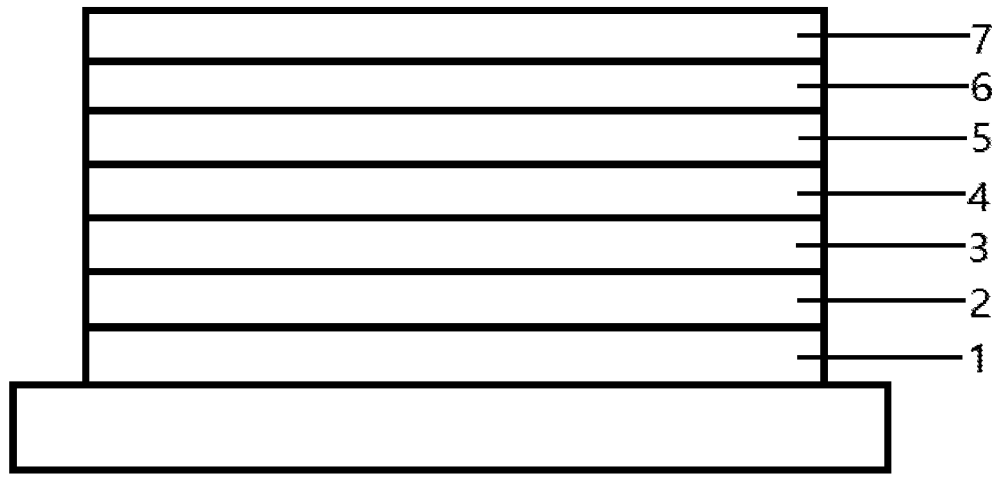
FIG. 1 is a schematic structural view of an organic light-emitting device according to Examples 74 to 83 and Comparative Example 1 of the present invention.

LIST OF REFERENCE NUMERALS 1-anode, 2-hole injection layer, 3-hole transport layer, 4-light emitting layer, 5-electron transport layer, 6-electron injection layer, 7-cathode.

DETAILED DESCRIPTION

The technical solutions of the present invention will be described clearly and fully with reference to the accompanying drawings. Apparently, the embodiments described are some preferred embodiments, rather than all of the embodiments of the present invention. All other embodiments obtained by a person of ordinary skill in the art without creative efforts based on the embodiments of the present invention shall fall within the protection scope of the present invention.

It is to be understood that in the description of the present invention, the terms "first" and "second" are used herein for purposes of description, and are not intended to indicate or imply relative importance.

The present invention can be embodied in many different forms and is not limited to the embodiments described herein. Conversely, these embodiments are provided for the purpose of making the disclosure of the present invention more thorough and comprehensive and conveying the concept of the present invention fully to those skilled in the art, and the scope of the present invention is defined merely by the claims. In the figures, for the sake of clarity, the dimensions and relative dimensions of the layers and regions will be exaggerated. It should be understood that when an element, for example, a layer, is referred to as being "formed" or "disposed" "on" another element, the element may be directly disposed on the other element or an intervening element may be present. Conversely, when an element is referred to as being "directly formed on" or "directly disposed on" another element, no intervening element is present.

Example 1

This example provides a 9,10-dihydro-acridine derivative having a structure of Formula C-1:

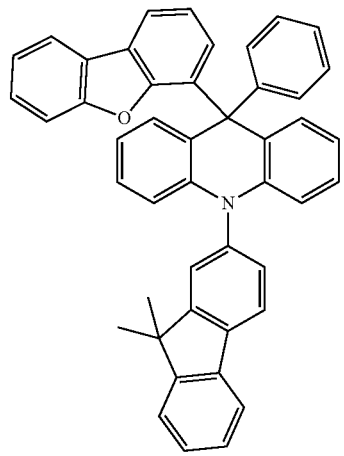

(C-1)

The synthesis route for the 9,10-dihydro-acridine derivative of Formula C-1 is shown below:

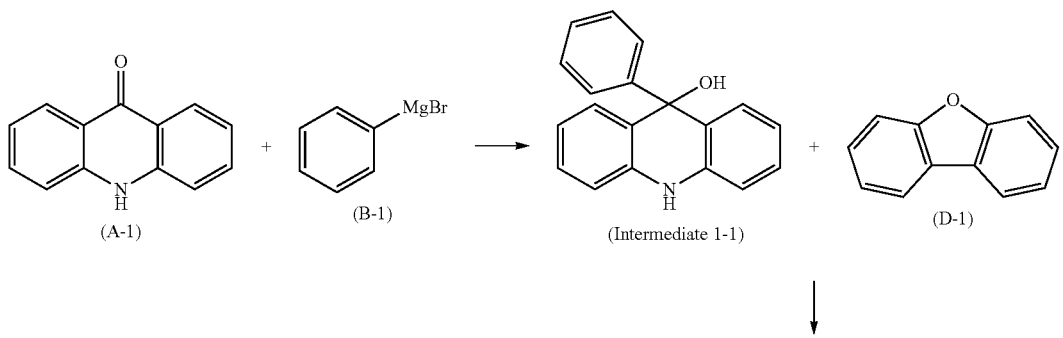

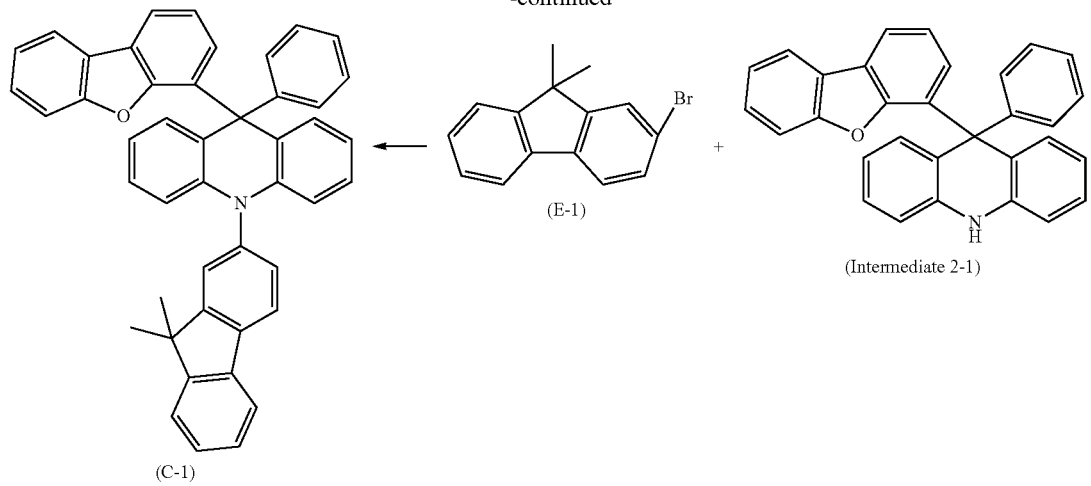

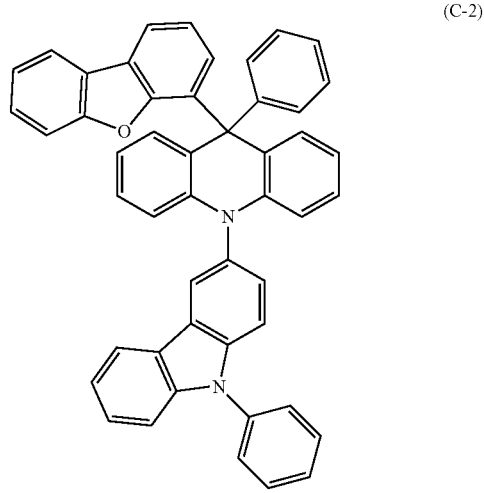 [SMILES: c1ccc(-n2c3ccccc3c3cc(N4c5ccccc5C(c5ccccc5)(c5cccc6c5oc5ccccc56)c5ccccc54)ccc32)cc1]

The method for preparing the 9,10-dihydro-acridine derivative of Formula C-1 comprises specifically the following steps.

(1) Synthesis of Intermediate 1-1

Under nitrogen atmosphere, 9(10H)-acridone (the compound of Formula A-1) (19.5 g, 100 mmol), and tetrahydrofuran (700 mL) were added to a 1 L three-neck flask. A phenyl magnesium bromide (the compound of Formula B-1) solution (110 mL, 1 M) was added at −20° C., reacted at room temperature for 8 hrs, and then quenched by adding an aqueous ammonium chloride solution. The reaction solution was extracted with dichloromethane (3×), and then the solvent was removed by rotary evaporation. The residue was purified by column chromatography on silica gel, to obtain the intermediate 1-1 as a solid (24 g, yield: 88%).

(2) Synthesis of Intermediate 2-1

Under nitrogen atmosphere, the intermediate 1-1 (22.0 g, 80 mmol), dibenzofuran (the compound of Formula D-1) (27 g, 160 mmol), and dichloromethane (600 mL) were added to a 1 L three-neck flask. Eaton's Reagent (1.8 mL, 0.9 M) was added dropwise, reacted at room temperature for 30 min, and then quenched by adding a sodium bicarbonate solution. The reaction solution was extracted with toluene (3×), and then the solvent was removed by rotary evaporation. The residue was purified by column chromatography on silica gel, to obtain the intermediate 2-1 as a solid (13.5 g, yield 40%).

(3) Synthesis of 9,10-dihydro-acridine derivative C-1

Under nitrogen atmosphere, the intermediate 2-1 (8 g, 20 mmol), palladium diacetate (0.13 g, 0.6 mmol), tri-tert-butylphosphine (0.45 g, 2.2 mmol), a compound of Formula E-1 (6.0 g, 22 mmol), sodium-t-butoxide (5.7 g), and toluene (300 mL) were added, reacted at 110° C. for 12 hrs, and then cooled to room temperature. The reaction solution was extracted with chloroform, and then the solvent was removed by rotary evaporation. The residue was purified by column chromatography on silica gel, to obtain the compound C-1 as a solid (10.0 g, yield 82%).

Element analysis: (C46H33NO) calculated: C, 89.73; H, 5.40; N, 2.27; O, 2.60; found: C, 89.71; H, 5.45; N, 2.28; O, 2.57, HRMS (ESI) m/z (M+): calculated: 615.2562; found: 615.2571.

Example 2

This example provides a 9,10-dihydro-acridine derivative having a structure of Formula C-2:

The preparation steps of the 9,10-dihydro-acridine derivative of Formula C-2 were the same as those for the 9,10-dihydro-acridine derivative of Formula C-1 provided in Example 1, except that:

the compound E-1 in Step (3) of Example 1 was replaced by the compound of Formula E-2, and the yield was 80%:

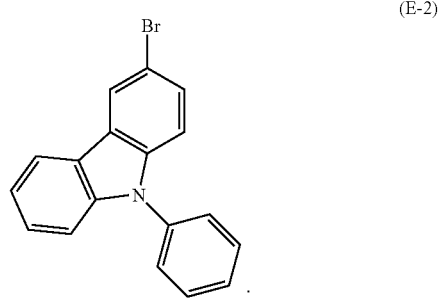 [SMILES: Brc1ccc2c(c1)c1ccccc1n2-c1ccccc1]

Example 3

This example provides a 9,10-dihydro-acridine derivative having a structure of Formula C-3:

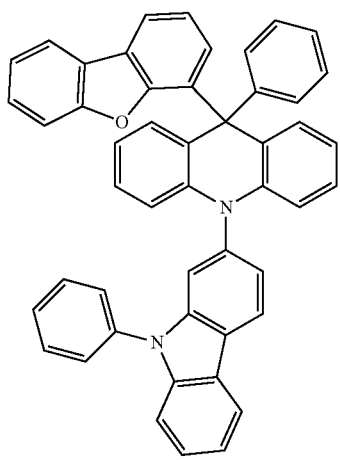

(C-3)

The preparation steps of the 9,10-dihydro-acridine derivative of Formula C-3 were the same as those for the 9,10-dihydro-acridine derivative of Formula C-1 provided in Example 1, except that:

the compound E-1 in Step (3) of Example 1 was replaced by the compound of Formula E-3, and the yield was 78%:

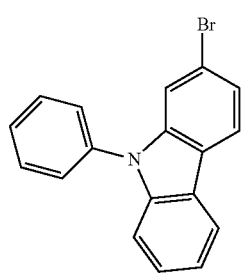

(E-3)

Example 4

This example provides a 9,10-dihydro-acridine derivative having a structure of Formula C-4:

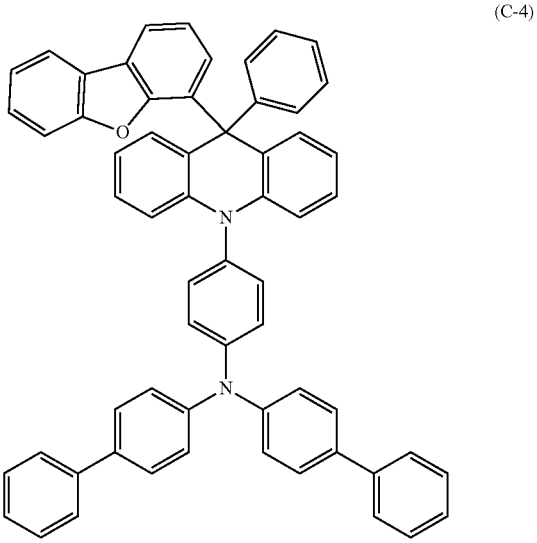 [SMILES: c1ccc(-c2ccc(N(c3ccc(-c4ccccc4)cc3)c3ccc(N4c5ccccc5C(c5ccccc5)(c5cccc6c5oc5ccccc56)c5ccccc54)cc3)cc2)cc1]

(C-4)

The preparation steps of the 9,10-dihydro-acridine derivative of Formula C-4 were the same as those for the 9,10-dihydro-acridine derivative of Formula C-1 provided in Example 1, except that:

the compound E-1 in Step (3) of Example 1 was replaced by the compound of Formula E-4, and the yield was 85%:

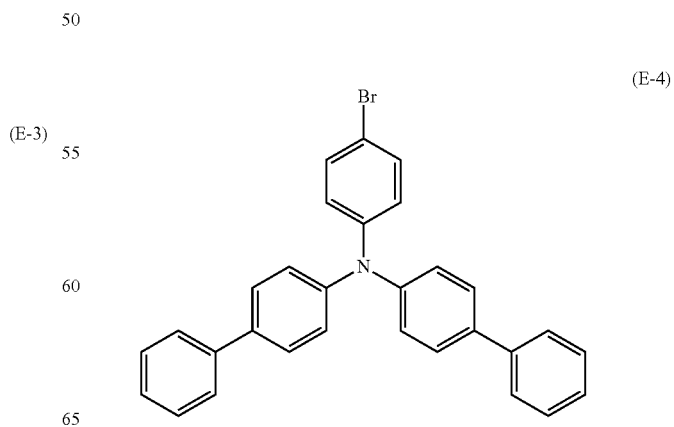

(E-4)

Example 5

This example provides a 9,10-dihydro-acridine derivative having a structure of Formula C-5:

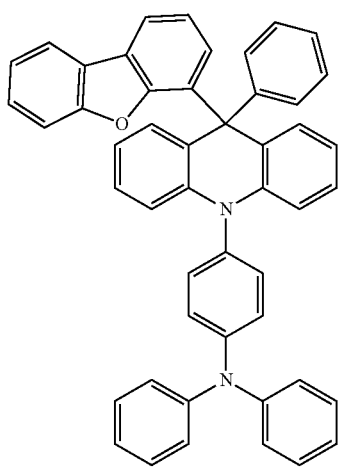

(C-5)

The preparation steps of the 9,10-dihydro-acridine derivative of Formula C-5 were the same as those for the 9,10-dihydro-acridine derivative of Formula C-1 provided in Example 1, except that:

the compound E-1 in Step (3) of Example 1 was replaced by the compound of Formula E-5, and the yield was 84%:

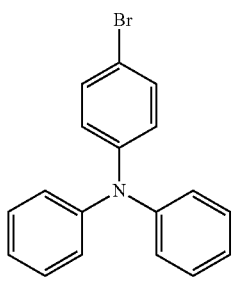

(E-5)

Example 6

This example provides a 9,10-dihydro-acridine derivative having a structure of Formula C-6:

(C-6)

The preparation steps of the 9,10-dihydro-acridine derivative of Formula C-6 were the same as those for the 9,10-dihydro-acridine derivative of Formula C-1 provided in Example 1, except that:

the compound E-1 in Step (3) of Example 1 was replaced by the compound of Formula E-6, and the yield was 84%:

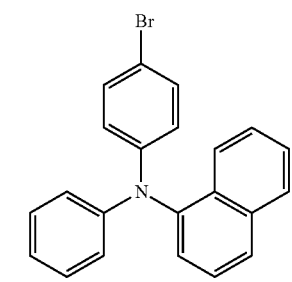

(E-6)

Example 7

This example provides a 9,10-dihydro-acridine derivative having a structure of Formula C-7:

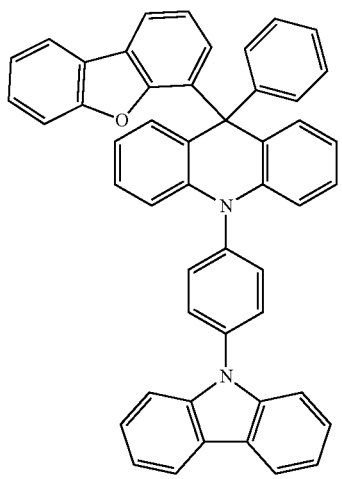

(C-7)

The preparation steps of the 9,10-dihydro-acridine derivative of Formula C-7 were the same as those for the 9,10-dihydro-acridine derivative of Formula C-1 provided in Example 1, except that:

the compound E-1 in Step (3) of Example 1 was replaced by the compound of Formula E-7. The yield was 83%:

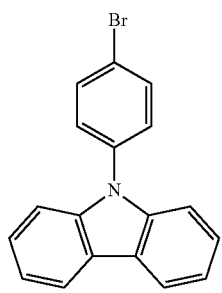

(E-7)

Example 8

This example provides a 9,10-dihydro-acridine derivative having a structure of Formula C-8:

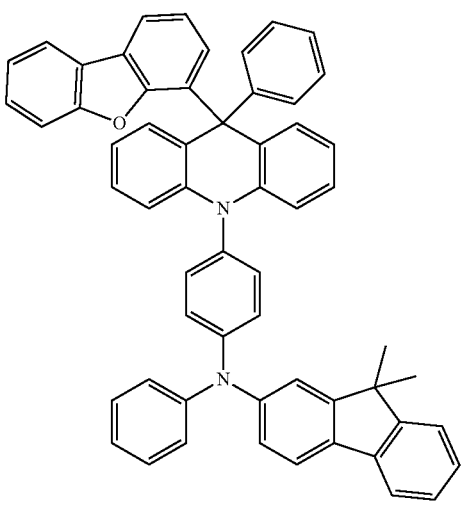

(C-8)

The preparation steps of the 9,10-dihydro-acridine derivative of Formula C-8 were the same as those for the 9,10-dihydro-acridine derivative of Formula C-1 provided in Example 1, except that:

the compound E-1 in Step (3) of Example 1 was replaced by the compound of Formula E-8. The yield was 84%:

(E-8)

Example 9

This example provides a 9,10-dihydro-acridine derivative having a structure of Formula C-9:

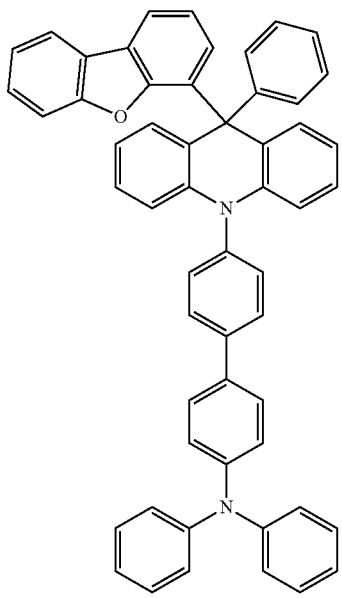

(C-9)

The preparation steps of the 9,10-dihydro-acridine derivative of Formula C-9 were the same as those for the 9,10-dihydro-acridine derivative of Formula C-1 provided in Example 1, except that:

the compound E-1 in Step (3) of Example 1 was replaced by the compound of Formula E-9. The yield was 85%:

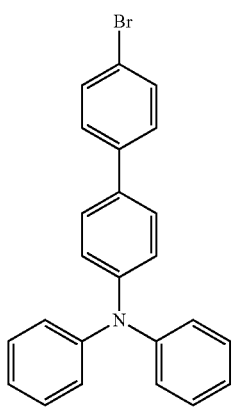

(E-9)

Example 10

This example provides a 9,10-dihydro-acridine derivative having a structure of Formula C-10:

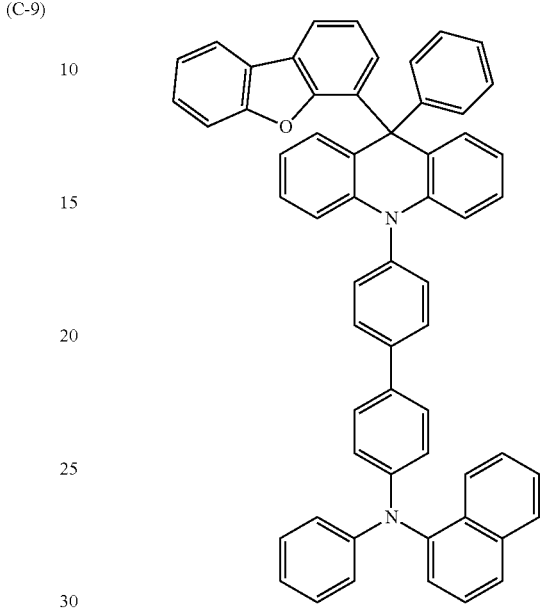

(C-10)

The preparation steps of the 9,10-dihydro-acridine derivative of Formula C-10 were the same as those for the 9,10-dihydro-acridine derivative of Formula C-1 provided in Example 1, except that:

the compound E-1 in Step (3) of Example 1 was replaced by the compound of Formula E-10. The yield was 84%:

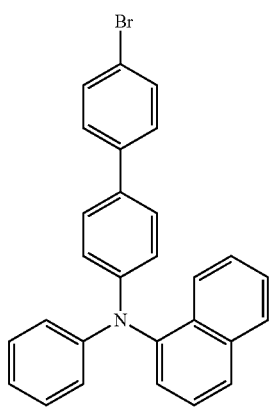

(E-10)

Example 11

This example provides a 9,10-dihydro-acridine derivative having a structure of Formula C-11:

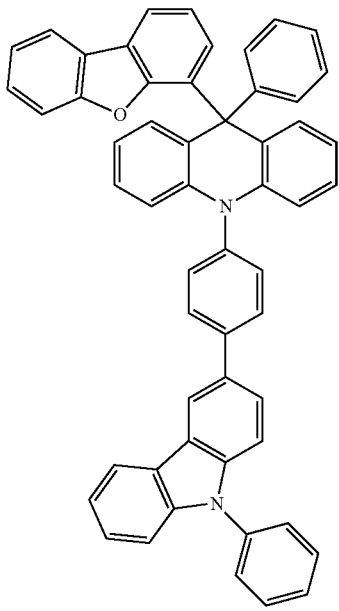

(C-11)

The preparation steps of the 9,10-dihydro-acridine derivative of Formula C-11 were the same as those for the 9,10-dihydro-acridine derivative of Formula C-1 provided in Example 1, except that:

the compound E-1 in Step (3) of Example 1 was replaced by the compound of Formula E-11. The yield was 83%:

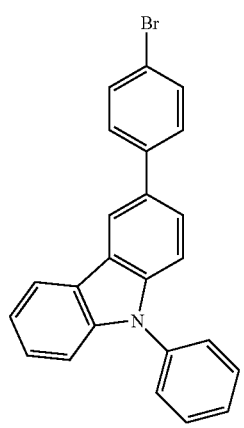

(E-11)

Example 12

This example provides a 9,10-dihydro-acridine derivative having a structure of Formula C-12:

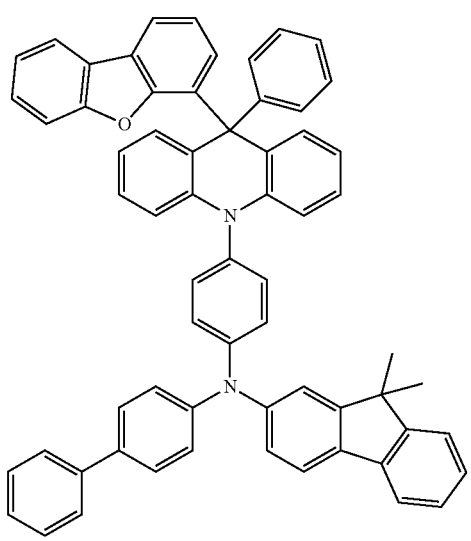

(C-12)

The preparation steps of the 9,10-dihydro-acridine derivative of Formula C-12 were the same as those for the 9,10-dihydro-acridine derivative of Formula C-1 provided in Example 1, except that:

the compound E-1 in Step (3) of Example 1 was replaced by the compound of Formula E-12. The yield was 85%:

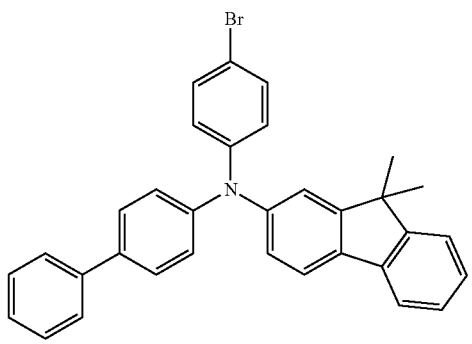

(E-12)

Example 13
This example provides a 9,10-dihydro-acridine derivative having a structure of Formula C-13:
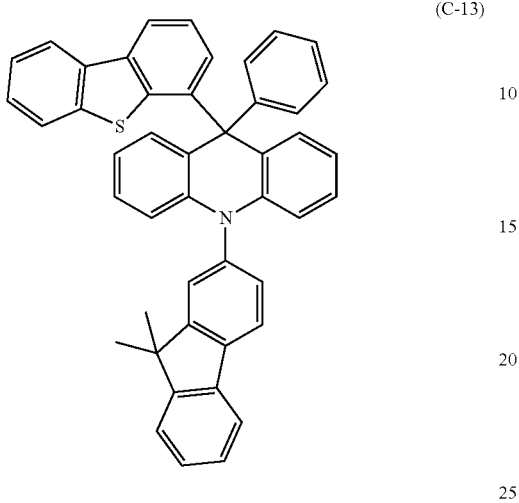
The synthesis route for the 9,10-dihydro-acridine derivative of Formula C-13 is shown below:
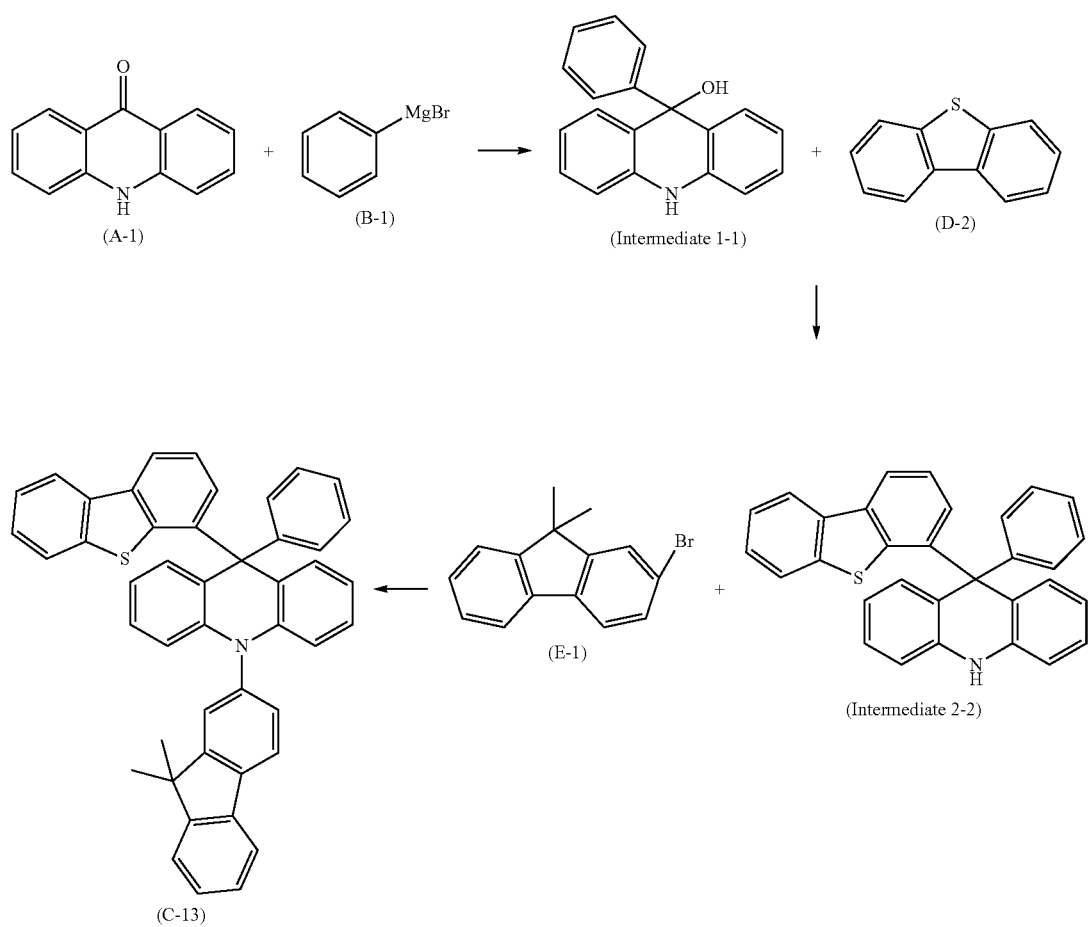

The method for preparing the 9,10-dihydro-acridine derivative of Formula C-13 comprises specifically the following steps.

(1) Synthesis of Intermediate 1-1

Under nitrogen atmosphere, 9(10H)-acridone (the compound of Formula A-1) (19.5 g, 100 mmol), and tetrahydrofuran (700 mL) were added to a 1 L three-neck flask. A phenyl magnesium bromide (the compound of Formula B-1) solution (110 mL, 1 M) was added at −20° C., reacted at room temperature for 8 hrs, and then quenched by adding an aqueous ammonium chloride solution. The reaction solution was extracted with dichloromethane (3×), and then the solvent was removed by rotary evaporation. The residue was purified by column chromatography on silica gel, to obtain the intermediate 1-1 as a solid (24 g, yield: 88%).

(2) Synthesis of Intermediate 2-2

Under nitrogen atmosphere, the intermediate 1-1 (22.0 g, 80 mmol), dibenzothiophene (the compound of Formula D-2) (29 g, 160 mmol), and dichloromethane (600 mL) were added to a 1 L three-neck flask. Eaton's Reagent (1.8 mL, 0.9 M) was added dropwise, reacted at room temperature for 30 min, and then quenched by adding a sodium bicarbonate solution. The reaction solution was extracted with toluene (3×), and then the solvent was removed by rotary evaporation. The residue was purified by column chromatography on silica gel, to obtain the intermediate 2-2 as a solid (13.3 g, yield 38%).

(3) Synthesis of 9,10-dihydro-acridine derivative C-13

Under nitrogen atmosphere, the intermediate 2-2 (8.8 g, 20 mmol), palladium diacetate (0.13 g, 0.6 mmol), tri-tert-butylphosphine (0.45 g, 2.2 mmol), a compound of Formula E-1 (6.0 g 22 mmol), sodium-t-butoxide (5.7 g), and toluene (300 mL) were added, reacted at 110° C. for 12 hrs, and then cooled to room temperature. The reaction solution was extracted with chloroform, and then the solvent was removed by rotary evaporation. The residue was purified by column chromatography on silica gel, to obtain the compound C-13 as a solid (10.7 g, yield 85%).

Element analysis: (C46H33NS) calculated: C, 87.44; H, 5.26; N, 2.22; S, 5.07; found: C, 87.41; H, 5.29; N, 2.20; S, 5.03, HRMS (ESI) m/z (M+): calculated: 631.2334; found: 631.2347.

Example 14

This example provides a 9,10-dihydro-acridine derivative having a structure of Formula C-14:

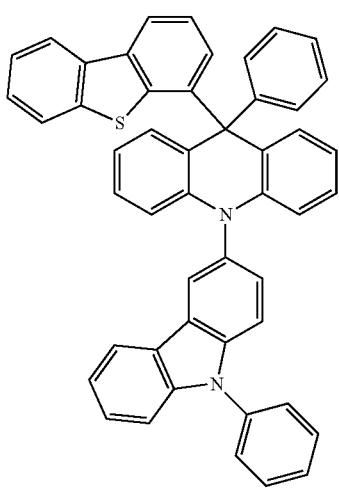

(C-14)

The preparation steps of the 9,10-dihydro-acridine derivative of Formula C-14 were the same as those for the 9,10-dihydro-acridine derivative of Formula C-13 provided in Example 13, except that:

the compound E-1 in Step (3) of Example 13 was replaced by the compound of Formula E-2, and the yield was 82%:

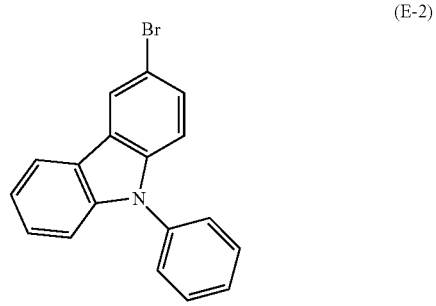 [SMILES: Brc1ccc2c(c1)c1ccccc1n2-c1ccccc1]

(E-2)

Example 15

This example provides a 9,10-dihydro-acridine derivative having a structure of Formula C-15:

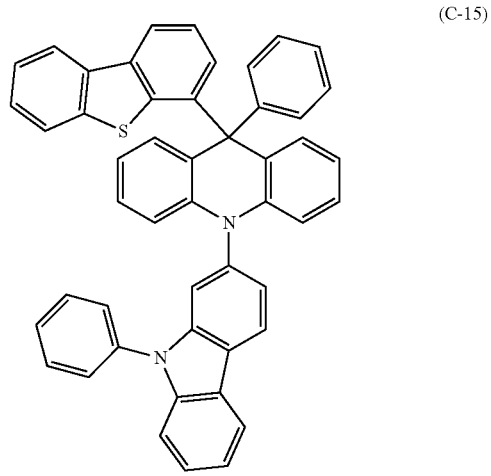 [SMILES: c1ccc(-n2c3ccccc3c3ccc(N4c5ccccc5C(c5ccccc5)(c5cccc6c5sc5ccccc56)c5ccccc54)cc32)cc1]

(C-15)

The preparation steps of the 9,10-dihydro-acridine derivative of Formula C-15 were the same as those for the 9,10-dihydro-acridine derivative of Formula C-13 provided in Example 13, except that:

the compound E-1 in Step (3) of Example 13 was replaced by the compound of Formula E-3, and the yield was 83%:

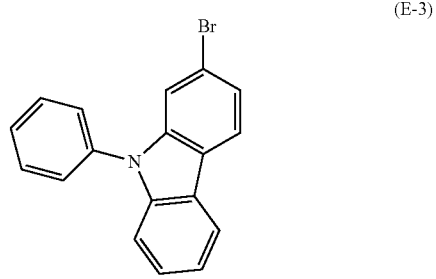 [SMILES: Brc1ccc2c3ccccc3n(-c3ccccc3)c2c1]

(E-3)

Example 16

This example provides a 9,10-dihydro-acridine derivative having a structure of Formula C-16:

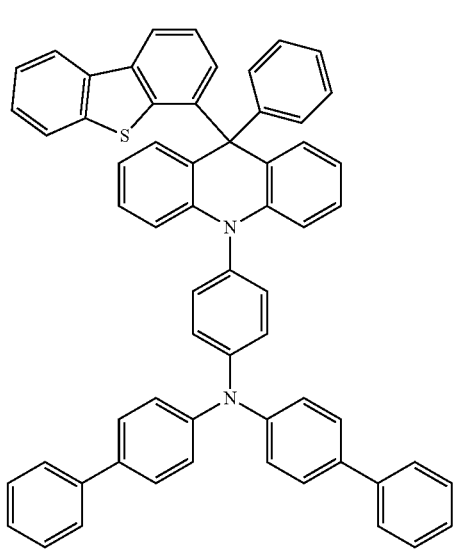
(C-16)

The preparation steps of the 9,10-dihydro-acridine derivative of Formula C-16 were the same as those for the 9,10-dihydro-acridine derivative of Formula C-13 provided in Example 13, except that:

the compound E-1 in Step (3) of Example 13 was replaced by the compound of Formula E-4, and the yield was 85%:

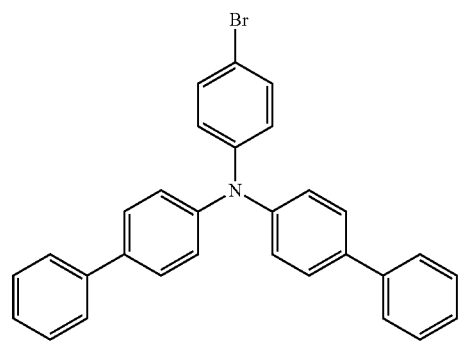
(E-4)

Example 17

This example provides a 9,10-dihydro-acridine derivative having a structure of Formula C-17:

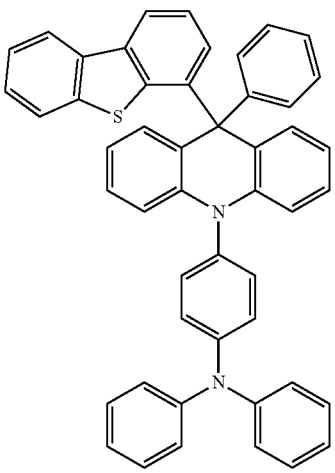
(C-17)

The preparation steps of the 9,10-dihydro-acridine derivative of Formula C-17 were the same as those for the 9,10-dihydro-acridine derivative of Formula C-13 provided in Example 13, except that:

the compound E-1 in Step (3) of Example 13 was replaced by the compound of Formula E-5, and the yield was 87%:

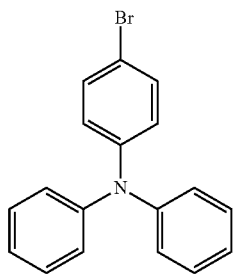
(E-5)

Example 18

This example provides a 9,10-dihydro-acridine derivative having a structure of Formula C-18:

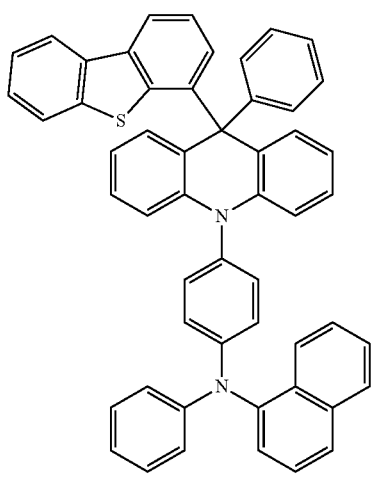

(C-18)

The preparation steps of the 9,10-dihydro-acridine derivative of Formula C-18 were the same as those for the 9,10-dihydro-acridine derivative of Formula C-13 provided in Example 13, except that:

the compound E-1 in Step (3) of Example 13 was replaced by the compound of Formula E-6, and the yield was 83%:

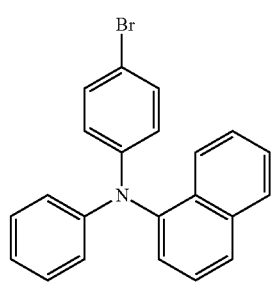

(E-6)

Example 19

This example provides a 9,10-dihydro-acridine derivative having a structure of Formula C-19:

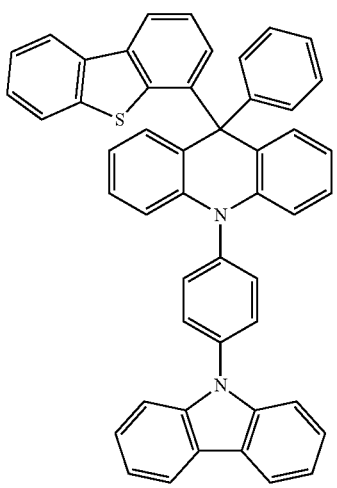

(C-19)

The preparation steps of the 9,10-dihydro-acridine derivative of Formula C-19 were the same as those for the 9,10-dihydro-acridine derivative of Formula C-13 provided in Example 13, except that:

the compound E-1 in Step (3) of Example 13 was replaced by the compound of Formula E-7. The yield was 83%:

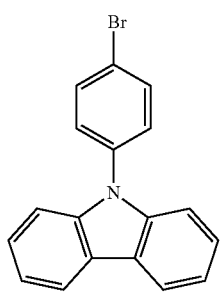

(E-7)

Example 20

This example provides a 9,10-dihydro-acridine derivative having a structure of Formula C-20:

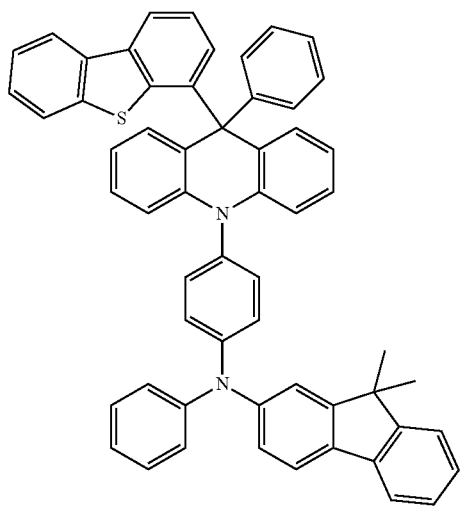

(C-20)

The preparation steps of the 9,10-dihydro-acridine derivative of Formula C-20 were the same as those for the 9,10-dihydro-acridine derivative of Formula C-13 provided in Example 13, except that:

the compound E-1 in Step (3) of Example 13 was replaced by the compound of Formula E-8. The yield was 85%:

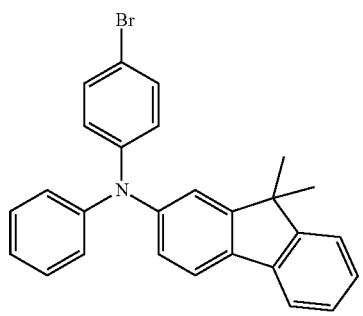

(E-8)

Example 21

This example provides a 9,10-dihydro-acridine derivative having a structure of Formula C-21:

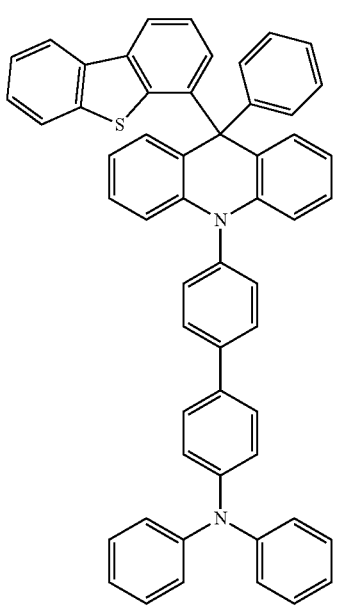

(C-21)

The preparation steps of the 9,10-dihydro-acridine derivative of Formula C-21 were the same as those for the 9,10-dihydro-acridine derivative of Formula C-13 provided in Example 13, except that:

the compound E-1 in Step (3) of Example 13 was replaced by the compound of Formula E-9. The yield was 81%:

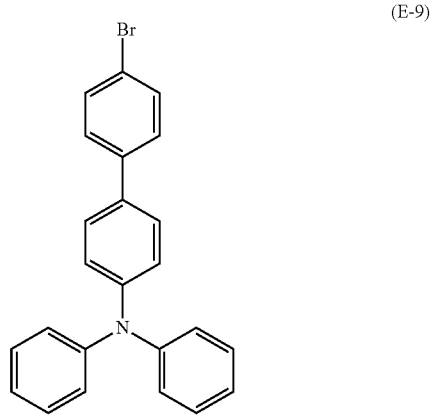 [SMILES: Brc1ccc(-c2ccc(N(c3ccccc3)c3ccccc3)cc2)cc1]

(E-9)

Example 22

This example provides a 9,10-dihydro-acridine derivative having a structure of Formula C-22:

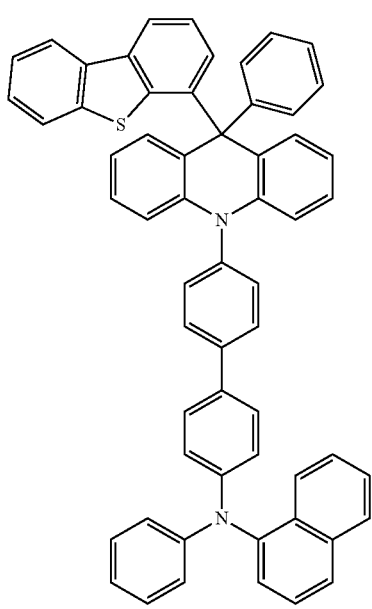

(C-22)

The preparation steps of the 9,10-dihydro-acridine derivative of Formula C-22 were the same as those for the 9,10-dihydro-acridine derivative of Formula C-13 provided in Example 13, except that:

the compound E-1 in Step (3) of Example 13 was replaced by the compound of Formula E-10. The yield was 82%:

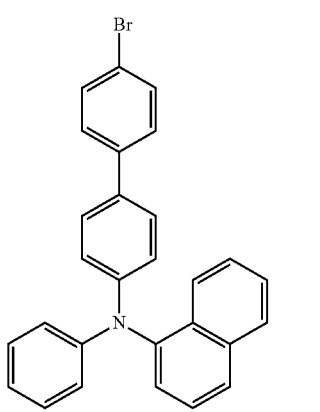

(E-10)

Example 23

This example provides a 9,10-dihydro-acridine derivative having a structure of Formula C-23:

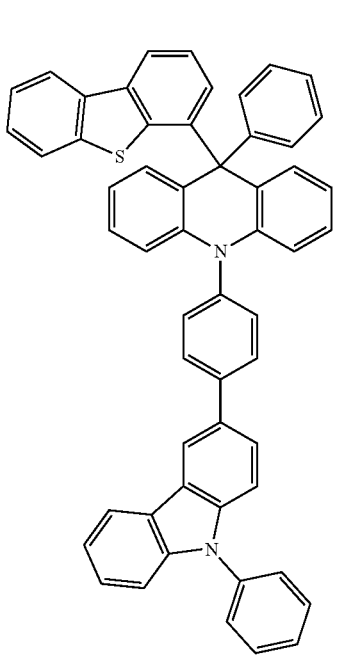

(C-23)

The preparation steps of the 9,10-dihydro-acridine derivative of Formula C-23 were the same as those for the 9,10-dihydro-acridine derivative of Formula C-13 provided in Example 13, except that:

the compound E-1 in Step (3) of Example 13 was replaced by the compound of Formula E-11. The yield was 85%:

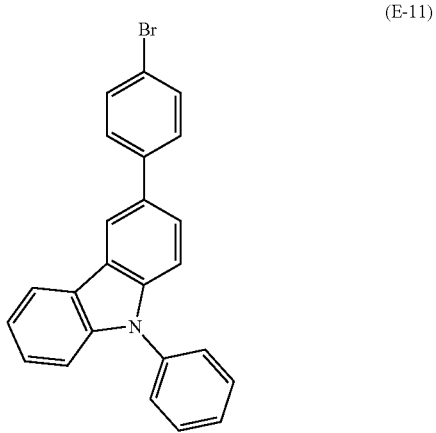 [SMILES: Brc1ccc(-c2ccc3c(c2)c2ccccc2n3-c2ccccc2)cc1]

(E-11)

Example 24

This example provides a 9,10-dihydro-acridine derivative having a structure of Formula C-24:

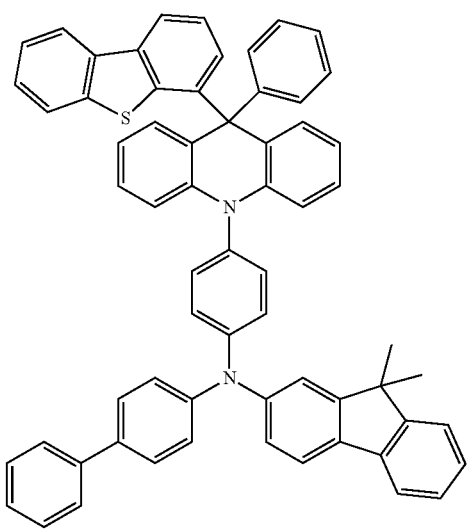

(C-24)

The preparation steps of the 9,10-dihydro-acridine derivative of Formula C-24 were the same as those for the 9,10-dihydro-acridine derivative of Formula C-13 provided in Example 13, except that:

the compound E-1 in Step (3) of Example 13 was replaced by the compound of Formula E-12. The yield was 83%:

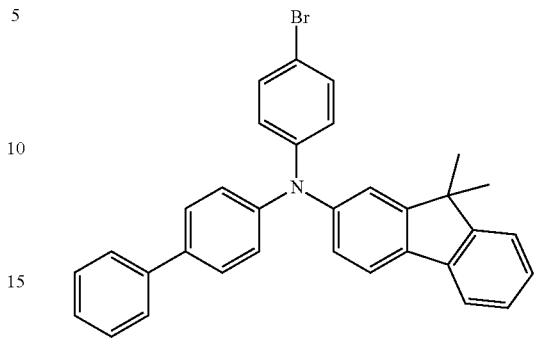

(E-12)

Example 25

This example provides a 9,10-dihydro-acridine derivative having a structure of Formula C-25:

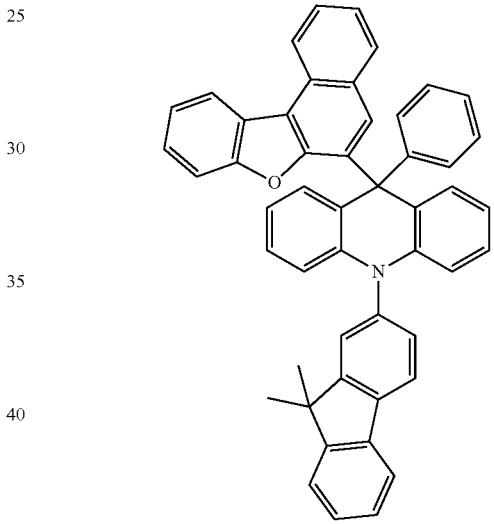

(C-25)

The synthesis route for the 9,10-dihydro-acridine derivative of Formula C-25 is shown below:

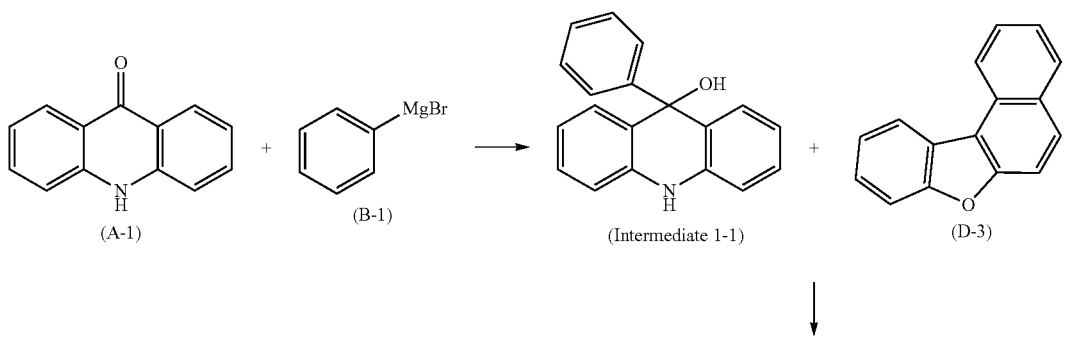

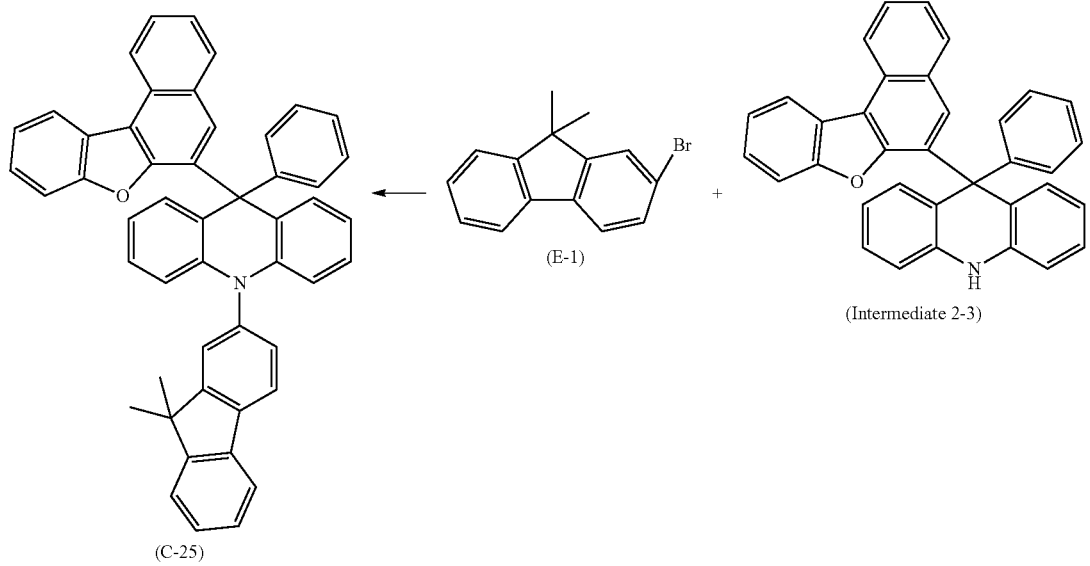

The method for preparing the 9,10-dihydro-acridine derivative of Formula C-25 comprises specifically the following steps.

(1) Synthesis of Intermediate 1-1

Under nitrogen atmosphere, 9(10H)-acridone (the compound of Formula A-1) (19.5 g, 100 mmol), and tetrahydrofuran (700 mL) were added to a 1 L three-neck flask. A phenyl magnesium bromide (the compound of Formula B-1) solution (110 mL, 1 M) was added at −20° C., reacted at room temperature for 8 hrs, and then quenched by adding an aqueous ammonium chloride solution. The reaction solution was extracted with dichloromethane (3×), and then the solvent was removed by rotary evaporation. The residue was purified by column chromatography on silica gel, to obtain the intermediate 1-1 as a solid (24 g, yield: 88%).

(2) Synthesis of Intermediate 2-3

Under nitrogen atmosphere, the intermediate 1-1 (22.0 g, 80 mmol), a compound of Formula D-3 (35 g, 160 mmol), and dichloromethane (1000 mL) were added to a 2 L three-neck flask. Eaton's Reagent (1.8 mL, 0.9 M) was added dropwise, reacted at room temperature for 30 min, and then quenched by adding a sodium bicarbonate solution. The reaction solution was extracted with toluene (3×), and then the solvent was removed by rotary evaporation. The residue was purified by column chromatography on silica gel, to obtain the intermediate 2-3 as a solid (12.8 g, yield 34%).

(3) Synthesis of 9,10-dihydro-acridine derivative C-25

Under nitrogen atmosphere, the intermediate 2-3 (9.5 g, 20 mmol), palladium diacetate (0.13 g, 0.6 mmol), tri-tert-butylphosphine (0.45 g, 2.2 mmol), a compound of Formula E-1 (6.0 g, 22 mmol), sodium-t-butoxide (5.7 g), and toluene (300 mL) were added, reacted at 110° C. for 12 hrs, and then cooled to room temperature. The reaction solution was extracted with chloroform, and then the solvent was removed by rotary evaporation. The residue was purified by column chromatography on silica gel, to obtain the compound C-25 as a solid (11.3 g, yield 85%).

Element analysis: (C50H35NO) calculated: C, 90.19; H, 5.30; N, 2.10; O, 2.40; found: C, 90.13; H, 5.33; N, 2.15; O, 2.43, HRMS (ESI) m/z (M+): calculated: 665.2719; found: 665.2707.

Example 26

This example provides a 9,10-dihydro-acridine derivative having a structure of Formula C-26:

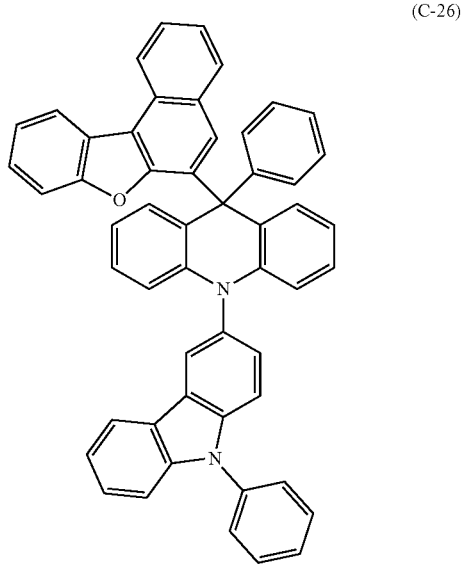 [SMILES: c1ccc(-n2c3ccccc3c3cc(N4c5ccccc5C(c5ccccc5)(c5cc6ccccc6c6c5oc5ccccc56)c5ccccc54)ccc32)cc1]

(C-26)

The preparation steps of the 9,10-dihydro-acridine derivative of Formula C-26 were the same as those for the 9,10-dihydro-acridine derivative of Formula C-25 provided in Example 25, except that:

the compound E-1 in Step (3) of Example 25 was replaced by the compound of Formula E-2, and the yield was 81%:

(E-2)

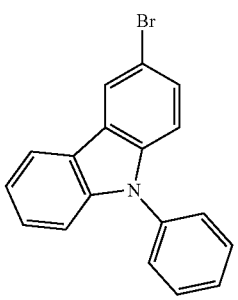

Example 27

This example provides a 9,10-dihydro-acridine derivative having a structure of Formula C-27:

(C-27)

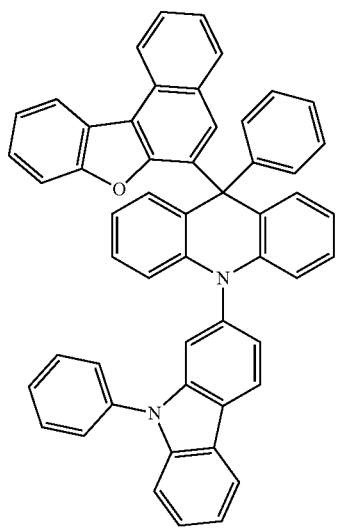

The preparation steps of the 9,10-dihydro-acridine derivative of Formula C-27 were the same as those for the 9,10-dihydro-acridine derivative of Formula C-25 provided in Example 25, except that:

the compound E-1 in Step (3) of Example 25 was replaced by the compound of Formula E-3, and the yield was 84%:

(E-3)

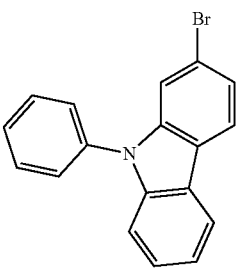

Example 28

This example provides a 9,10-dihydro-acridine derivative having a structure of Formula C-28:

(C-28)

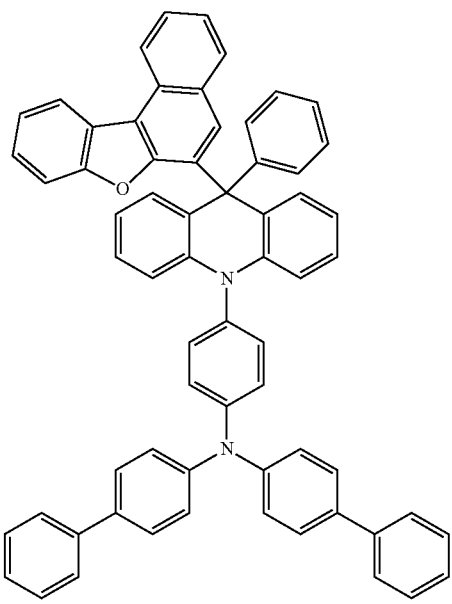

The preparation steps of the 9,10-dihydro-acridine derivative of Formula C-28 were the same as those for the 9,10-dihydro-acridine derivative of Formula C-25 provided in Example 25, except that:

the compound E-1 in Step (3) of Example 25 was replaced by the compound of Formula E-4, and the yield was 85%:

(E-4)

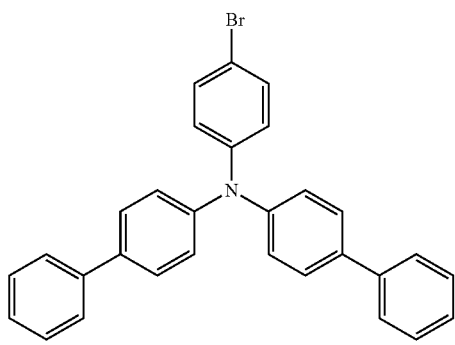

Example 29

This example provides a 9,10-dihydro-acridine derivative having a structure of Formula C-29:

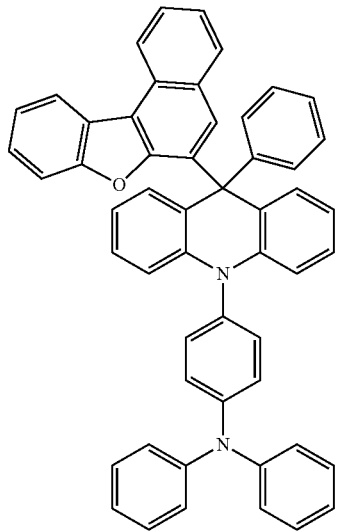

(C-29)

The preparation steps of the 9,10-dihydro-acridine derivative of Formula C-29 were the same as those for the 9,10-dihydro-acridine derivative of Formula C-25 provided in Example 25, except that:

the compound E-1 in Step (3) of Example 25 was replaced by the compound of Formula E-5, and the yield was 86%:

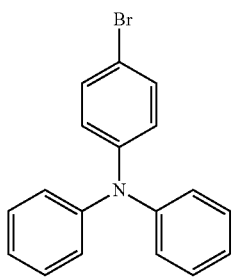

(E-5)

Example 30

This example provides a 9,10-dihydro-acridine derivative having a structure of Formula C-30:

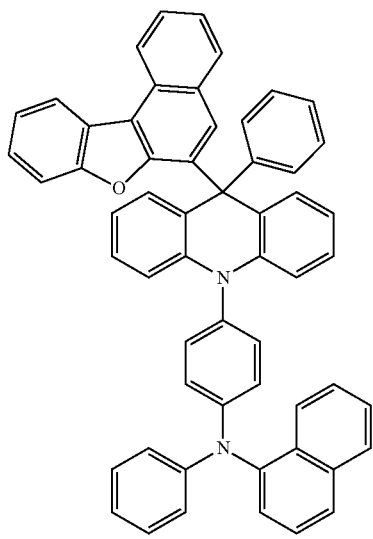

(C-30)

The preparation steps of the 9,10-dihydro-acridine derivative of Formula C-30 were the same as those for the 9,10-dihydro-acridine derivative of Formula C-25 provided in Example 25, except that:

the compound E-1 in Step (3) of Example 25 was replaced by the compound of Formula E-6, and the yield was 82%:

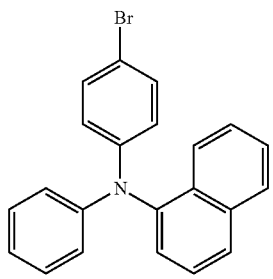

(E-6)

Example 31

This example provides a 9,10-dihydro-acridine derivative having a structure of Formula C-31:

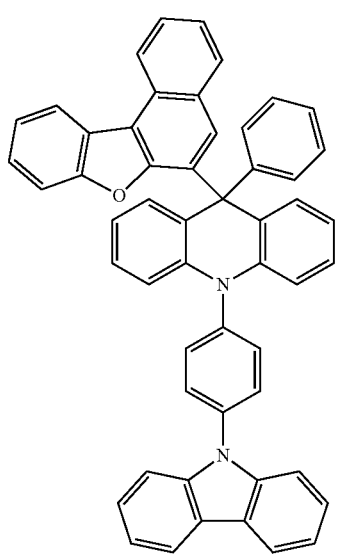

(C-31)

The preparation steps of the 9,10-dihydro-acridine derivative of Formula C-31 were the same as those for the 9,10-dihydro-acridine derivative of Formula C-25 provided in Example 25, except that:

the compound E-1 in Step (3) of Example 25 was replaced by the compound of Formula E-7. The yield was 85%:

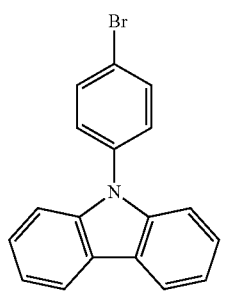

(E-7)

Example 32

This example provides a 9,10-dihydro-acridine derivative having a structure of Formula C-32:

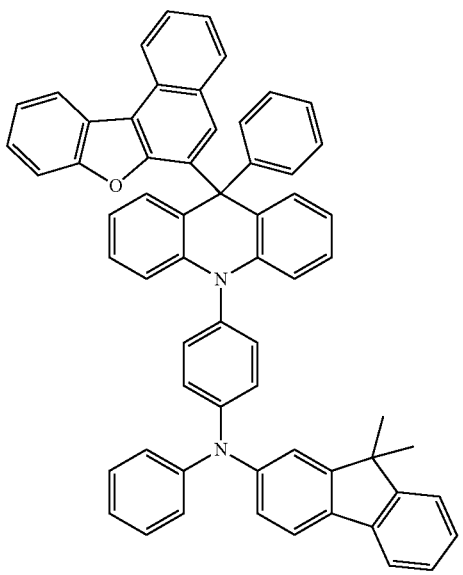

(C-32)

The preparation steps of the 9,10-dihydro-acridine derivative of Formula C-32 were the same as those for the 9,10-dihydro-acridine derivative of Formula C-25 provided in Example 25, except that:

the compound E-1 in Step (3) of Example 25 was replaced by the compound of Formula E-8. The yield was 84%:

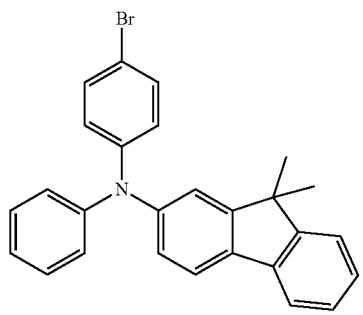

(E-8)

Example 33

This example provides a 9,10-dihydro-acridine derivative having a structure of Formula C-33:

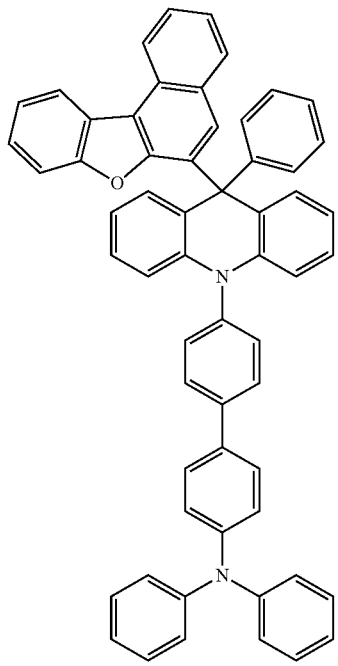

(C-33)

The preparation steps of the 9,10-dihydro-acridine derivative of Formula C-33 were the same as those for the 9,10-dihydro-acridine derivative of Formula C-25 provided in Example 25, except that:

the compound E-1 in Step (3) of Example 25 was replaced by the compound of Formula E-9. The yield was 84%:

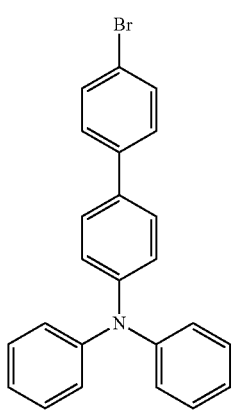

(E-9)

Example 34

This example provides a 9,10-dihydro-acridine derivative having a structure of Formula C-34:

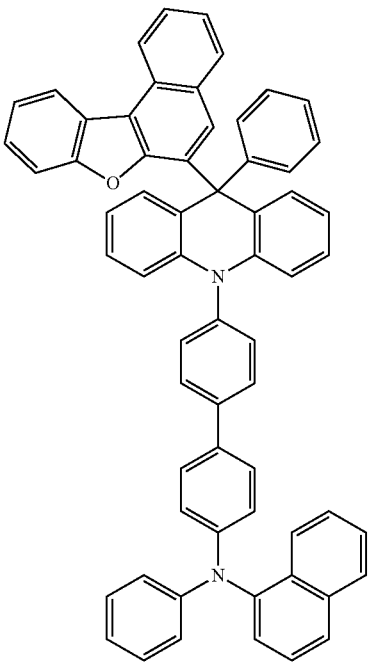

(C-34)

The preparation steps of the 9,10-dihydro-acridine derivative of Formula C-34 were the same as those for the 9,10-dihydro-acridine derivative of Formula C-25 provided in Example 25, except that:

the compound E-1 in Step (3) of Example 25 was replaced by the compound of Formula E-10. The yield was 82%:

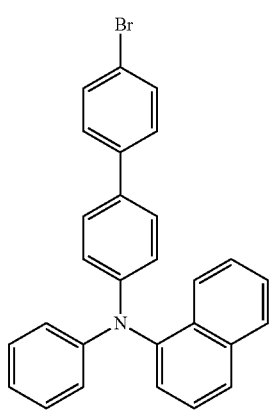

(E-10)

Example 35

This example provides a 9,10-dihydro-acridine derivative having a structure of Formula C-35:

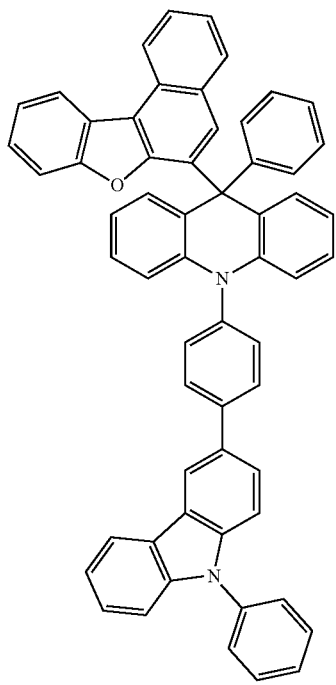

(C-35)

The preparation steps of the 9,10-dihydro-acridine derivative of Formula C-35 were the same as those for the 9,10-dihydro-acridine derivative of Formula C-25 provided in Example 25, except that:

the compound E-1 in Step (3) of Example 25 was replaced by the compound of Formula E-11. The yield was 83%:

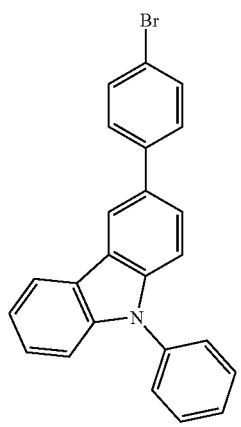

(E-11)

Example 36

This example provides a 9,10-dihydro-acridine derivative having a structure of Formula C-36:

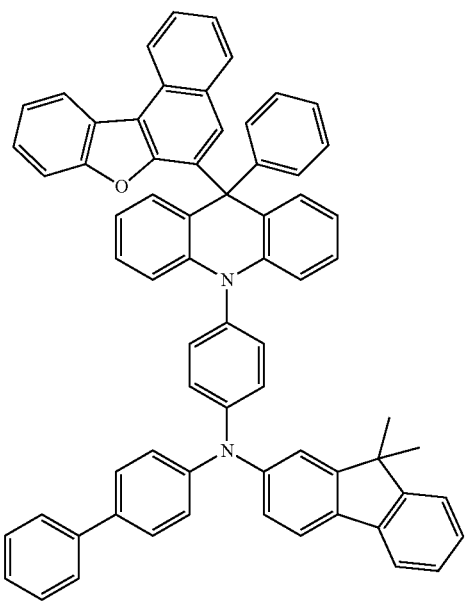

(C-36)

The preparation steps of the 9,10-dihydro-acridine derivative of Formula C-36 were the same as those for the 9,10-dihydro-acridine derivative of Formula C-25 provided in Example 25, except that:

the compound E-1 in Step (3) of Example 25 was replaced by the compound of Formula E-12. The yield was 84%:

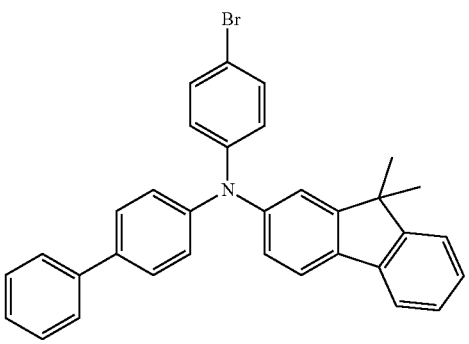

(E-12)

Example 37
This example provides a 9,10-dihydro-acridine derivative having a structure of Formula C-49:
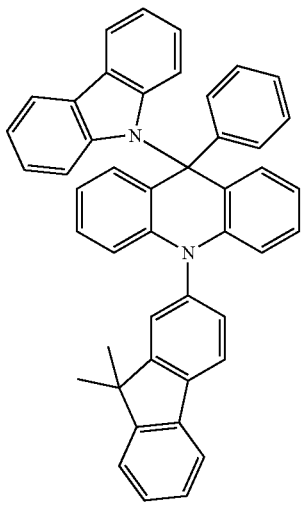
(C-49)
The synthesis route for the 9,10-dihydro-acridine derivative of Formula C-49 is shown below:
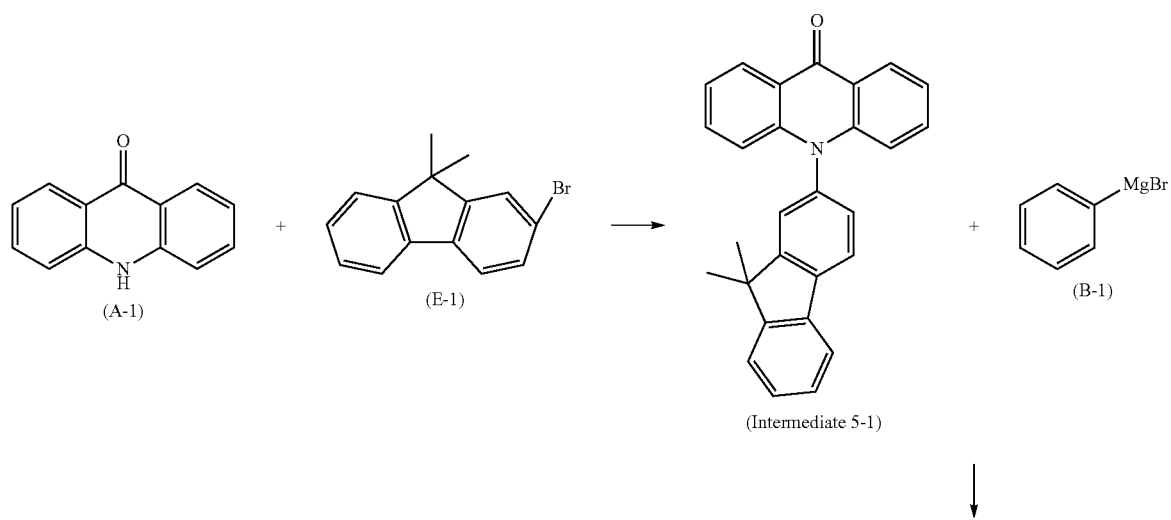

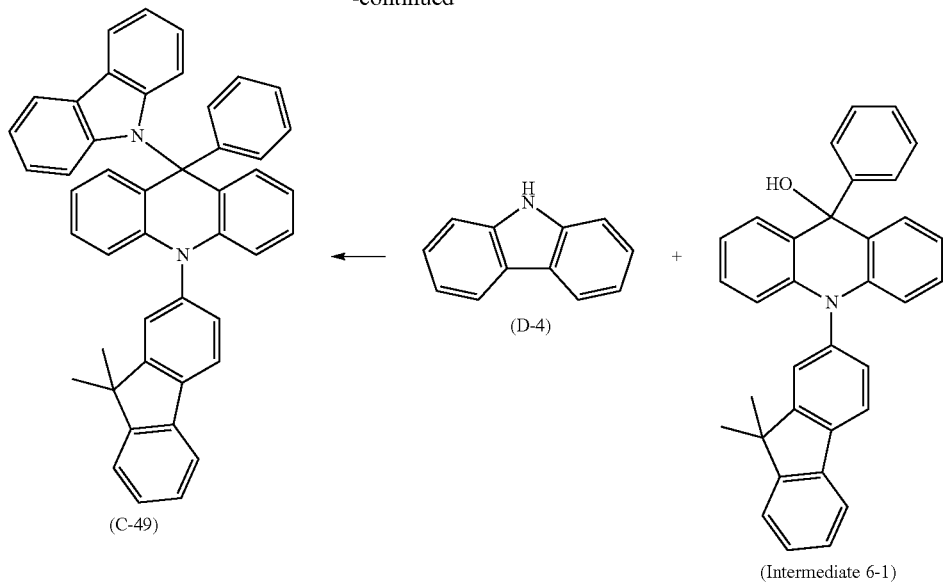

The method for preparing the 9,10-dihydro-acridine derivative of Formula C-49 comprises specifically the following steps.

(1) Synthesis of Intermediate 5-1

Under nitrogen atmosphere, 9(10H)-acridone (the compound of Formula A-1) (19.5 g, 100 mmol), palladium diacetate (0.65 g, 3 mmol), tri-tert-butylphosphine (2.25 g, 11.0 mmol), the compound of Formula E-1 (30.0 g, 110 mmol), sodium-t-butoxide (28.5 g), and toluene (100 mL) were added, reacted at 110° C. for 12 hrs, and then cooled to room temperature. The reaction solution was extracted with chloroform, and then the solvent was removed by rotary evaporation. The residue was purified by column chromatography on silica gel, to obtain the intermediate 5-1 as a solid (33.7 g, yield 87%).

(2) Synthesis of Intermediate 6-1

Under nitrogen atmosphere, the intermediate 5-1 (31 g, 80 mmol) and tetrahydrofuran (800 mL) were added. A phenyl magnesium bromide (the compound of Formula B-1) solution (88 mL, 1 M) was added at −20° C., reacted at room temperature for 8 hrs, and then quenched by adding an aqueous ammonium chloride solution. The reaction solution was extracted with dichloromethane (3×), and then the solvent was removed by rotary evaporation. The residue was purified by column chromatography on silica gel, to obtain the intermediate 6-1 as a solid (29.1 g, yield: 78%).

(3) Synthesis of 9,10-dihydro-acridine derivative C-49

Under nitrogen atmosphere, the intermediate 6-1 (23.5 g, 50 mmol), tetrahydrofuran (1000 mL), triphenylphosphine (19 g, 150 mmol), carbazole (the compound of Formula D-4) (10 g, 60 mmol), and DEAD (diethyl azodiformate) (10.5 g, 60 mmol) were added, and reacted at room temperature for 12 hrs. The reaction solution was extracted with dichloromethane (3×), and then the solvent was removed by rotary evaporation. The residue was purified by column chromatography on silica gel, to obtain the compound C-49 as a solid (20.1 g, yield: 66%).

Element analysis: (C46H34N2) calculated: C, 89.87; H, 5.57; N, 4.56; found: C, 89.91; H, 5.59; N, 4.51; HRMS (ESI) m/z (M+): calculated: 614.2722; found: 614.2731.

Example 38

This example provides a 9,10-dihydro-acridine derivative having a structure of Formula C-50:

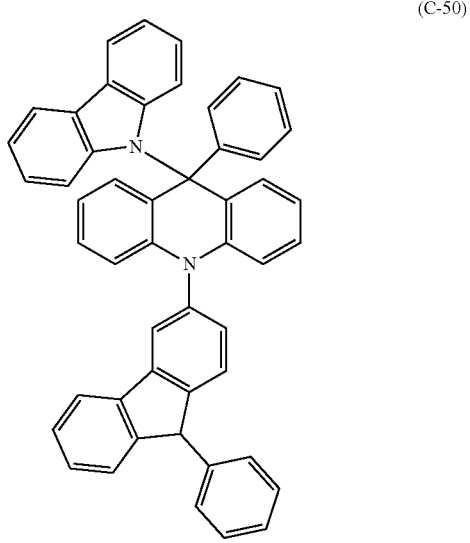 [SMILES: c1ccc(C2c3ccccc3-c3cc(N4c5ccccc5C(c5ccccc5)(n5c6ccccc6c6ccccc65)c5ccccc54)ccc32)cc1]

(C-50)

The preparation steps of the 9,10-dihydro-acridine derivative of Formula C-50 were the same as those for the 9,10-dihydro-acridine derivative of Formula C-49 provided in Example 37, except that:

the compound E-1 in Step (3) of Example 37 was replaced by the compound of Formula E-2, and the yield was 85%:

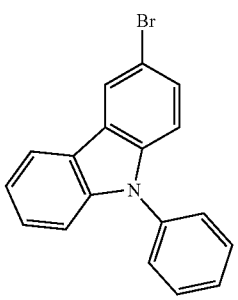

(E-2)

Example 39

This example provides a 9,10-dihydro-acridine derivative having a structure of Formula C-51:

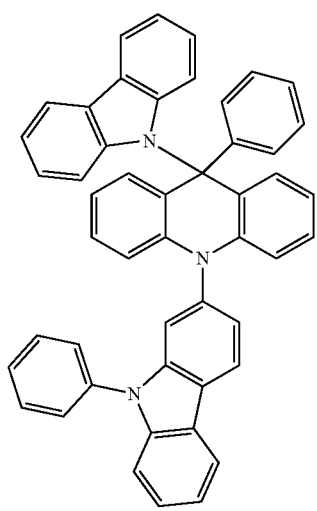

(C-51)

The preparation steps of the 9,10-dihydro-acridine derivative of Formula C-51 were the same as those for the 9,10-dihydro-acridine derivative of Formula C-49 provided in Example 37, except that:

the compound E-1 in Step (3) of Example 37 was replaced by the compound of Formula E-3, and the yield was 78%:

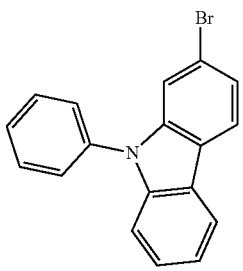

(E-3)

Example 40

This example provides a 9,10-dihydro-acridine derivative having a structure of Formula C-52:

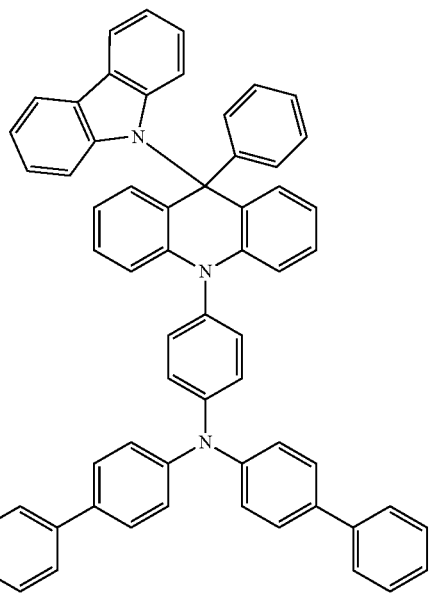

(C-52)

The preparation steps of the 9,10-dihydro-acridine derivative of Formula C-52 were the same as those for the 9,10-dihydro-acridine derivative of Formula C-49 provided in Example 37, except that:

the compound E-1 in Step (3) of Example 37 was replaced by the compound of Formula E-4, and the yield was 85%:

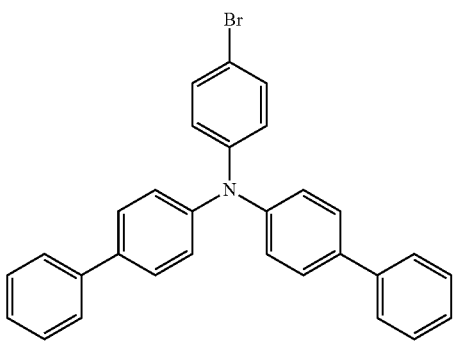

(E-4)

Example 41

This example provides a 9,10-dihydro-acridine derivative having a structure of Formula C-53:

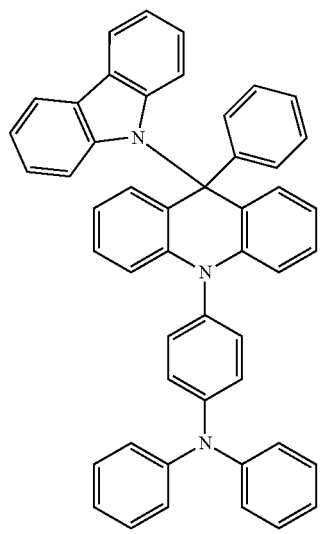

(C-53)

The preparation steps of the 9,10-dihydro-acridine derivative of Formula C-53 were the same as those for the 9,10-dihydro-acridine derivative of Formula C-49 provided in Example 37, except that:

the compound E-1 in Step (3) of Example 37 was replaced by the compound of Formula E-5, and the yield was 82%:

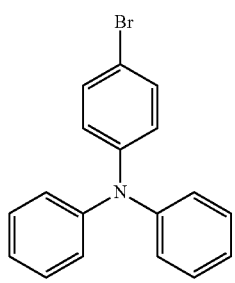

(E-5)

Example 42

This example provides a 9,10-dihydro-acridine derivative having a structure of Formula C-54:

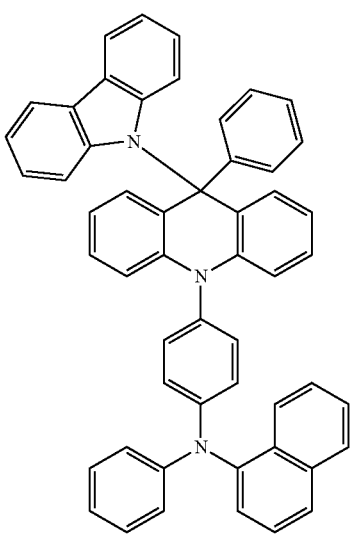

(C-54)

The preparation steps of the 9,10-dihydro-acridine derivative of Formula C-54 were the same as those for the 9,10-dihydro-acridine derivative of Formula C-49 provided in Example 37, except that:

the compound E-1 in Step (3) of Example 37 was replaced by the compound of Formula E-6, and the yield was 84%:

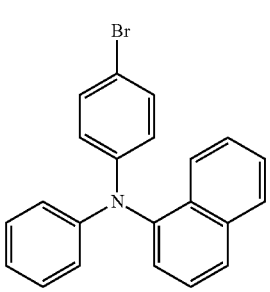

(E-6)

Example 43

This example provides a 9,10-dihydro-acridine derivative having a structure of Formula C-55:

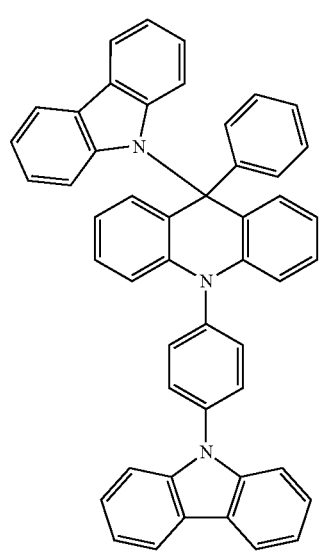

(C-55)

The preparation steps of the 9,10-dihydro-acridine derivative of Formula C-55 were the same as those for the 9,10-dihydro-acridine derivative of Formula C-49 provided in Example 37, except that:

the compound E-1 in Step (3) of Example 37 was replaced by the compound of Formula E-7. The yield was 81%:

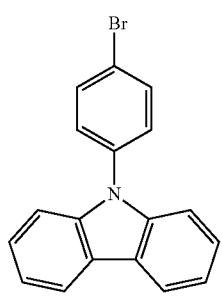

(E-7)

Example 44

This example provides a 9,10-dihydro-acridine derivative having a structure of Formula C-56:

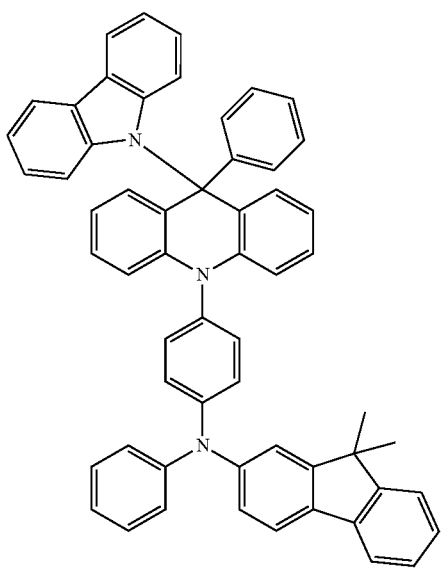

(C-56)

The preparation steps of the 9,10-dihydro-acridine derivative of Formula C-56 were the same as those for the 9,10-dihydro-acridine derivative of Formula C-49 provided in Example 37, except that:

the compound E-1 in Step (3) of Example 37 was replaced by the compound of Formula E-8. The yield was 84%:

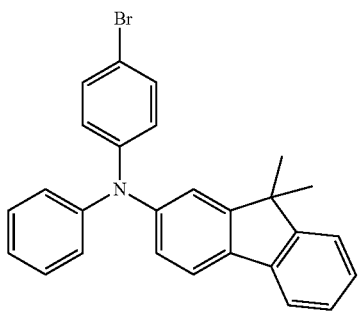

(E-8)

Example 45

This example provides a 9,10-dihydro-acridine derivative having a structure of Formula C-57:

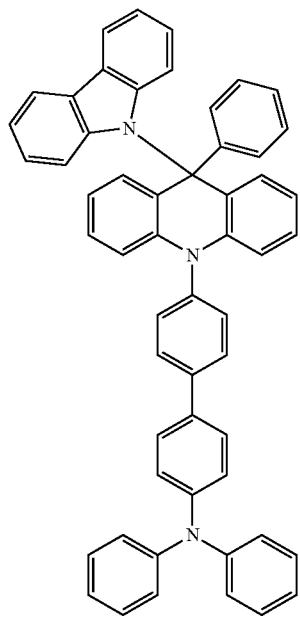

(C-57)

The preparation steps of the 9,10-dihydro-acridine derivative of Formula C-57 were the same as those for the 9,10-dihydro-acridine derivative of Formula C-49 provided in Example 37, except that:

the compound E-1 in Step (3) of Example 37 was replaced by the compound of Formula E-9. The yield was 85%:

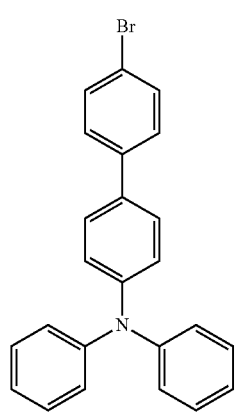

(E-9)

Example 46

This example provides a 9,10-dihydro-acridine derivative having a structure of Formula C-58:

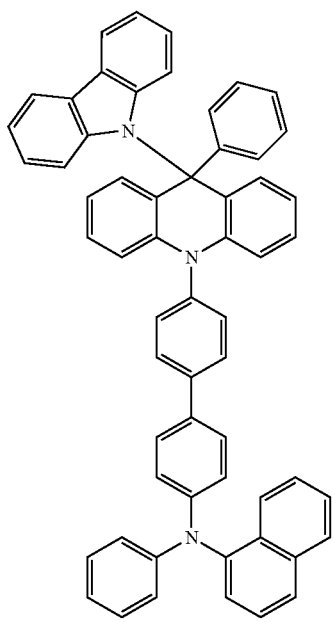

(C-58)

The preparation steps of the 9,10-dihydro-acridine derivative of Formula C-58 were the same as those for the 9,10-dihydro-acridine derivative of Formula C-49 provided in Example 37, except that:

the compound E-1 in Step (3) of Example 37 was replaced by the compound of Formula E-10. The yield was 82%:

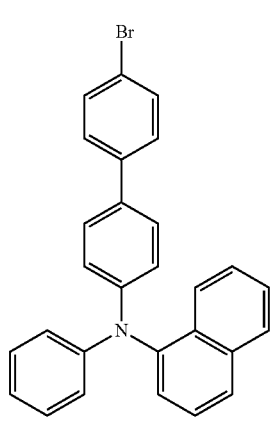

(E-10)

Example 47

This example provides a 9,10-dihydro-acridine derivative having a structure of Formula C-59:

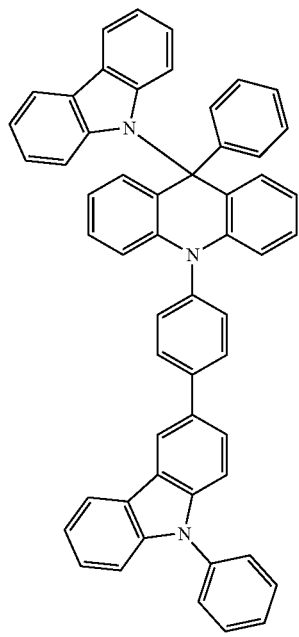

(C-59)

The preparation steps of the 9,10-dihydro-acridine derivative of Formula C-59 were the same as those for the 9,10-dihydro-acridine derivative of Formula C-49 provided in Example 37, except that:

the compound E-1 in Step (3) of Example 37 was replaced by the compound of Formula E-11. The yield was 83%:

Example 48

This example provides a 9,10-dihydro-acridine derivative having a structure of Formula C-60:

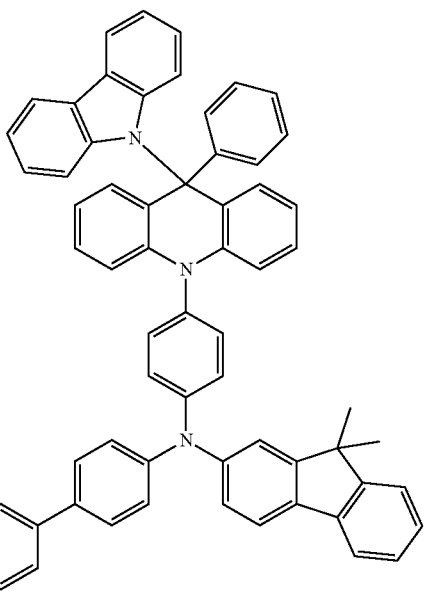

(C-90)

The preparation steps of the 9,10-dihydro-acridine derivative of Formula C-60 were the same as those for the 9,10-dihydro-acridine derivative of Formula C-49 provided in Example 37, except that:

the compound E-1 in Step (3) of Example 37 was replaced by the compound of Formula E-12. The yield was 85%:

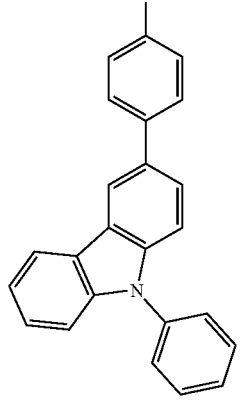

(E-11)

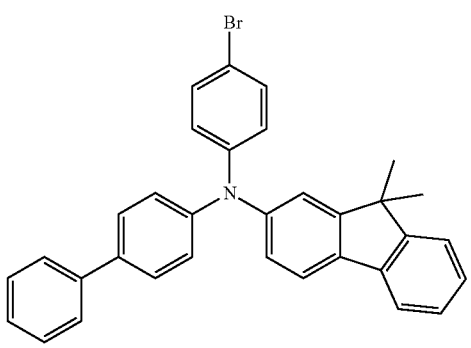

(E-12)

Example 49
This example provides a 9,10-dihydro-acridine derivative having a structure of Formula C-61:
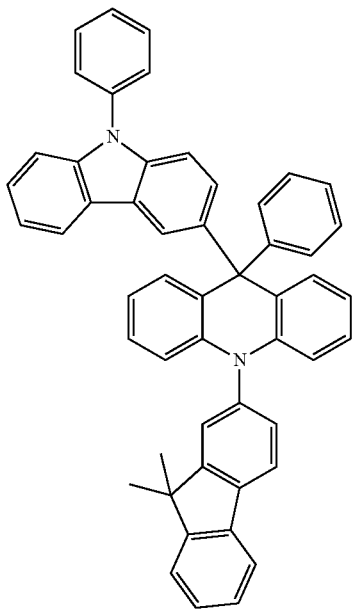
(C-61)
The synthesis route for the 9,10-dihydro-acridine derivative of Formula C-61 is shown below:
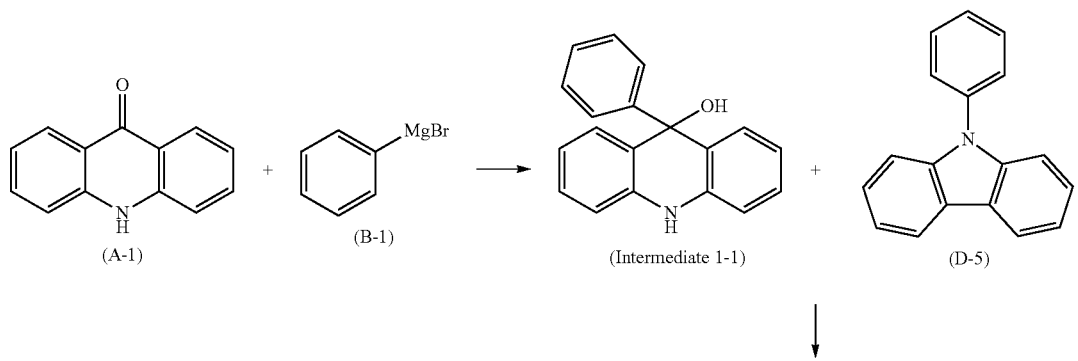

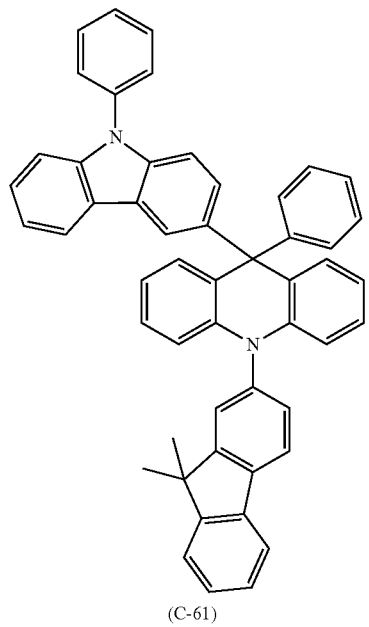

(C-61)

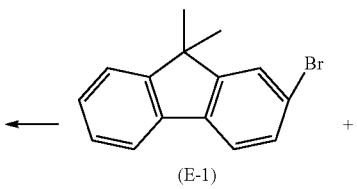

(E-1)

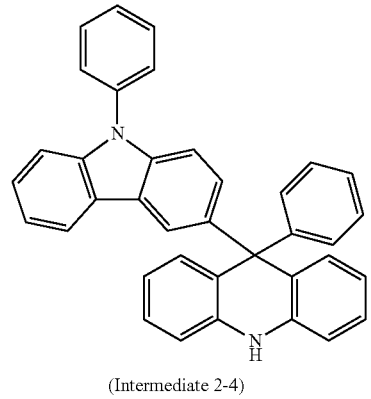

(Intermediate 2-4)

The method for preparing the 9,10-dihydro-acridine derivative of Formula C-61 comprises specifically the following steps.

(1) Synthesis of Intermediate 1-1

Under nitrogen atmosphere, 9(10H)-acridone (the compound of Formula A-1) (19.5 g, 100 mmol), and tetrahydrofuran (700 mL) were added to a 1 L three-neck flask. A phenyl magnesium bromide (the compound of Formula B-1) solution (110 mL, 1 M) was added at −20° C., reacted at room temperature for 8 hrs, and then quenched by adding an aqueous ammonium chloride solution. The reaction solution was extracted with dichloromethane (3×), and then the solvent was removed by rotary evaporation. The residue was purified by column chromatography on silica gel, to obtain the intermediate 1-1 as a solid (24 g, yield: 88%).

(2) Synthesis of Intermediate 2-4

Under nitrogen atmosphere, the intermediate 1-1 (22.0 g, 80 mmol), 9-phenylcarbazole (the compound of Formula D-5) (20 g, 80 mmol), and dichloromethane (800 mL) were added. Then, a solution of boron trifluoride (11.5 mL, 80 mmol) in diethyl ether was added dropwise, reacted at room temperature for 5 hrs, and then quenched by adding water. The reaction solution was extracted with toluene (3×), and then the solvent was removed by rotary evaporation. The residue was purified by column chromatography on silica gel, to obtain the intermediate 2-4 as a solid (33.3 g, yield: 85%).

(3) Synthesis of 9,10-dihydro-acridine derivative C-61

Under nitrogen atmosphere, the intermediate 2-4 (10.0 g, 20 mmol), palladium diacetate (0.13 g, 0.6 mmol), tri-tert-butylphosphine (0.45 g, 2.2 mmol), a compound of Formula E-1 (6.0 g, 22 mmol), sodium-t-butoxide (5.7 g), and toluene (300 mL) were added, reacted at 110° C. for 12 hrs, and then cooled to room temperature. The reaction solution was extracted with chloroform, and then the solvent was removed by rotary evaporation. The residue was purified by column chromatography on silica gel, to obtain the compound C-61 as a solid (11.5 g, yield 84%).

Element analysis: (C52H38N2) calculated: C, 90.40; H, 5.54; N, 4.05; found: C, 90.43; H, 5.51; N, 4.03; HRMS (ESI) m/z (M+): calculated: 690.3035; found: 690.3017.

Example 50

This example provides a 9,10-dihydro-acridine derivative having a structure of Formula C-62:

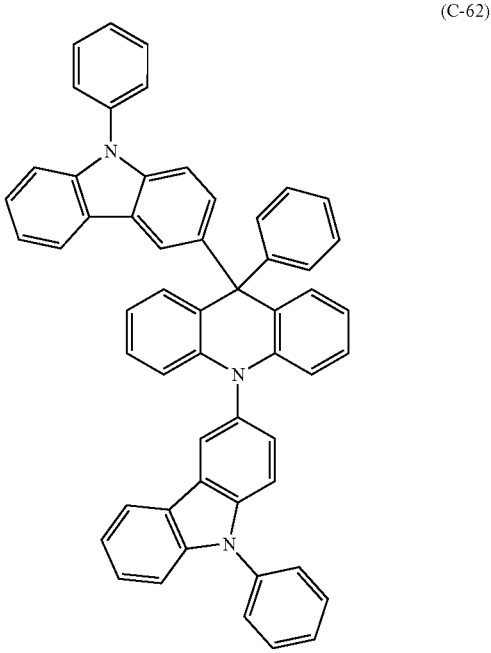 [SMILES: c1ccc(-n2c3ccccc3c3cc(N4c5ccccc5C(c5ccccc5)(c5ccc6c(c5)c5ccccc5n6-c5ccccc5)c5ccccc54)ccc32)cc1]

(C-62)

The preparation steps of the 9,10-dihydro-acridine derivative of Formula C-62 were the same as those for the 9,10-dihydro-acridine derivative of Formula C-61 provided in Example 49, except that:

the compound E-1 in Step (3) of Example 49 was replaced by the compound of Formula E-2, and the yield was 82%:

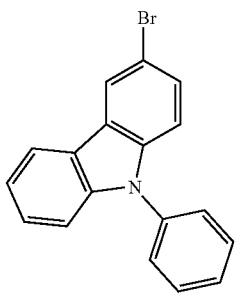

(E-2)

Example 51

This example provides a 9,10-dihydro-acridine derivative having a structure of Formula C-63:

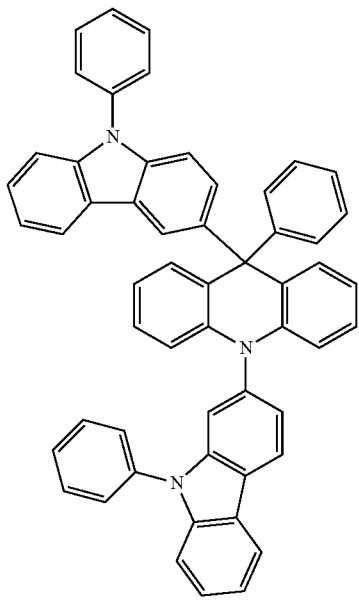

(C-63)

The preparation steps of the 9,10-dihydro-acridine derivative of Formula C-63 were the same as those for the 9,10-dihydro-acridine derivative of Formula C-63 provided in Example 49, except that:

the compound E-1 in Step (3) of Example 49 was replaced by the compound of Formula E-3, and the yield was 80%:

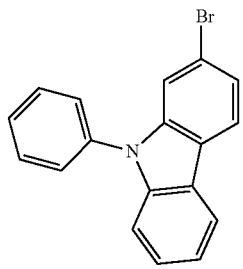

(E-3)

Example 52

This example provides a 9,10-dihydro-acridine derivative having a structure of Formula C-64:

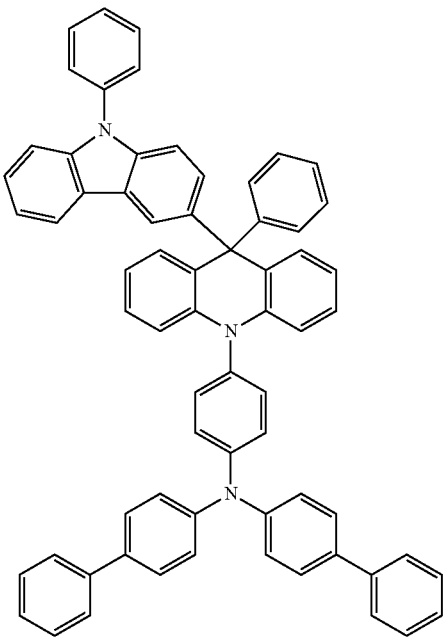

(C-64)

The preparation steps of the 9,10-dihydro-acridine derivative of Formula C-64 were the same as those for the 9,10-dihydro-acridine derivative of Formula C-61 provided in Example 49, except that:

the compound E-1 in Step (3) of Example 49 was replaced by the compound of Formula E-4, and the yield was 81%:

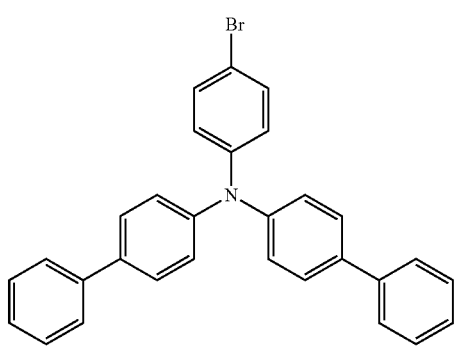

(E-4)

Example 53

This example provides a 9,10-dihydro-acridine derivative having a structure of Formula C-65:

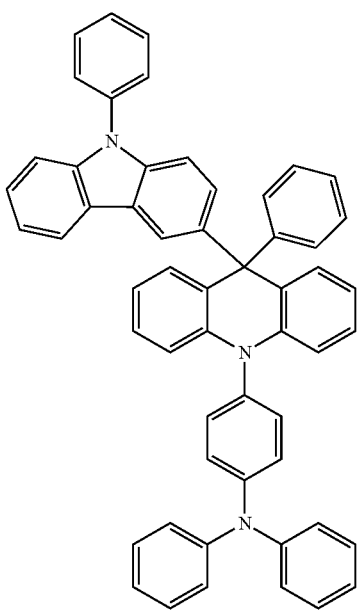

(C-65)

The preparation steps of the 9,10-dihydro-acridine derivative of Formula C-65 were the same as those for the 9,10-dihydro-acridine derivative of Formula C-61 provided in Example 49, except that:

the compound E-1 in Step (3) of Example 49 was replaced by the compound of Formula E-5, and the yield was 85%:

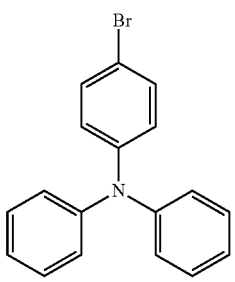

(E-5)

Example 54

This example provides a 9,10-dihydro-acridine derivative having a structure of Formula C-66:

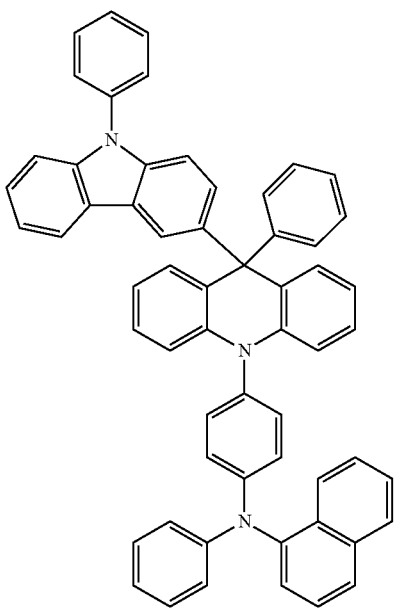

(c-66)

The preparation steps of the 9,10-dihydro-acridine derivative of Formula C-66 were the same as those for the 9,10-dihydro-acridine derivative of Formula C-61 provided in Example 49, except that:

the compound E-1 in Step (3) of Example 49 was replaced by the compound of Formula E-6, and the yield was 83%:

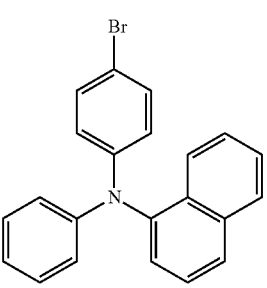

(E-6)

Example 55

This example provides a 9,10-dihydro-acridine derivative having a structure of Formula C-67:

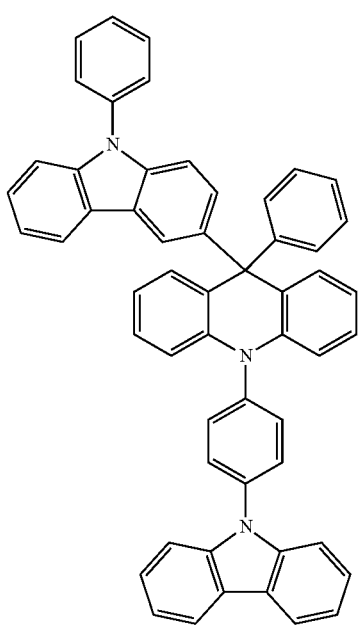

(C-67)

The preparation steps of the 9,10-dihydro-acridine derivative of Formula C-67 were the same as those for the 9,10-dihydro-acridine derivative of Formula C-61 provided in Example 49, except that:

the compound E-1 in Step (3) of Example 49 was replaced by the compound of Formula E-7. The yield was 82%:

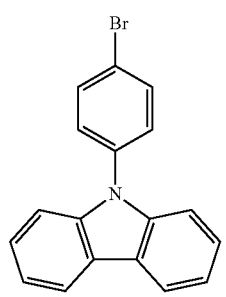

(E-7)

Example 56

This example provides a 9,10-dihydro-acridine derivative having a structure of Formula C-68:

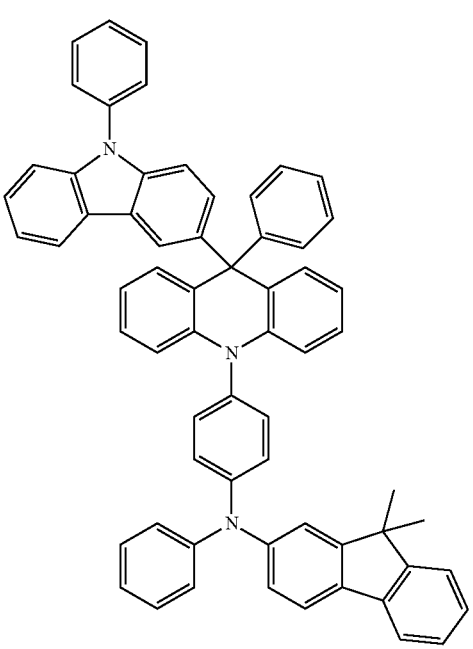

(C-68)

The preparation steps of the 9,10-dihydro-acridine derivative of Formula C-68 were the same as those for the 9,10-dihydro-acridine derivative of Formula C-61 provided in Example 49, except that:

the compound E-1 in Step (3) of Example 49 was replaced by the compound of Formula E-8. The yield was 85%:

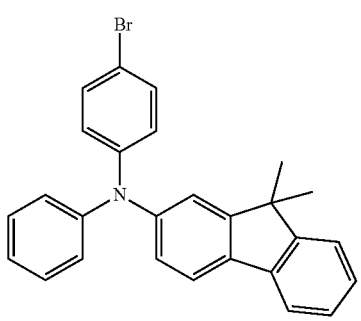

(E-8)

Example 57

This example provides a 9,10-dihydro-acridine derivative having a structure of Formula C-69:

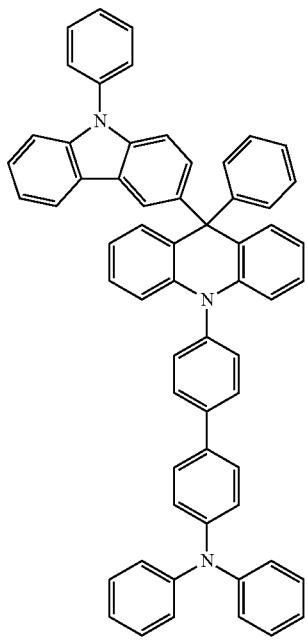

(C-69)

The preparation steps of the 9,10-dihydro-acridine derivative of Formula C-69 were the same as those for the 9,10-dihydro-acridine derivative of Formula C-61 provided in Example 49, except that:

the compound E-1 in Step (3) of Example 49 was replaced by the compound of Formula E-9. The yield was 83%:

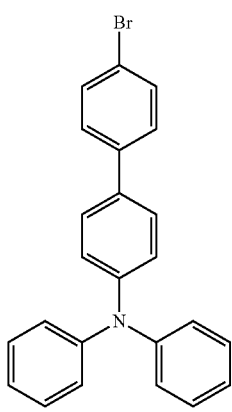

(E-9)

Example 58

This example provides a 9,10-dihydro-acridine derivative having a structure of Formula C-70:

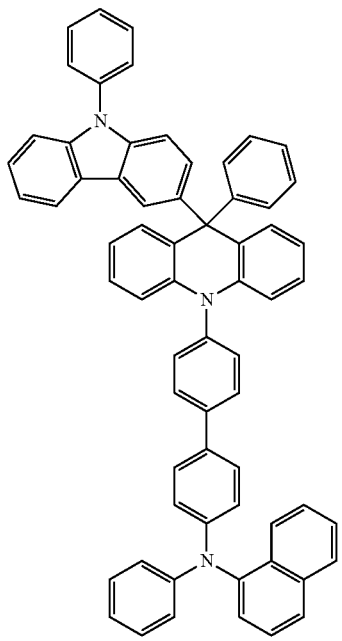

(C-70)

The preparation steps of the 9,10-dihydro-acridine derivative of Formula C-70 were the same as those for the 9,10-dihydro-acridine derivative of Formula C-61 provided in Example 49, except that:

the compound E-1 in Step (3) of Example 49 was replaced by the compound of Formula E-10. The yield was 86%:

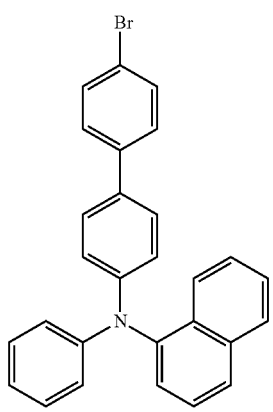

(E-9)

Example 59

This example provides a 9,10-dihydro-acridine derivative having a structure of Formula C-71:

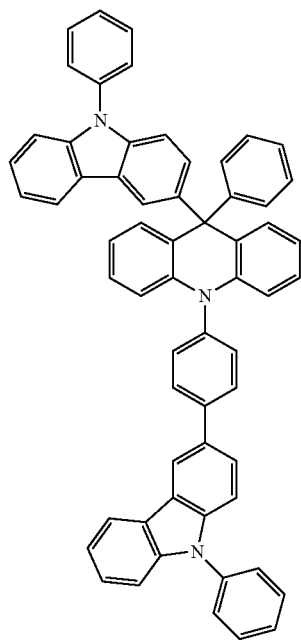

(C-71)

The preparation steps of the 9,10-dihydro-acridine derivative of Formula C-71 were the same as those for the 9,10-dihydro-acridine derivative of Formula C-61 provided in Example 49, except that:

the compound E-1 in Step (3) of Example 49 was replaced by the compound of Formula E-11. The yield was 82%:

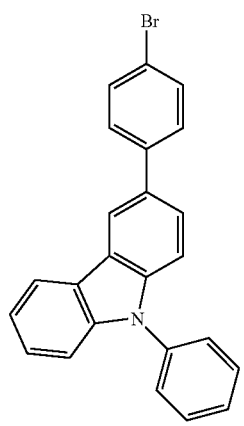

(E-11)

Example 60

This example provides a 9,10-dihydro-acridine derivative having a structure of Formula C-72:

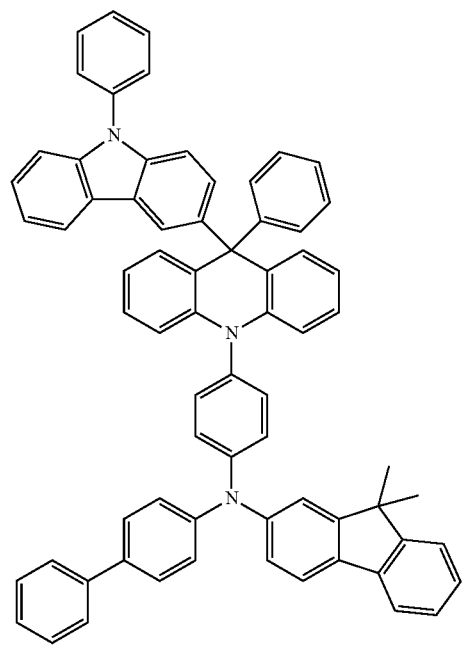

(C-72)

The preparation steps of the 9,10-dihydro-acridine derivative of Formula C-72 were the same as those for the 9,10-dihydro-acridine derivative of Formula C-61 provided in Example 49, except that:

the compound E-1 in Step (3) of Example 49 was replaced by the compound of Formula E-12. The yield was 81%:

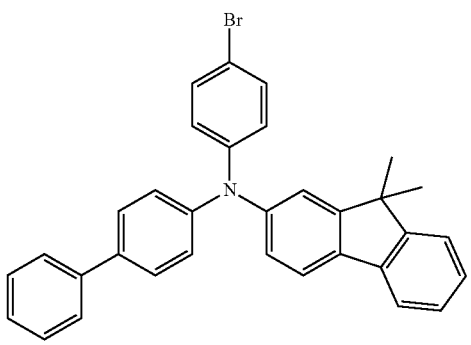

(E-12)

Example 61
This example provides a 9,10-dihydro-acridine derivative having a structure of Formula C-74:
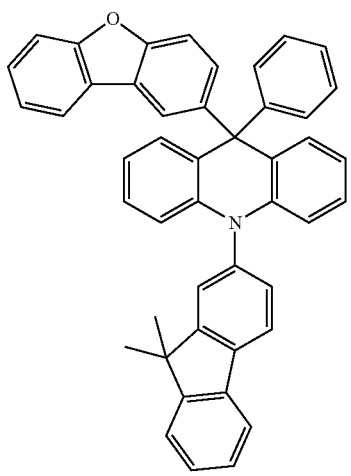
(C-74)
The synthesis route for the 9,10-dihydro-acridine derivative of Formula C-74 is shown below:
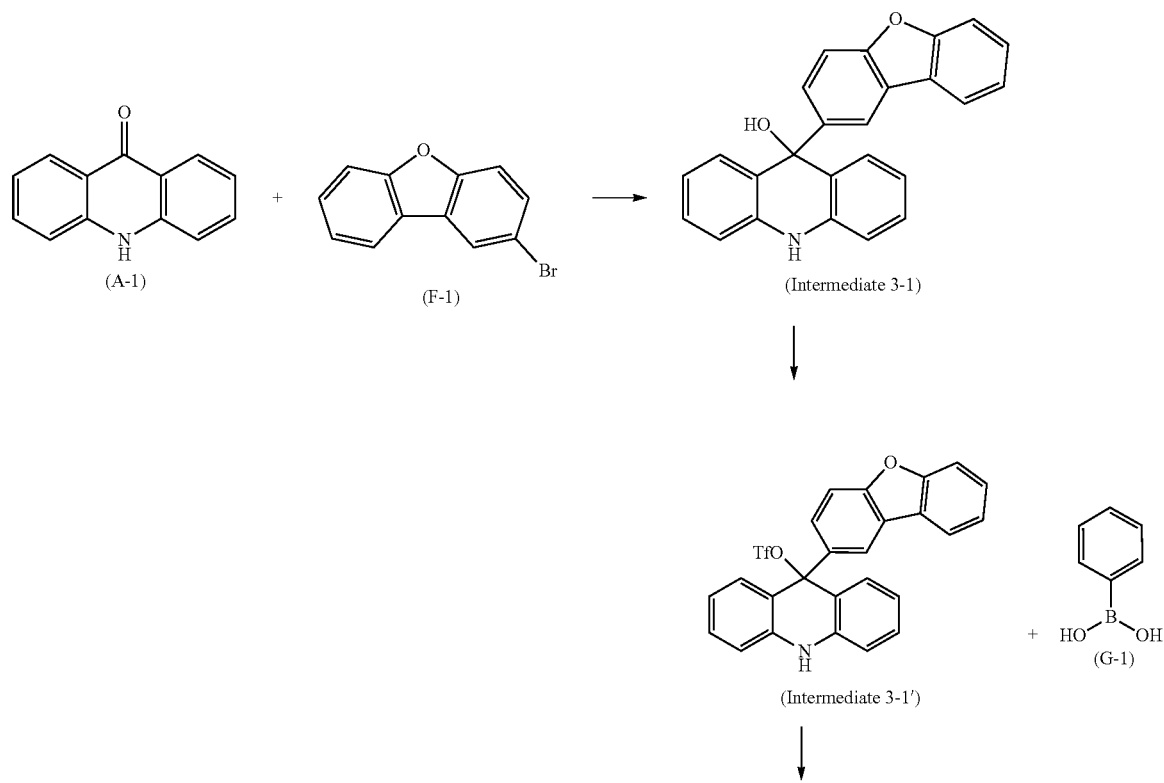

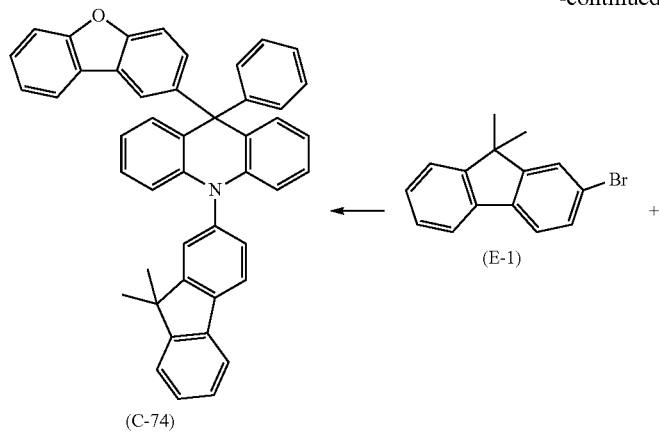

(C-74)

The method for preparing the 9,10-dihydro-acridine derivative of Formula C-74 comprises specifically the following steps.

(1) Synthesis of Intermediate 3-1

Under nitrogen atmosphere, the compound of Formula F-1 (24.6 g, 100 mmol), and tetrahydrofuran (500 mL) were added. At −78° C., n-butyl lithium (63 mL, 1.6 M) was added dropwise, reacted for 30 min at a low temperate and then for 3 hrs at an elevated temperature of 30° C., and then cooled to −78° C. A solution of 9(10H)-acridone (the compound of Formula A-1) (500 mL, 0.2 M, 9.5 g (100 mmol)) was added, slowly heated to 30° C., reacted for 15 hrs, and then quenched by adding an aqueous ammonium chloride solution. The reaction solution was extracted with chloroform, and then the solvent was removed by rotary evaporation. The residue was purified by column chromatography on silica gel, to obtain the intermediate 3-1 as a solid (20.3 g, yield 56%);

(2) Synthesis of Intermediate 3-1'

Under nitrogen atmosphere, the intermediate 3-1 (14.5 g, 40 mmol), triethylamine (5.0 g, 48 mmol), and dichloromethane (400 mL) were added. Trifluoromethanesulfonic anhydride (13.5 g, 48 mmol) was added at −20° C., and reacted at room temperature for 3 hrs. The reaction solution was extracted with toluene (3×), and then the solvent was removed by rotary evaporation. The residue was washed with methanol (3×), to obtain an intermediate 3-1' (17 g, yield: 87%).

(3) Synthesis of Intermediate 4-1

Under nitrogen atmosphere, the intermediate 3-1' (14.8 g, 30 mmol), phenylboronic acid (the compound of Formula G-1) (3.7 g, 30 mmol), potassium phosphate (70 g, 33 mmol), tetrakis(triphenylphosphine) palladium (1.7 g, 1.5 mmol), water (50 mL), and 1,4-dioxane (300 mL) were added, reacted at 120° C. for 8 hrs, and then cooled to room temperature. The reaction solution was extracted with chloroform, and then the solvent was removed by rotary evaporation. The residue was purified by column chromatography on silica gel, to obtain the intermediate 4-1 as a solid (10.3 g, yield 81%).

(4) Synthesis of 9,10-dihydro-acridine derivative C-74

Under nitrogen atmosphere, the intermediate 4-1 (8.5 g, 20 mmol), palladium diacetate (0.13 g, 0.6 mmol), tri-tert-butylphosphine (0.45 g, 2.2 mmol), the compound of Formula E-1 (6.0 g, 22 mmol), sodium-t-butoxide (5.7 g), and toluene (300 mL) were added, reacted at 110° C. for 12 hrs, and then cooled to room temperature. The reaction solution was extracted with chloroform, and then the solvent was removed by rotary evaporation. The residue was purified by column chromatography on silica gel, to obtain the compound C-74 as a solid (10.3 g, yield 84%).

Element analysis: (C46H33NO) calculated: C, 89.73; H, 5.40; N, 2.27; O, 2.60; found: C, 89.79; H, 5.37; N, 2.30; O, 2.57; HRMS (ESI) m/z (M+): calculated: 615.2562; found: 615.2577.

Example 62

This example provides a 9,10-dihydro-acridine derivative having a structure of Formula C-73:

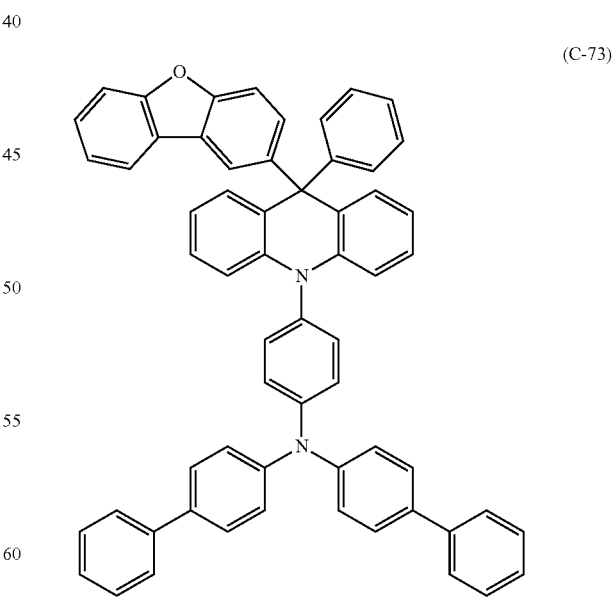

(C-73)

The preparation steps of the 9,10-dihydro-acridine derivative of Formula C-73 were the same as those for the 9,10-dihydro-acridine derivative of Formula C-74 provided in Example 61, except that:

the compound E-1 in Step (4) of Example 61 was replaced by the compound of Formula E-4, and the yield was 81%:

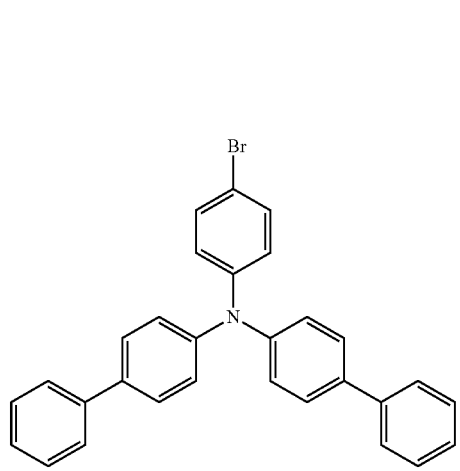
(E-4)

Example 63

This example provides a 9,10-dihydro-acridine derivative having a structure of Formula C-75:

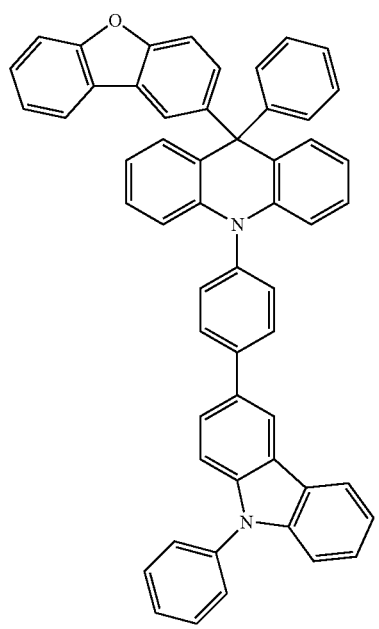
(C-75)

The preparation steps of the 9,10-dihydro-acridine derivative of Formula C-75 were the same as those for the 9,10-dihydro-acridine derivative of Formula C-74 provided in Example 61, except that:

the compound E-1 in Step (4) of Example 61 was replaced by the compound of Formula E-11. The yield was 82%:

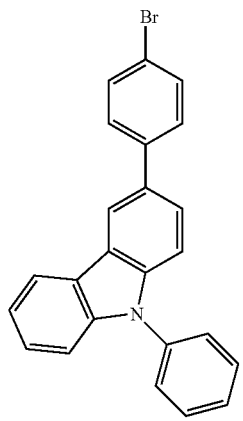
(E-11)

Example 64

This example provides a 9,10-dihydro-acridine derivative having a structure of Formula C-76:

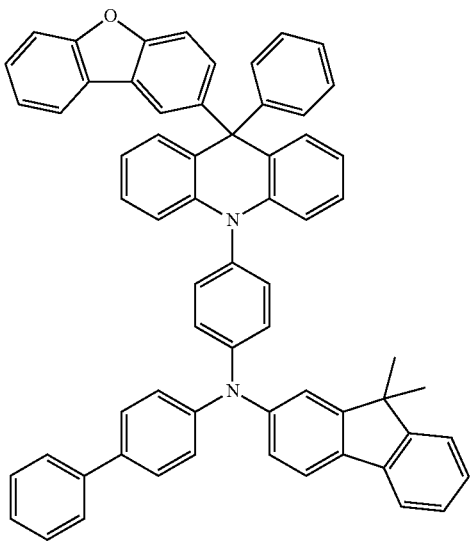
(C-76)

The preparation steps of the 9,10-dihydro-acridine derivative of Formula C-76 were the same as those for the 9,10-dihydro-acridine derivative of Formula C-74 provided in Example 61, except that:

the compound E-1 in Step (4) of Example 61 was replaced by the compound of Formula E-12. The yield was 84%:

(E-12)
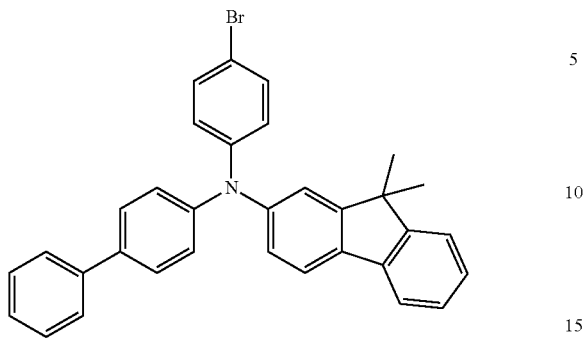
Example 65
This example provides a 9,10-dihydro-acridine derivative having a structure of Formula C-78:
(C-78)
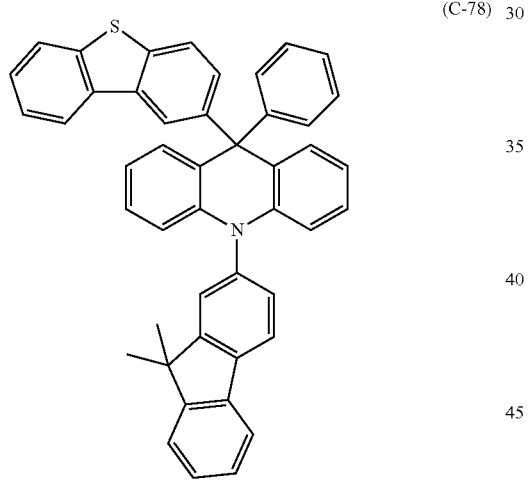
The synthesis route for the 9,10-dihydro-acridine derivative of Formula C-78 is shown below:
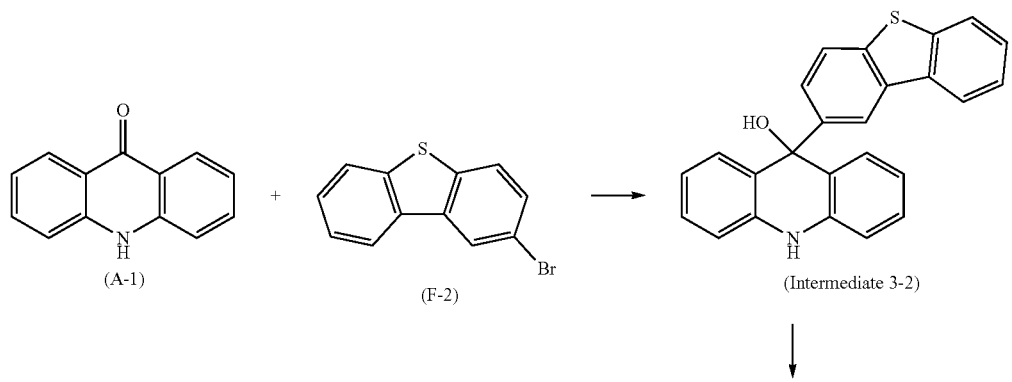

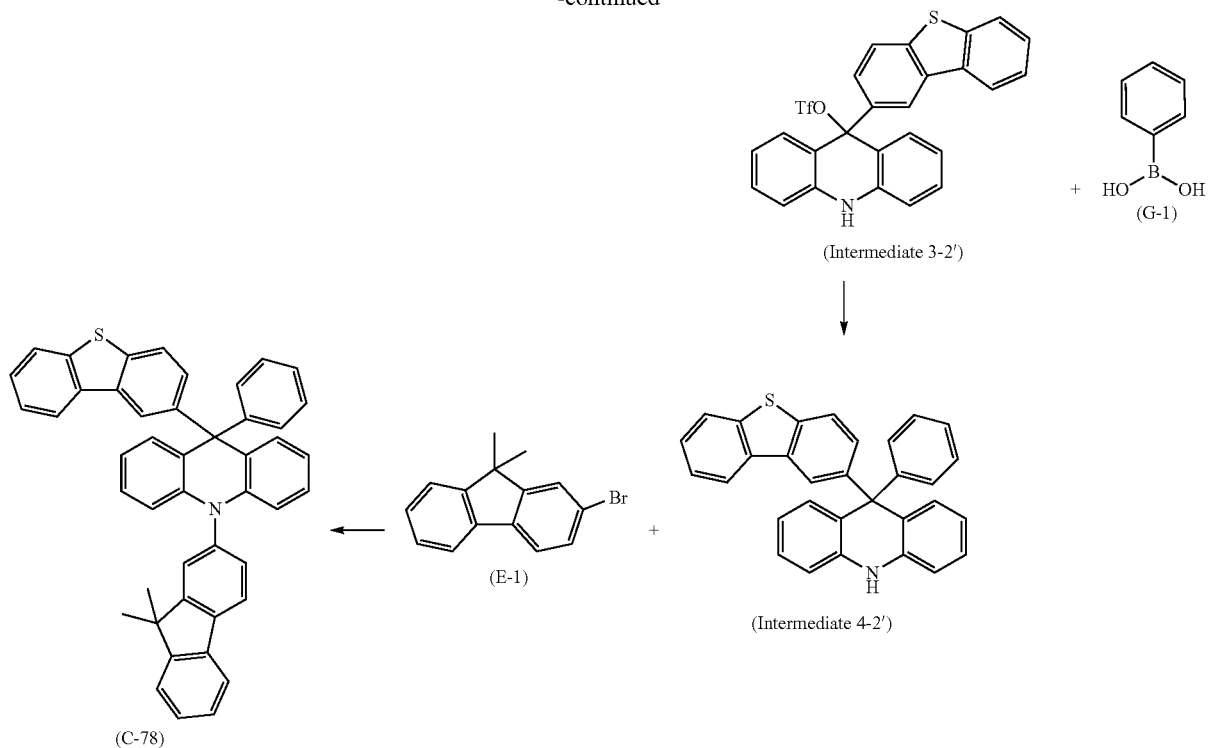

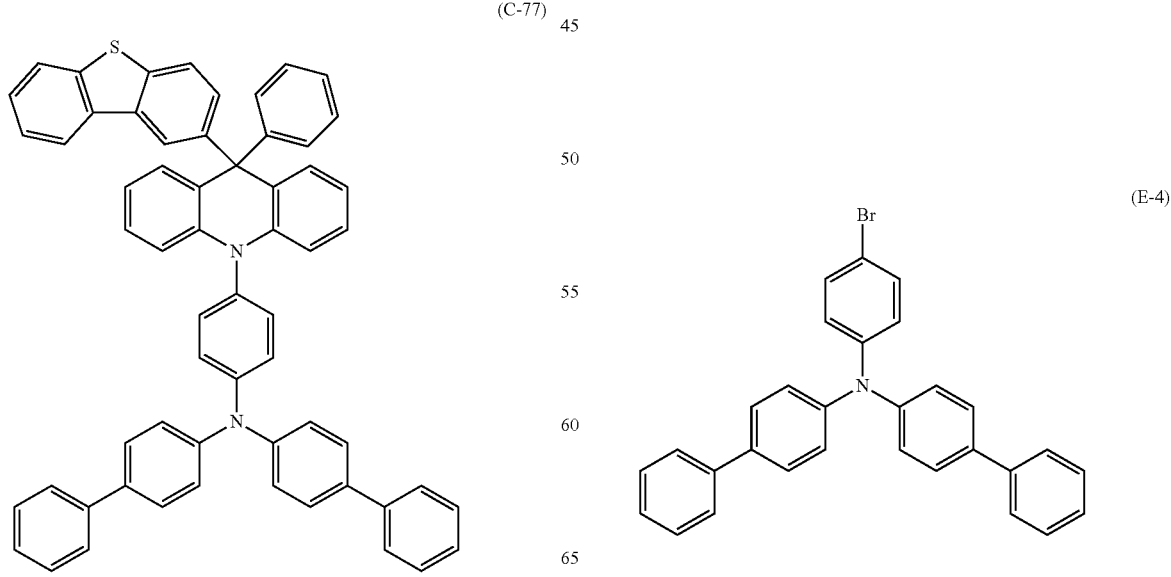

The preparation steps of the 9,10-dihydro-acridine derivative of Formula C-78 were the same as those for the 9,10-dihydro-acridine derivative of Formula C-74 provided in Example 61, except that: the compound F-1 in Step (1) of Example 61 was replaced by the compound of Formula F-2.

Element analysis: (C46H33NS) calculated: C, 87.44; H, 5.26; N, 2.22; S, 5.07; found: C, 87.39; H, 5.24; N, 2.27; S, 5.11; HRMS (ESI) m/z (M+): calculated: 631.2334; found: 631.2316.

Example 66

This example provides a 9,10-dihydro-acridine derivative having a structure of Formula C-77:

The preparation steps of the 9,10-dihydro-acridine derivative of Formula C-77 were the same as those for the 9,10-dihydro-acridine derivative of Formula C-78 provided in Example 65, except that:

the compound E-1 in Example 65 was replaced by the compound of Formula E-4, and the yield was 85%:

Example 67

This example provides a 9,10-dihydro-acridine derivative having a structure of Formula C-79:

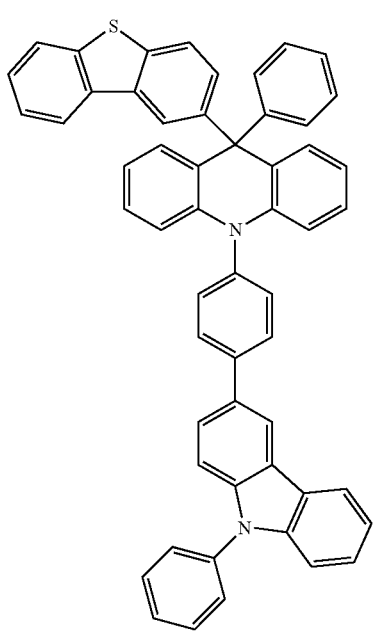

(C-79)

The preparation steps of the 9,10-dihydro-acridine derivative of Formula C-79 were the same as those for the 9,10-dihydro-acridine derivative of Formula C-78 provided in Example 65, except that:

the compound E-1 in Example 65 was replaced by the compound of Formula E-11. The yield was 82%:

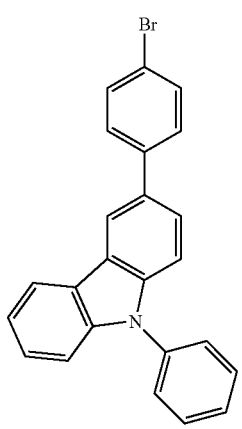

(E-11)

Example 68

This example provides a 9,10-dihydro-acridine derivative having a structure of Formula C-80:

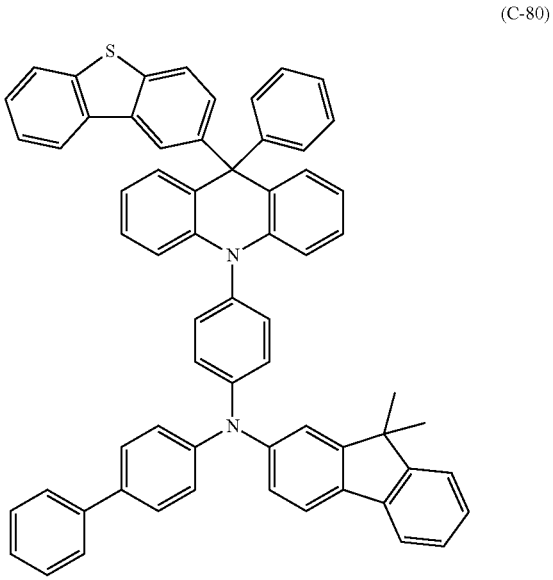 [SMILES: CC1(C)c2ccccc2-c2ccc(N(c3ccc(-c4ccccc4)cc3)c3ccc(N4c5ccccc5C(c5ccccc5)(c5ccc6oc7ccccc7c6c5)c5ccccc54)cc3)cc21]

(C-80)

The preparation steps of the 9,10-dihydro-acridine derivative of Formula C-80 were the same as those for the 9,10-dihydro-acridine derivative of Formula C-78 provided in Example 65, except that:

the compound E-1 in Example 65 was replaced by the compound of Formula E-12. The yield was 83%:

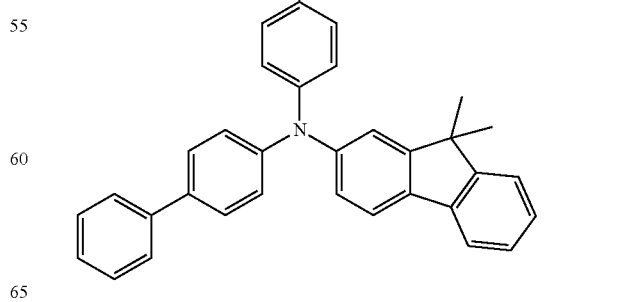

(E-12)

Example 69
This example provides a 9,10-dihydro-acridine derivative having a structure of Formula C-82:
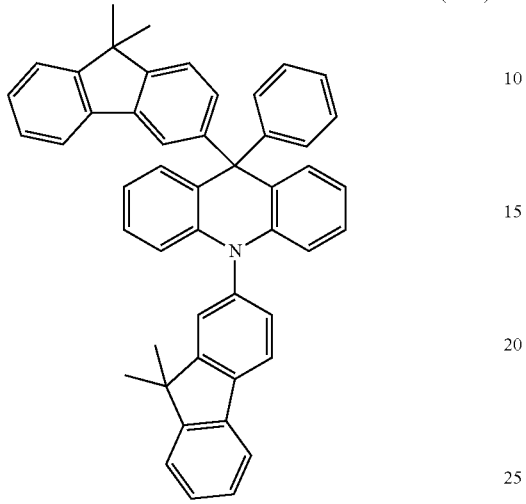
(C-82)
The synthesis route for the 9,10-dihydro-acridine derivative of Formula C-82 is shown below:
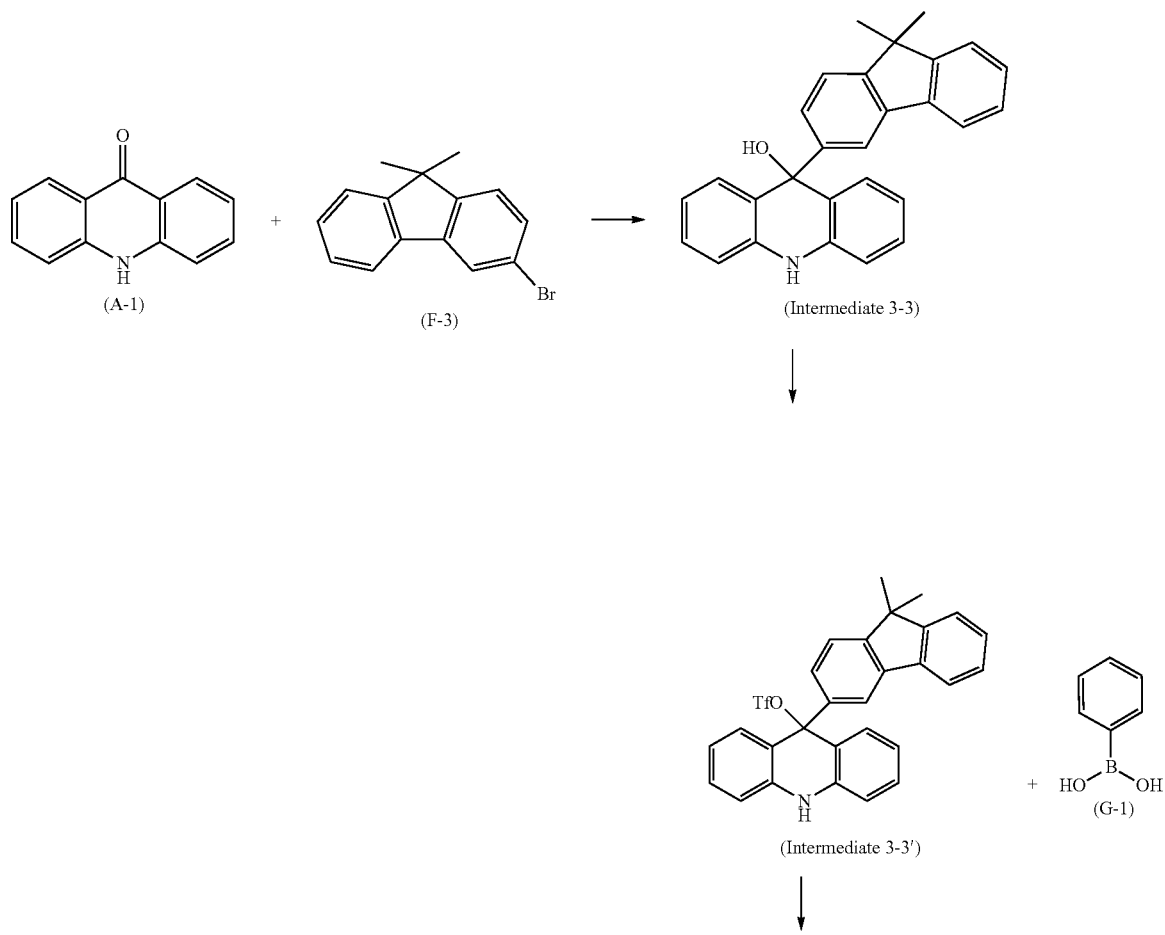

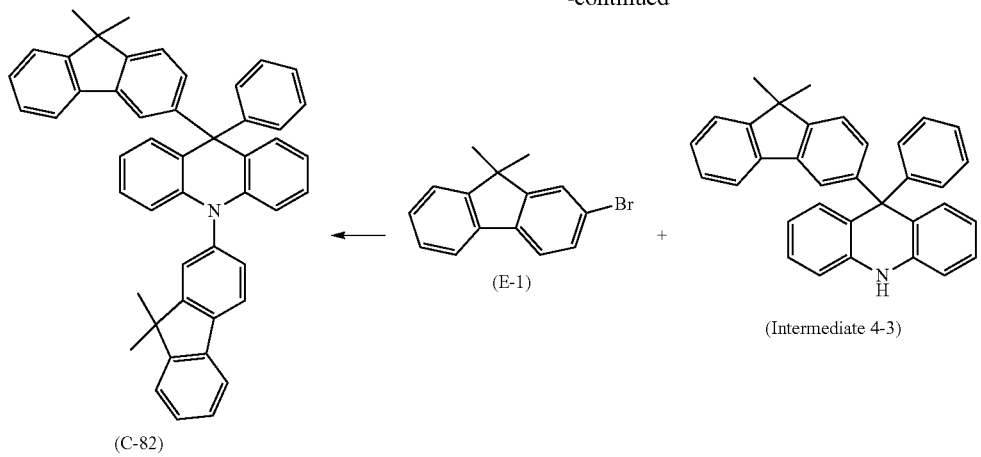

(C-82)

(E-1)

(Intermediate 4-3)

The preparation steps of the 9,10-dihydro-acridine derivative of Formula C-82 were the same as those for the 9,10-dihydro-acridine derivative of Formula C-74 provided in Example 61, except that: the compound F-1 in Step (1) of Example 61 was replaced by the compound of Formula F-3.

Element analysis: (C49H39N) calculated: C, 91.69; H, 6.12; N, 2.18; found: C, 91.63; H, 6.15; N, 2.17; HRMS (ESI) m/z (M+): calculated: 641.3083; found: 641.3095.

Example 70

This example provides a 9,10-dihydro-acridine derivative having a structure of Formula C-81:

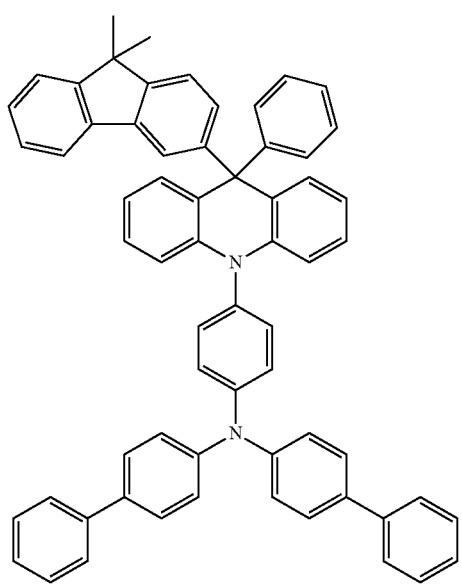

(C-81)

The preparation steps of the 9,10-dihydro-acridine derivative of Formula C-81 were the same as those for the 9,10-dihydro-acridine derivative of Formula C-82 provided in Example 69, except that:

the compound E-1 in Example 69 was replaced by the compound of Formula E-4, and the yield was 81%:

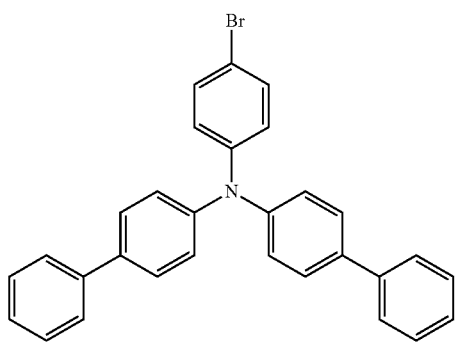

(E-4)

Example 71

This example provides a 9,10-dihydro-acridine derivative having a structure of Formula C-83:

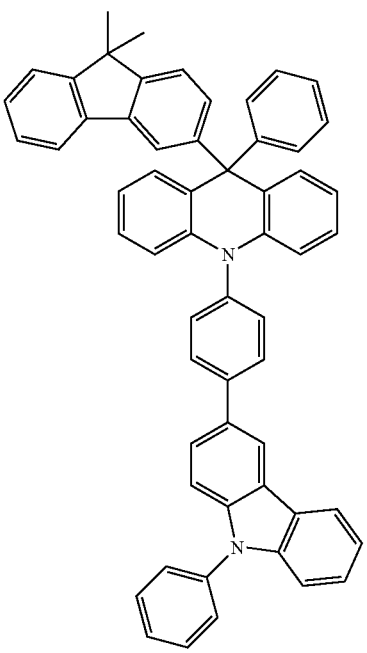

(C-83)

The preparation steps of the 9,10-dihydro-acridine derivative of Formula C-83 were the same as those for the 9,10-dihydro-acridine derivative of Formula C-82 provided in Example 69, except that:

the compound E-1 in Example 69 was replaced by the compound of Formula E-11. The yield was 82%:

the compound E-1 in Example 69 was replaced by the compound of Formula E-12. The yield was 78%:

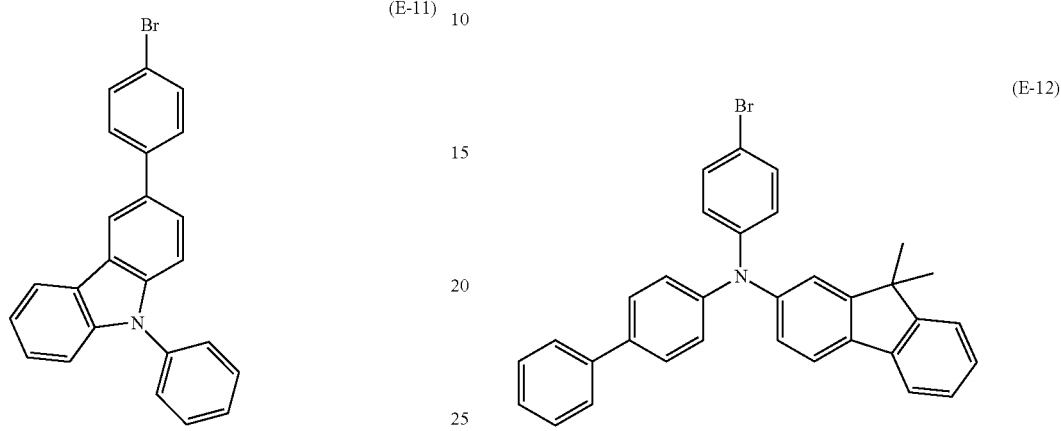

Example 72

This example provides a 9,10-dihydro-acridine derivative having a structure of Formula C-84:

Example 73

This example provides a 9,10-dihydro-acridine derivative having a structure of Formula C-89:

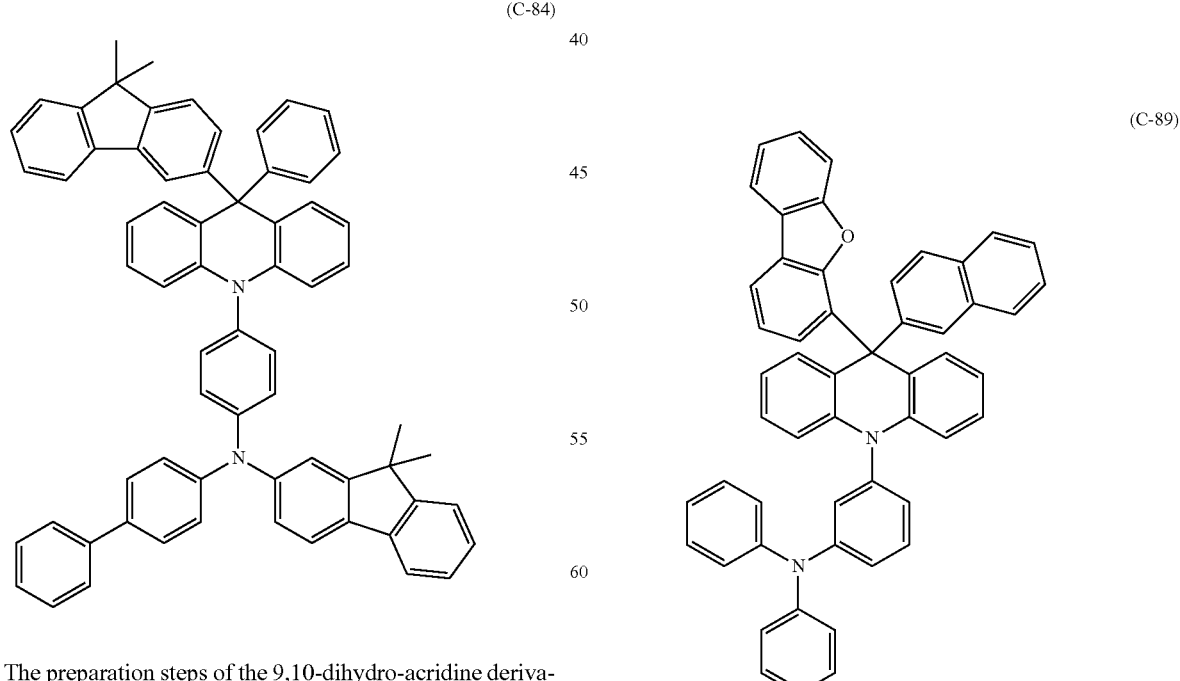

The preparation steps of the 9,10-dihydro-acridine derivative of Formula C-84 were the same as those for the 9,10-dihydro-acridine derivative of Formula C-82 provided in Example 69, except that:

The synthesis route for the 9,10-dihydro-acridine derivative of Formula C-89 is shown below:

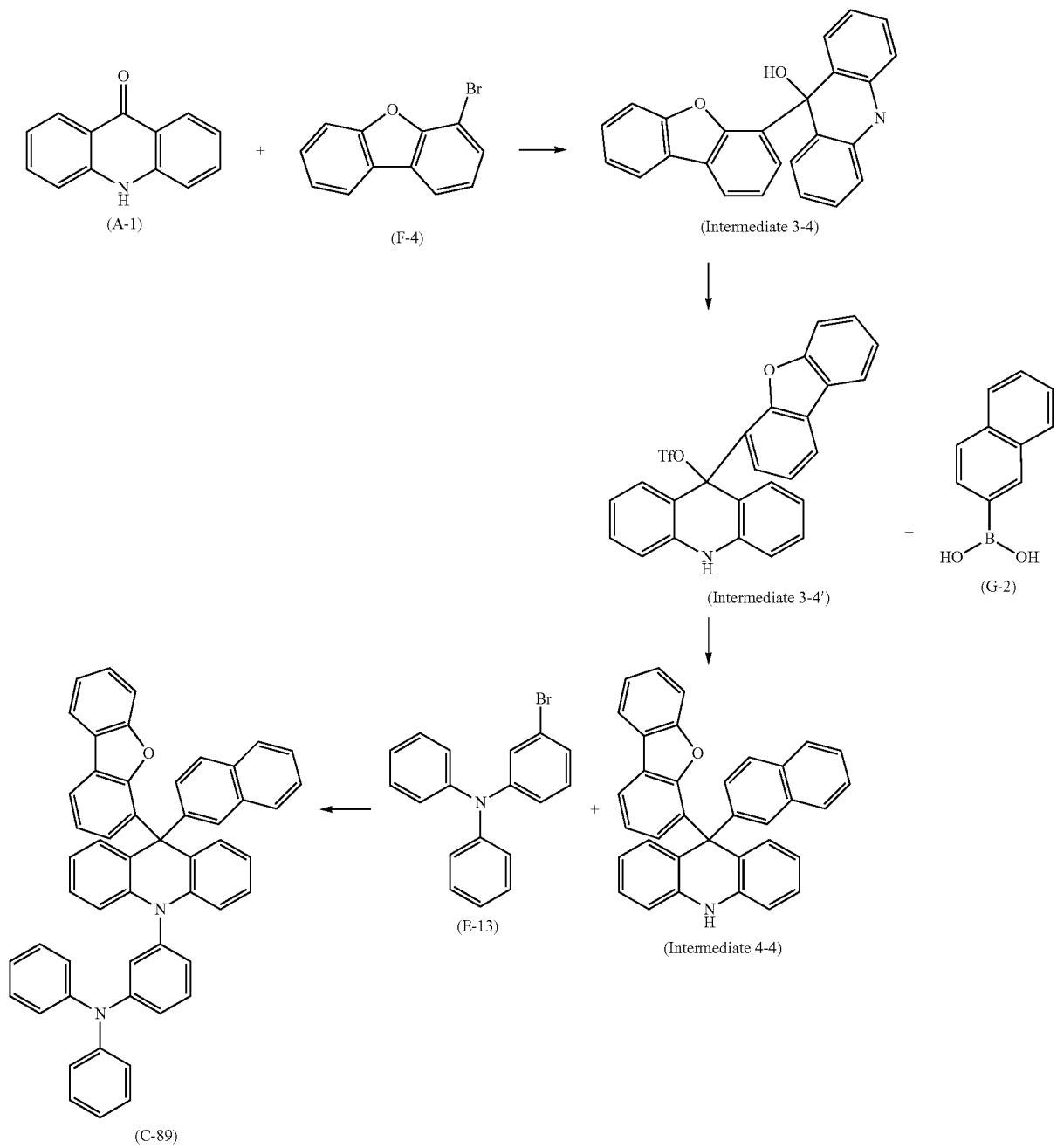

The method for preparing the 9,10-dihydro-acridine derivative of Formula C-89 comprises specifically the following steps.

(1) Synthesis of Intermediate 3-4

Under nitrogen atmosphere, the compound of Formula F-1 (16.8 g, 100 mmol), and tetrahydrofuran (500 mL) were added. At −78° C., n-butyl lithium (63 mL, 1.6 M) was added dropwise, reacted for 30 min at a low temperate and then for 3 hrs at an elevated temperature of 30° C., and then cooled to −78° C. A solution of 9(10H)-acridone (the compound of Formula A-1) (500 mL, 0.2 M, 9.5 g (100 mmol)) was added, slowly heated to 30° C., reacted for 15 hrs, and then quenched by adding an aqueous ammonium chloride solution. The reaction solution was extracted with chloroform, and then the solvent was removed by rotary evaporation. The residue was purified by column chromatography on silica gel, to obtain the intermediate 3-4 as a solid (17.3 g, yield 47%);

(2) Synthesis of Intermediate 3-4'

Under nitrogen atmosphere, the intermediate 3-4 (14.5 g, 40 mmol), triethylamine (5.0 g, 48 mmol), and dichloromethane (400 mL) were added. Trifluoromethanesulfonic anhydride (13.5 g, 48 mmol) was added at −20° C., and reacted at room temperature for 3 hrs. The reaction solution was extracted with toluene (3×), and then the solvent was removed by rotary evaporation. The residue was washed with methanol (3×), to obtain an intermediate 3-4' (17 g, yield: 87%).

(3) Synthesis of Intermediate 4-4

Under nitrogen atmosphere, the intermediate 3-4' (14.8 g, 30 mmol), the compound of Formula G-2 (5.2 g, 30 mmol), potassium phosphate (70 g, 33 mmol), tetrakis(triphenylphosphine) palladium (1.7 g, 1.5 mmol), water (50 mL), and 1,4-dioxane (300 mL) were added, reacted at 120° C. for 8 hrs, and then cooled to room temperature. The reaction solution was extracted with chloroform, and then the solvent was removed by rotary evaporation. The residue was purified by column chromatography on silica gel, to obtain the intermediate 4-4 as a solid (11.1 g, yield 77%).

(4) Synthesis of 9,10-dihydro-acridine derivative C-89

Under nitrogen atmosphere, the intermediate 4-4 (9.5 g, 20 mmol), palladium diacetate (0.13 g, 0.6 mmol), tri-tert-butylphosphine (0.45 g, 2.2 mmol), the compound of Formula E-13 (7.1 g, 22 mmol), sodium-t-butoxide (5.7 g), and toluene (300 mL) were added, reacted at 110° C. for 12 hrs, and then cooled to room temperature. The reaction solution was extracted with chloroform, and then the solvent was removed by rotary evaporation. The residue was purified by column chromatography on silica gel, to obtain the compound C-89 as a solid (12.5 g, yield 87%).

Element analysis: (C53H36N2O) calculated: C, 88.80; H, 5.06; N, 3.91; O, 2.23; found: C, 88.77; H, 5.09; N, 3.87; O, 2.24; HRMS (ESI) m/z (M+): calculated: 716.2828; found: 716.2831.

Example 74

Figure 2:
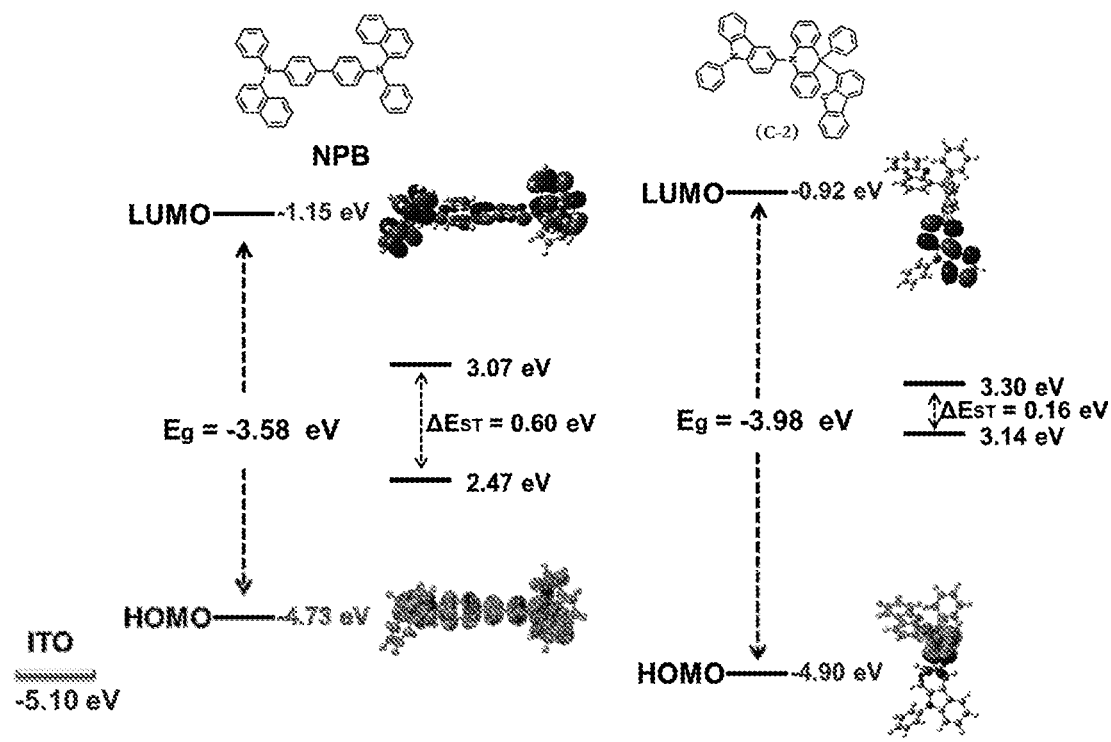
FIG. 2 compares the theoretical calculation results of the HOMO levels, the LUMO levels, and the single-triplet potential difference ΔEst of the compound of Formula C-2 provided in Example 2 of the present invention and the compound NPB provided in Comparative Example 1.
Figure 3:
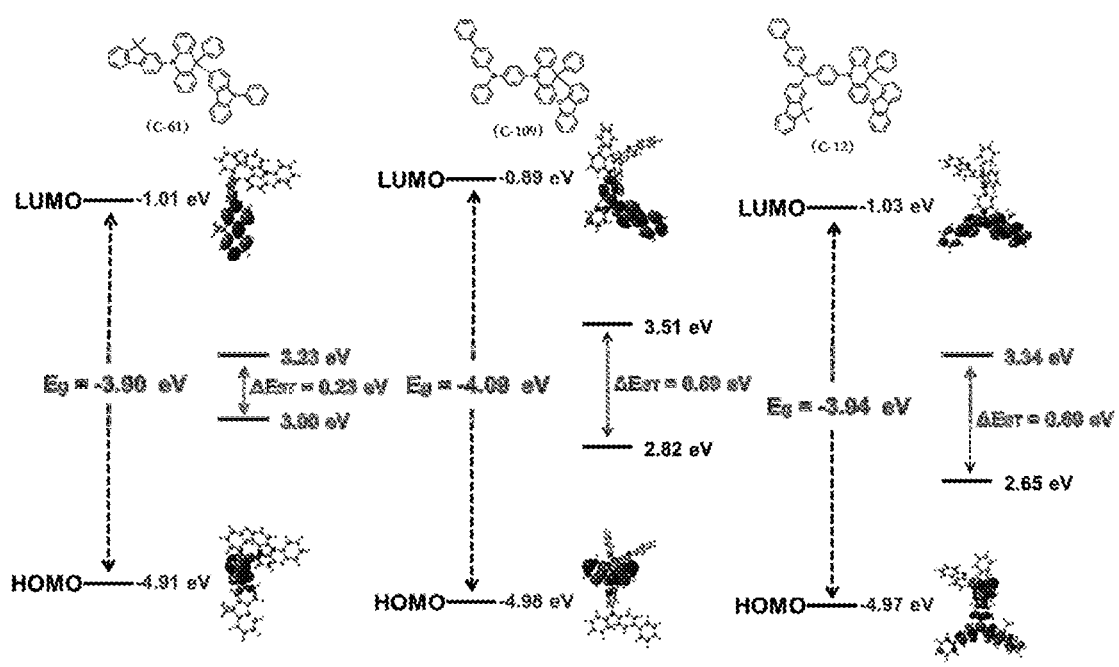
FIG. 3 compares the theoretical calculation results of the HOMO levels, the LUMO levels, and the single-triplet potential difference ΔEst of the compounds C-61, C-109 and C-12 provided in the present invention.

This example provides an organic light-emitting device, which includes, from bottom to top, an anode 1, a hole injection layer 1, a hole transport layer 3, a light emitting layer 4, an electron transport layer 5, an electron injection layer 6 and a cathode 7 stacked in sequence. As shown in FIG. 2.

In the organic light-emitting device, the material of the anode is ITO; and the material of the cathode 7 is the metal Al.

The material of the hole injection layer 2 is HAT(CN)6, having a chemical structure as shown below:

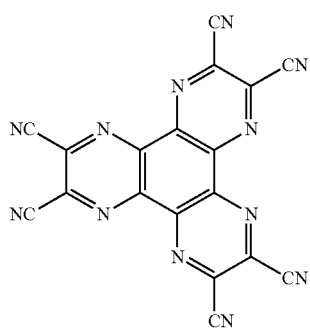

HAT(CN)6

The material of the hole injection layer 2 is the 9,10-dihydro-acridine derivative of Formula C-2:

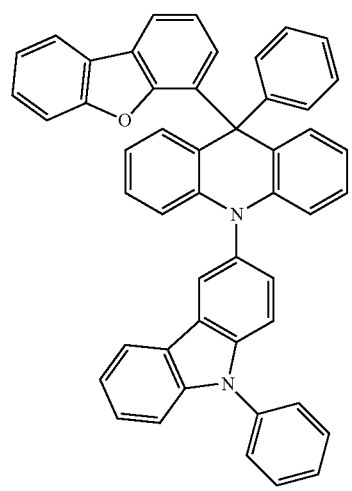

(C-2)

The light emitting layer 4 is formed by blending the host material RH and the guest material RD, where the weight ratio of the host material RH and the guest material RD blended is 100:5:

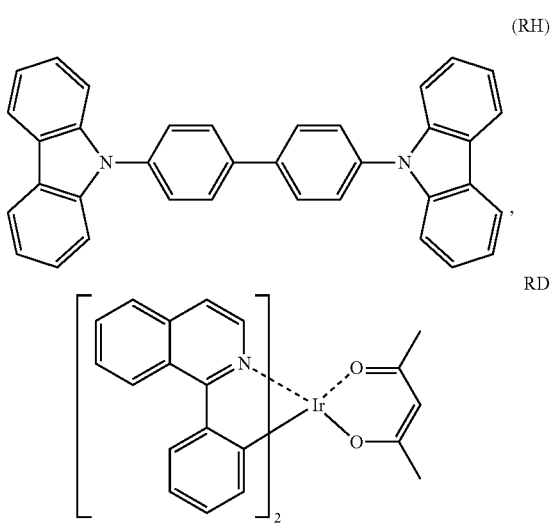

(RH)

RD

The material of the electron transport layer 5 is a compound having a structure below:

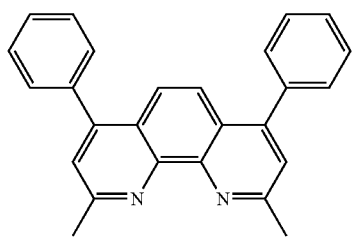

The material of the electron injection layer 6 is formed by a compound having a structure below, blended with the electron injection material LiF:

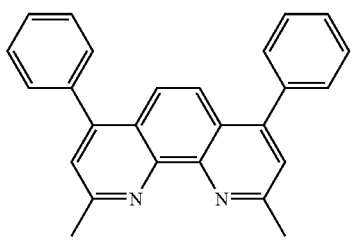 [SMILES: Cc1cc(-c2ccccc2)c2ccc3c(-c4ccccc4)cc(C)nc3c2n1]

The organic light-emitting device is configured to have a particular structure of ITO/hole injection layer (HIL)/hole transport layer (HTL, the compound of Formula C-2)/ organic light emitting layer (in which the weight ratio of RH:RD is 100:5)/electron transport layer (ETL)/electron injection layer (EIL/LiF)/cathode (Al).

In the organic light-emitting device, since the material of the hole transport layer is the 9,10-dihydro-acridine derivative of Formula C-2, the energy level of the 9,10-dihydro-acridine derivative of Formula C-2 is compared with that of NPB, as shown in FIG. 2.

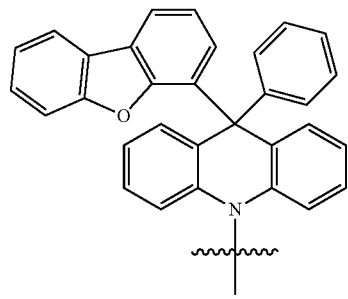 [SMILES: *N1c2ccccc2C(c2ccccc2)(c2cccc3c2oc2ccccc23)c2ccccc21]

in the compound of Formula C-2 is a group having strong electron donating performance, and the nitrogen atom in the dihydro-acridinyl group forms an aminium radical under the action of an electric field, thus creating a good hole mobility, and ensuring the effective transport of holes in the transport layer. Moreover, in the compound of Formula C-2, a carbazolyl group substituted with phenyl is introduced at the position of Ar$_2$, so the hole transport performance is further improved by taking advantage of the electron donating performance of the carbazolyl group. The 9,10-dihydro-acridine derivative of Formula C-2, has suitable HOMO level, and can reduce the potential barrier needed to overcome when holes are injected from the anode to the light emitting layer and thus increase the effective injection of holes, thereby reducing the operating voltage of the device and improving the luminescence efficiency of the device.

In the structure of Formula C-2, the dihydro-acridinyl group having a high triplet energy level is linked to a dibenzofuryl group via a σ bond, such that the structure of Formula C-2 has improved triplet energy level. The introduction of modifying groups via a σ bond allows the adjustment of the triplet energy level ($T_1$) of the 9,10-dihydro-acridine derivative of Formula C-2. The high triplet energy level of the 9,10-dihydro-acridine derivative of Formula C-2 facilitates the confining of excitons formed by recombination of electrons and holes in a light emitting region of the light emitting layer of an OLED device, so as to avoid the returning of energy from the light emitting layer to the adjacent hole transport layer. Furthermore, the 9,10-dihydro-acridine derivative of such a connection mode has an elevated LUMO level, which increases the blocking effect for electrons, and makes the electrons retained in the light emitting layer effectively, thereby increasing the probability of recombination of electrons and holes, and improving the luminescence efficiency of the device.

The 9,10-dihydro-acridine derivative of Formula C-2 has high glass transition temperature, good thermal stability and morphological stability, and excellent film-forming performance, and is not amenable to crystallization during the film formation process or during the operation of the OLED device due to heat generation after film formation, thus improving the performance and service life of the device.

In an alternative embodiment, the guest luminescent material in the light emitting layer may also be any 9,10-dihydro-acridine derivative of Formulas (C-1) and (C-3)-(C-109).

In an alternative embodiment, the guest luminescent material in the light emitting layer may also be any other compounds having a chemical structure of general Formula (I).

Example 75

This example provides an organic light-emitting device, which is different from the organic light-emitting device provided in Example 74 in that the material of the hole transport layer is a 9,10-dihydro-acridine derivative having a structure below:

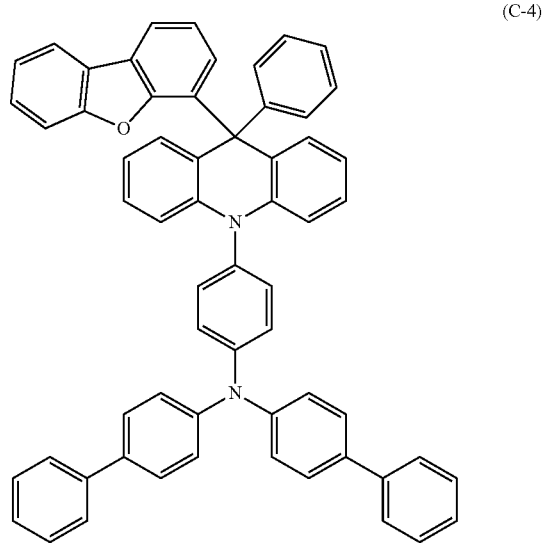 [SMILES: c1ccc(-c2ccc(N(c3ccc(-c4ccccc4)cc3)c3ccc(N4c5ccccc5C(c5ccccc5)(c5cccc6c5oc5ccccc56)c5ccccc54)cc3)cc2)cc1]

(C-4)

Example 76

This example provides an organic light-emitting device, which is different from the organic light-emitting device provided in Example 74 in that the material of the hole transport layer is a 9,10-dihydro-acridine derivative having a structure below:

(C-8)

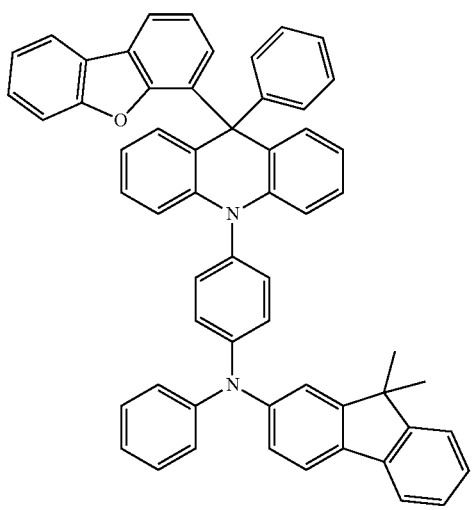

Example 77

This example provides an organic light-emitting device, which is different from the organic light-emitting device provided in Example 74 in that the material of the hole transport layer is a 9,10-dihydro-acridine derivative having a structure below:

(C-12)

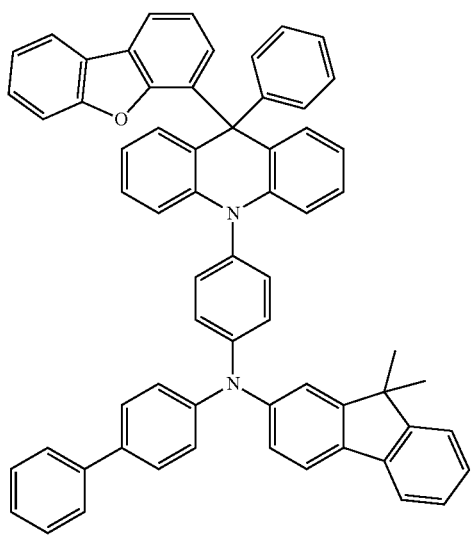

Example 78

This example provides an organic light-emitting device, which is different from the organic light-emitting device provided in Example 74 in that the material of the hole transport layer is a 9,10-dihydro-acridine derivative having a structure below:

(C-16)

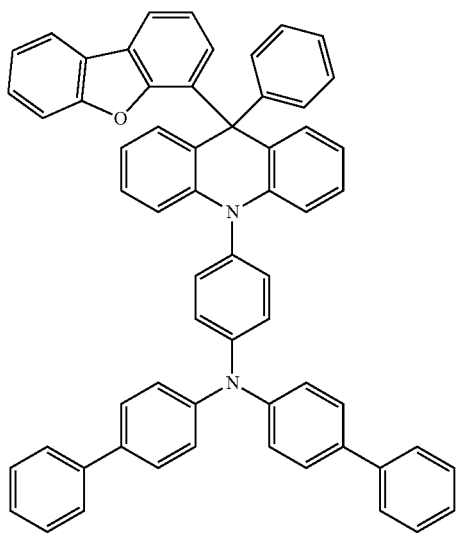

Example 79

This example provides an organic light-emitting device, which is different from the organic light-emitting device provided in Example 74 in that the material of the hole transport layer is a 9,10-dihydro-acridine derivative having a structure below:

(C-56)

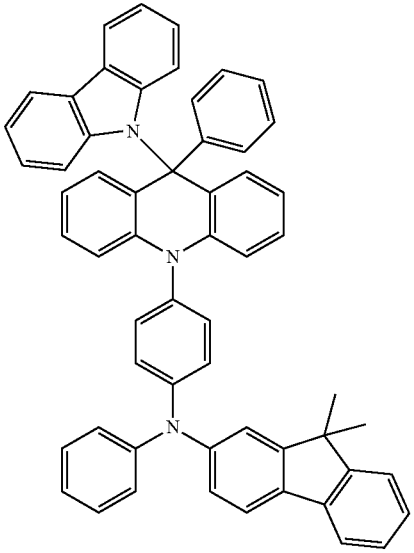

Example 80

This example provides an organic light-emitting device, which is different from the organic light-emitting device provided in Example 74 in that the material of the hole transport layer is a 9,10-dihydro-acridine derivative having a structure below:

(C-61)

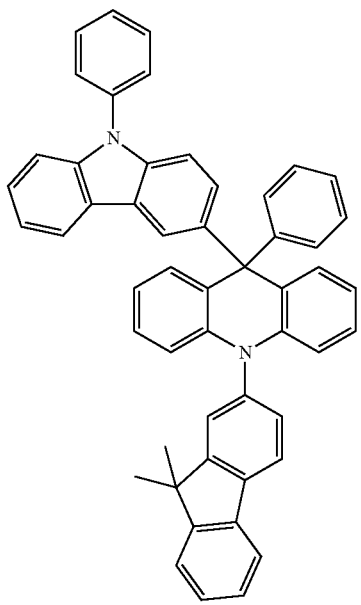

Example 81

This example provides an organic light-emitting device, which is different from the organic light-emitting device provided in Example 74 in that the material of the hole transport layer is a 9,10-dihydro-acridine derivative having a structure below:

(C-68)

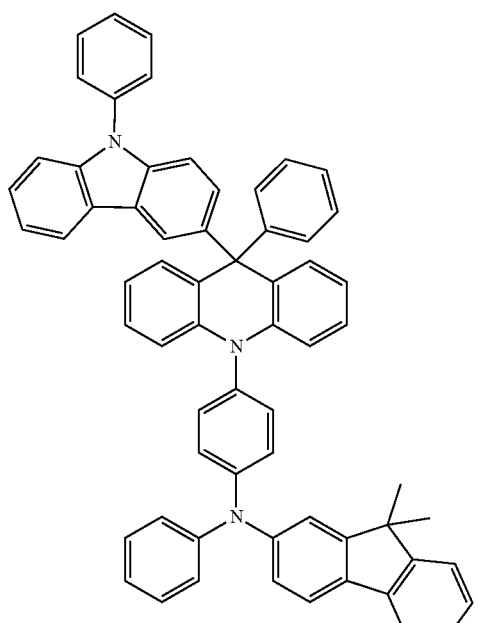

Example 82

This example provides an organic light-emitting device, which is different from the organic light-emitting device provided in Example 74 in that the material of the hole transport layer is a 9,10-dihydro-acridine derivative having a structure below:

(C-95)

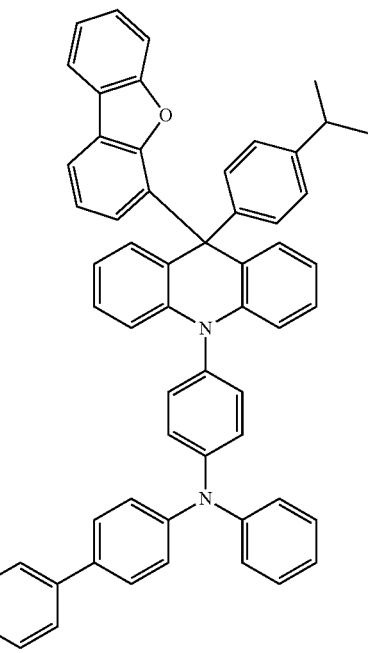

Example 83

This example provides an organic light-emitting device, which is different from the organic light-emitting device provided in Example 74 in that the material of the hole transport layer is a 9,10-dihydro-acridine derivative having a structure below:

(C-97)

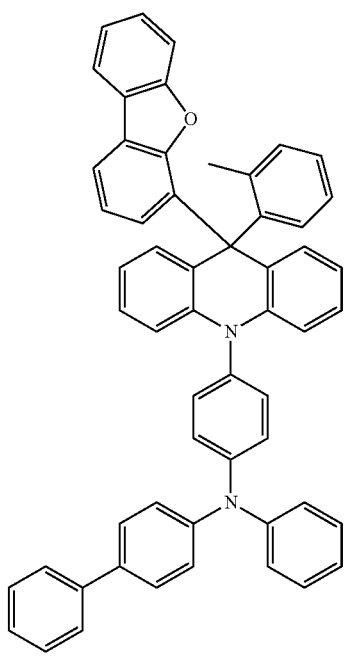

Comparative Example 1

This comparative example provides an organic light-emitting device, which is different from the organic light-emitting device provided in Example 74 in that the material of the hole transport layer is the compound NPB:

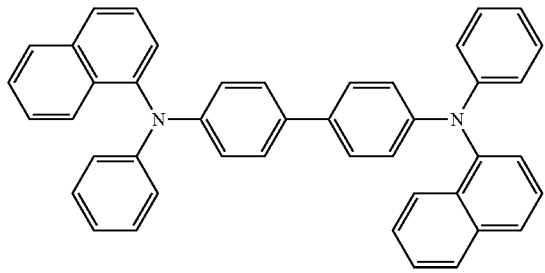 [SMILES: c1ccc(N(c2ccc(-c3ccc(N(c4ccccc4)c4cccc5ccccc45)cc3)cc2)c2cccc3ccccc23)cc1]

Test Example 1

1. Determination of Glass Transition Temperature

The glass transition temperature of the material according to the present invention was tested by differential scanning calorimetery (DSC) in a range from room temperature to 400° C. at a ramping rate of 10° C./min under nitrogen atmosphere.

2. The fluorescence and phosphorescence spectra of a solution of the 9,10-dihydro-acridine derivative in toluene (having a concentration of $10^{-5}$ mol/L) were measured at 298 K and 77 K, respectively, the corresponding triplet energy level ($T_1$) was calculated according to the formula $E=1240/\lambda$.

3. The HOMO level of the material according to the present invention was tested by cyclic voltammetry (CV) using an electrochemical workstation with platinum (Pt) as a counter electrode and silver/silver chloride (Ag/AgCl) as a reference electrode. Under a nitrogen atmosphere, the test was carried out at a scan rate of 100 mV/s in an electrolyte solution containing 0.1 M tetrabutylammonium hexafluorophosphate in dichloromethane, and the potential was calibrated by ferrocene, in which the potential of ferrocene was set to an absolute energy level under vacuum of −4.8 eV:

$$HOMO = -[E_{onset}^{ox} - E_{Fc/Fc+} + 4.8]\ eV$$

4. The LUMO level of the material molecule is calculated using the bandgap and HOMO of the material:
   $HOMO=[LUMO-E_g^{opt}]eV$ where the bandgap $$E_g^{opt} = \frac{1240}{\lambda_{onset}} eV$$

is the initial spectral absorption of the material.

TABLE 1

| 9,10-dihydro-acridine derivative | C-2 | C-4 | C-8 | C-12 | C-16 | C-56 | C-61 | C-68 | C-95 | C-97 |
|---|---|---|---|---|---|---|---|---|---|---|
| Glass Transition Temperature (° C.) | 167 | 165 | 171 | 175 | 167 | 173 | 168 | 181 | 167 | 170 |
| HOMO (eV) | −5.30 | −5.38 | −5.35 | −5.36 | −5.40 | −5.37 | −5.31 | −5.38 | −5.40 | −5.37 |
| LUMO (eV) | −2.21 | 2.19 | 2.32 | 2.33 | 2.21 | 2.17 | 2.20 | 2.37 | 2.20 | 2.19 |
| $T_1$ (eV) | 3.21 | 2.87 | 2.72 | 2.71 | 2.82 | 3.32 | 3.14 | 2.67 | 2.93 | 2.92 |

Test Example 2

The current, voltage, brightness, and luminescence spectrum of the device were tested synchronously using PR 650 scanning spectroradiometer and Keithley K 2400 digital source meter. The organic light-emitting devices provided in Examples 67-77 and the comparative example were tested. The results are shown in Table 2.

TABLE 2

| | Material of hole transport layer | Voltage/V | Current density/mA/cm² | Current efficiency cd/A | Chromaticity (CIE-X, Y) |
|---|---|---|---|---|---|
| Comparative Example 1 | NPB | 5.1 | 10 | 21 | (0.66, 0.33) |
| Example 74 | Compound of C-2 | 4.8 | 10 | 23 | (0.66, 0.33) |
| Example 75 | Compound of C-4 | 4.7 | 10 | 26 | (0.66, 0.33) |
| Example 76 | Compound of C-8 | 4.6 | 10 | 25 | (0.66, 0.33) |
| Example 77 | Compound of C-12 | 4.6 | 10 | 26 | (0.66, 0.33) |
| Example 78 | Compound of C-16 | 4.7 | 10 | 25 | (0.66, 0.33) |
| Example 79 | Compound of C-56 | 4.8 | 10 | 25 | (0.66, 0.33) |
| Example 80 | Compound of C-61 | 4.9 | 10 | 24 | (0.66, 0.33) |
| Example 81 | Compound of C-68 | 4.2 | 10 | 27 | (0.66, 0.33) |
| Example 82 | Compound of C-95 | 4.6 | 10 | 26 | (0.66, 0.33) |
| Example 83 | Compound of C-97 | 4.5 | 10 | 25 | (0.66, 0.33) |

The organic light-emitting devices provided in Examples 74-83 and Comparative Example 1 were tested. The results are shown in Table 2. Compared with the device provided in Comparative Example 1, the OLED devices provided in Examples 74-83 has lowered operating voltage and increased current efficiency, indicating that the 9,10-dihydro-acridine derivative provided in the present invention, when used as a hole transport material in an OLED device, can greatly improve the luminescence efficiency, reduce the driving voltage, and increase the performance of the OLED device.

Apparently, the above-described embodiments are merely examples provided for clarity of description, and are not intended to limit the implementations of the present invention. Other variations or changes can be made by those skilled in the art based on the above description. The embodiments are not exhaustive herein. Obvious variations or changes derived therefrom also fall within the protection scope of the present invention.

What is claimed is:

1. A 9,10-dihydro-acridine derivative, having a structure of Formula (I):

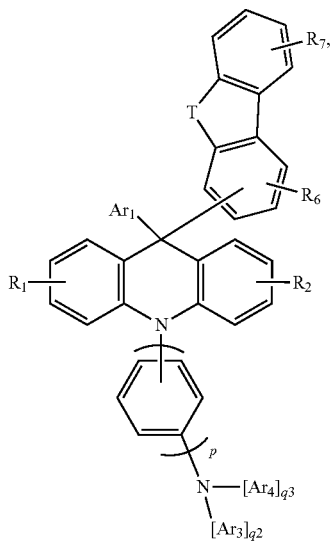

wherein T is selected from O, S, C($R_3$)($R_4$) or N($R_5$);
$R_1$-$R_4$ and $R_6$-$R_7$ are each independently selected from hydrogen;
$R_5$ is a $C_6$-$C_{60}$ substituted or unsubstituted aryl group;
$Ar_1$ is a $C_6$-$C_{60}$ substituted or unsubstituted aryl group;
p is an integer from 1 to 5, $q_2$ is an integer from 1 to 4, and $q_3$ is an integer from 1 to 4;
$Ar_3$ and $Ar_4$ are each independently selected from the following groups that are unsubstituted or substituted with 1-4 $R_{1a}$:
phenyl, biphenylyl, terphenylyl, fluorenyl;
in which $R_{1a}$ is a $C_1$-$C_6$ alkyl group.

2. The 9,10-dihydro-acridine derivative according to claim 1, wherein $Ar_1$ is selected from any of the following groups:
phenyl, biphenylyl, terphenylyl, indenyl, fluorenyl, naphthyl, azulenyl, pentalenyl, heptalenyl, octalenyl, benzodiindenyl, acenaphthylenyl, phenalenyl, phenanthrenyl, anthracenyl, triindenyl, fluoranthenyl, acephenanthrenyl, aceanthrylenyl, 9,10-benzophenanthrenyl, pyrenyl, 1,2-benzophenanthrenyl, butylphenyl, naphthacenyl, pleiadenyl, picenyl, perylenyl, pentaphenyl, pentacenyl, tetraphenylene, cholanthrenyl, helicenyl, hexaphenyl, rubicenyl, coronenyl, trinaphthylenyl, heptaphenyl, pyranthrenyl, ovalenyl, corannulenyl, anthanthrenyl, truxenyl.

3. The 9,10-dihydro-acridine derivative according to claim 1, wherein $R_5$ are each independently selected from phenyl, biphenylyl, naphthyl, anthracenyl, phenanthrenyl, fluorenyl, pyrenyl, perylenyl, corranulenyl, triphenylene, fluoranthenyl.

4. The 9,10-dihydro-acridine derivative according to claim 2, wherein $R_5$ are each independently selected from biphenylyl, naphthyl, anthracenyl, phenanthrenyl, fluorenyl, pyrenyl, perylenyl, corranulenyl, triphenylene, or fluoranthenyl.

5. The 9,10-dihydro-acridine derivative according to claim 1, having any of the following molecular structures:

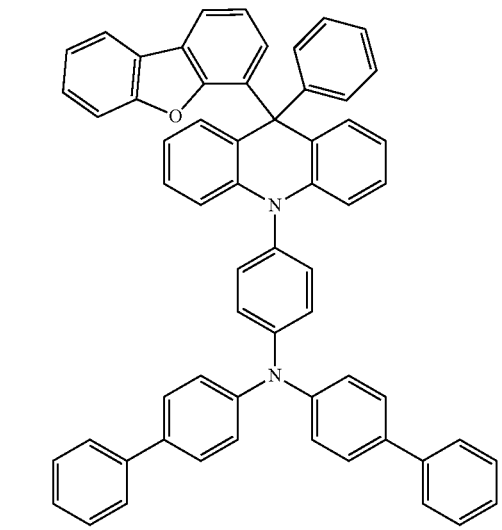

(C-4)

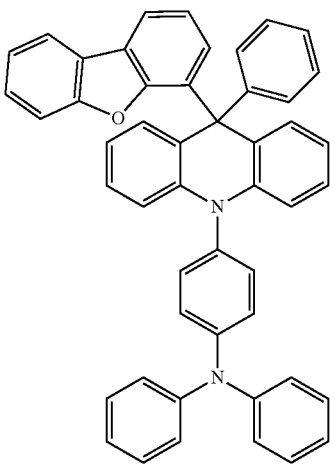

(C-5)

(C-8)
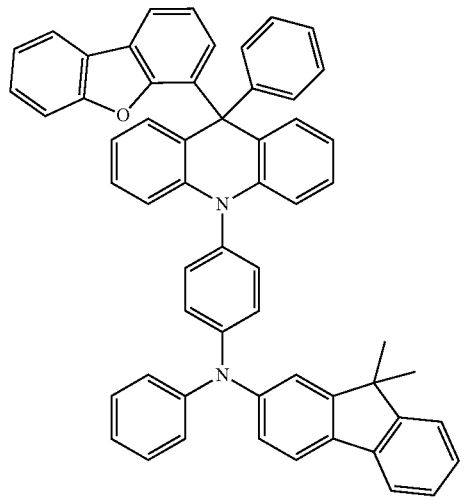
(C-9)
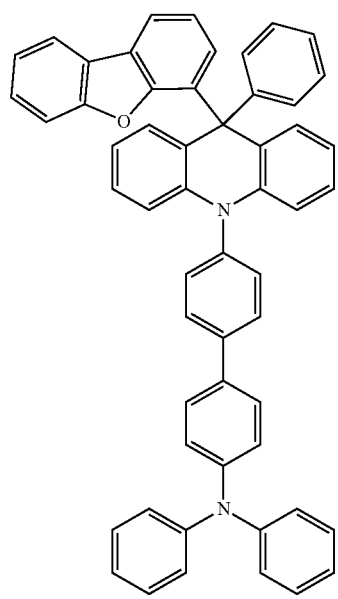
(C-12)
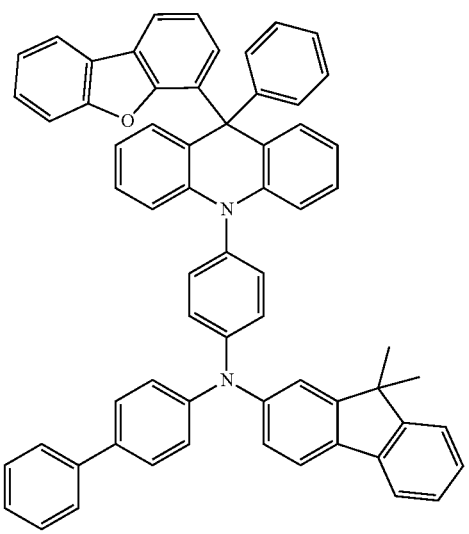
(C-16)
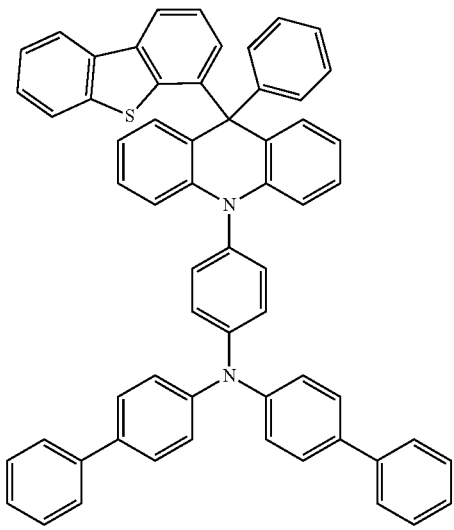
(C-17)
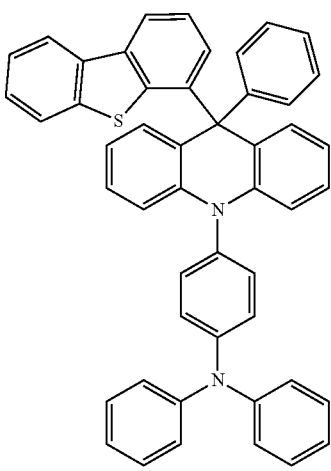
(C-20)
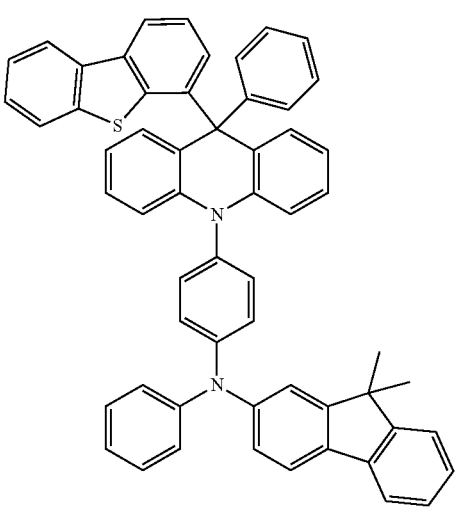

(C-21)
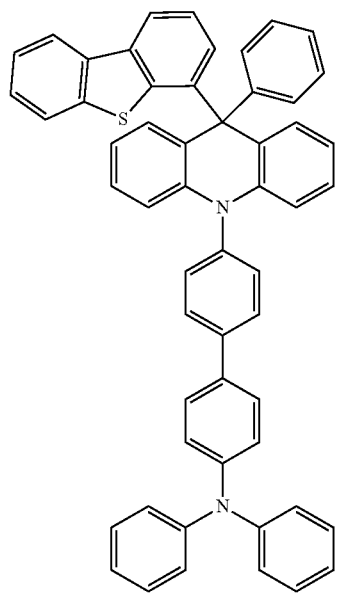
(C-64)
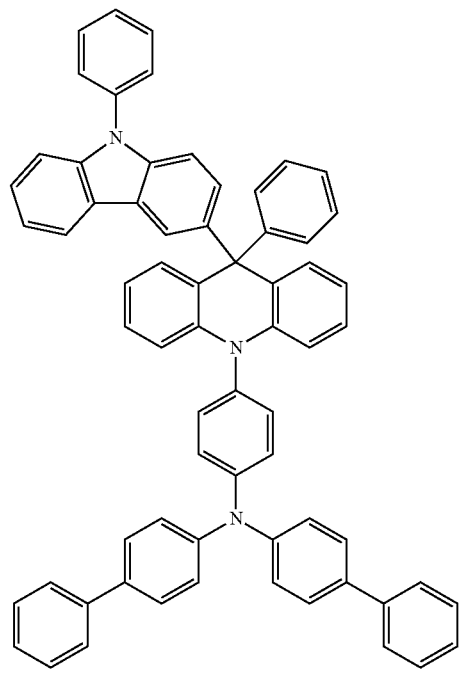
(C-24)
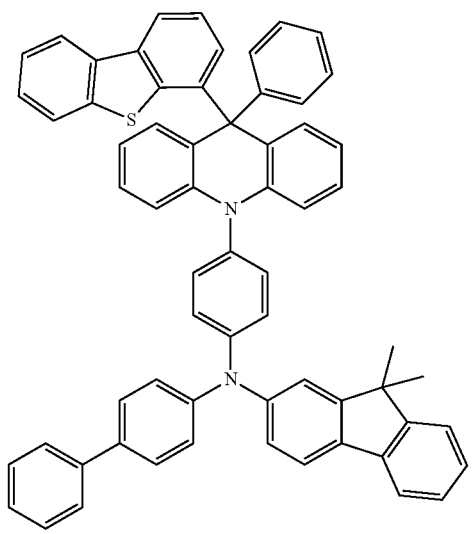
(C-65)
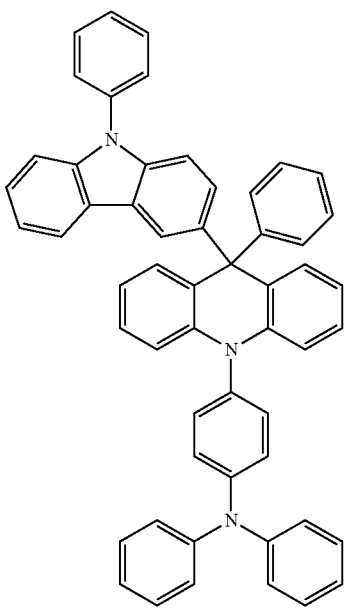

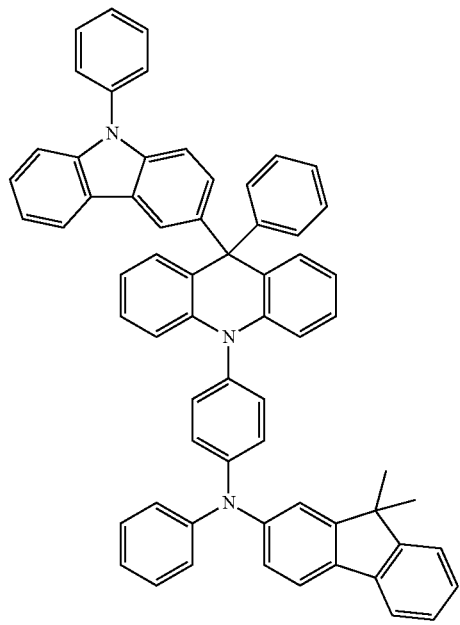
(C-68)
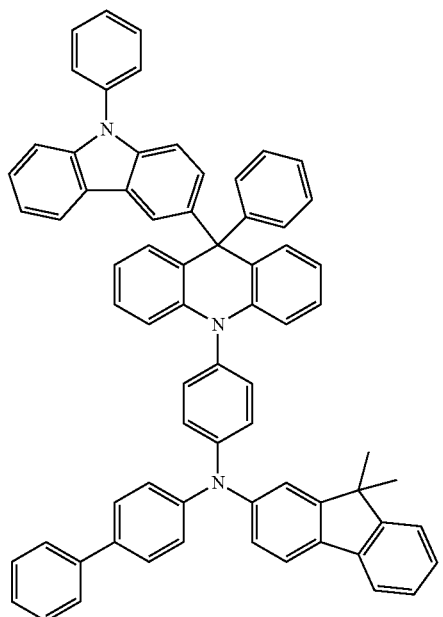
(C-72)
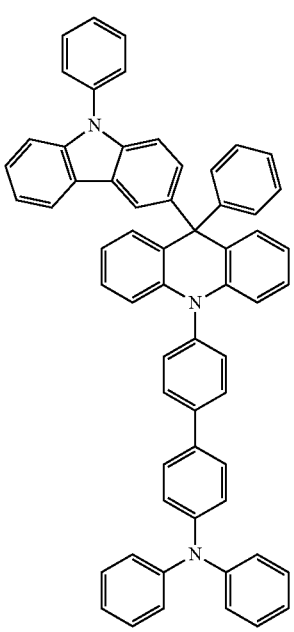
(C-69)
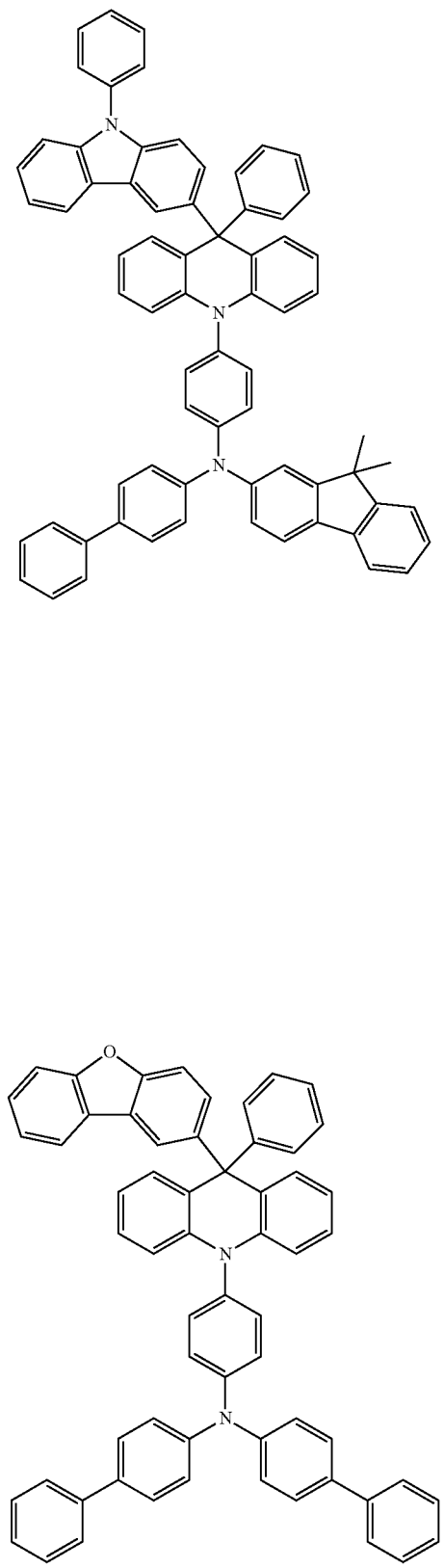
(C-73)

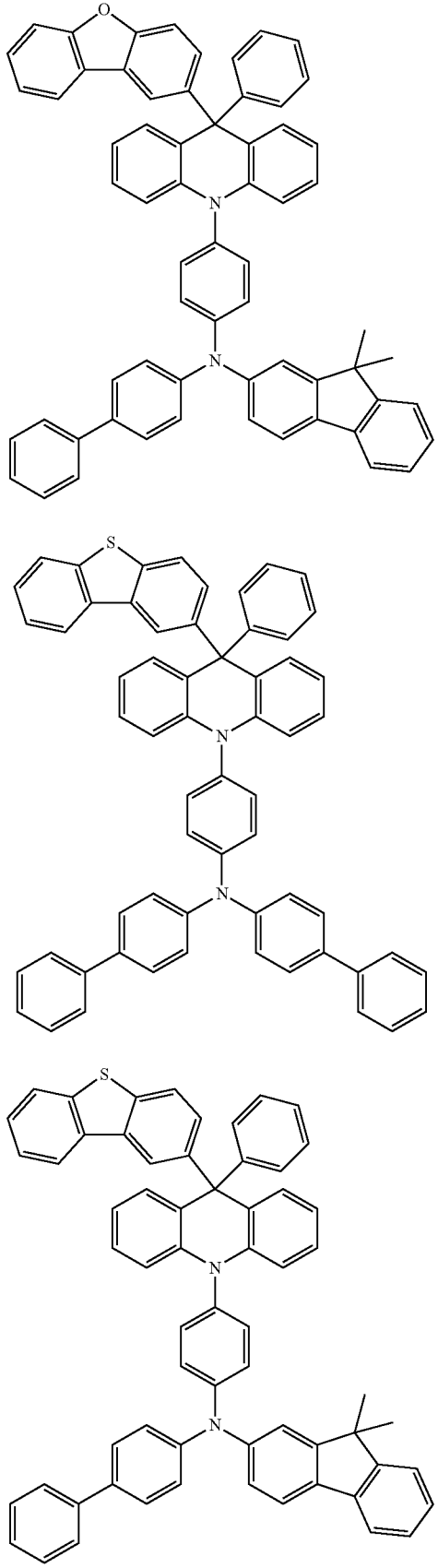

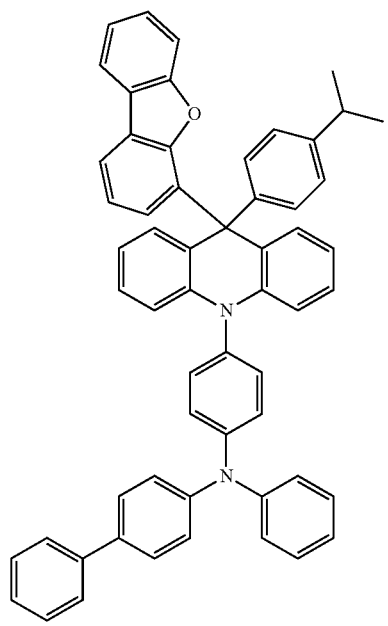
(C-95)
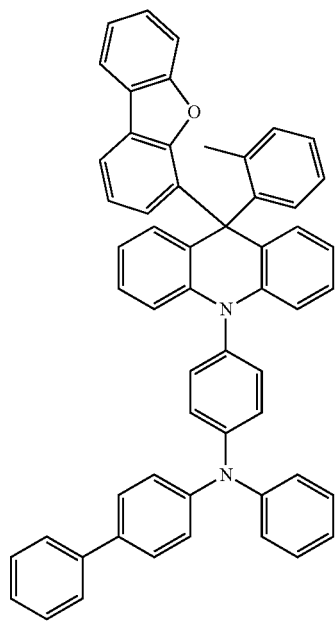
(C-97)
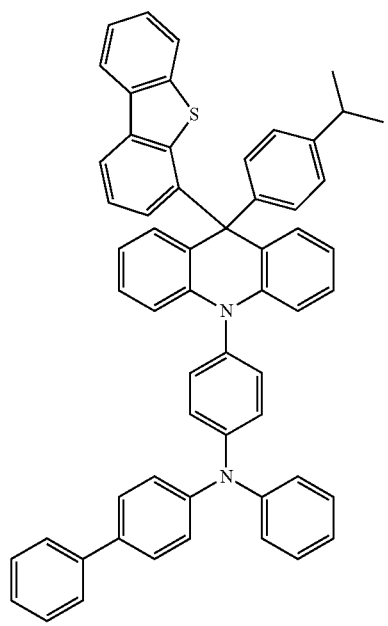
(C-96)
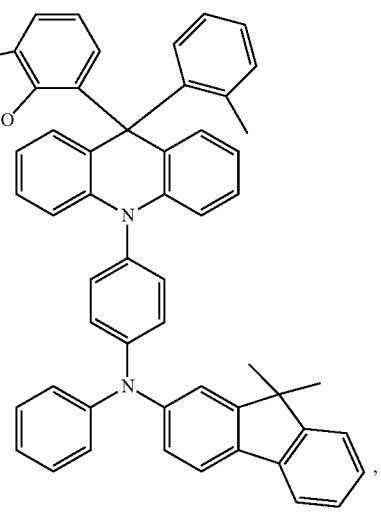
(C-99)
, and (C-109)

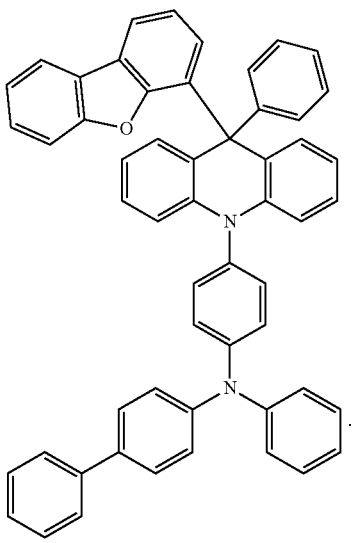

6. The 9,10-dihydro-acridine derivative according to claim 1, wherein the 9,10-dihydro-acridine derivative is a hole transport material.

7. A method for preparing the 9,10-dihydro-acridine derivative according to claim 1, wherein the compound of Formula (I) is synthesized through the following steps:

subjecting a compound of Formula (A) and a compound of Formula (B) as starting materials to a nucleophilic addition reaction, to obtain an intermediate 1; subjecting the intermediate 1 and a compound of Formula (D) to a dehydration-condensation reaction in the presence of Eaton's Reagent, to obtain an intermediate 2; and subjecting the intermediate 2 and a compound of Formula (E) to a coupling reaction in the presence of a catalyst, to obtain the compound of Formula (I);

where the synthesis route for the compound of Formula (I) is shown below:

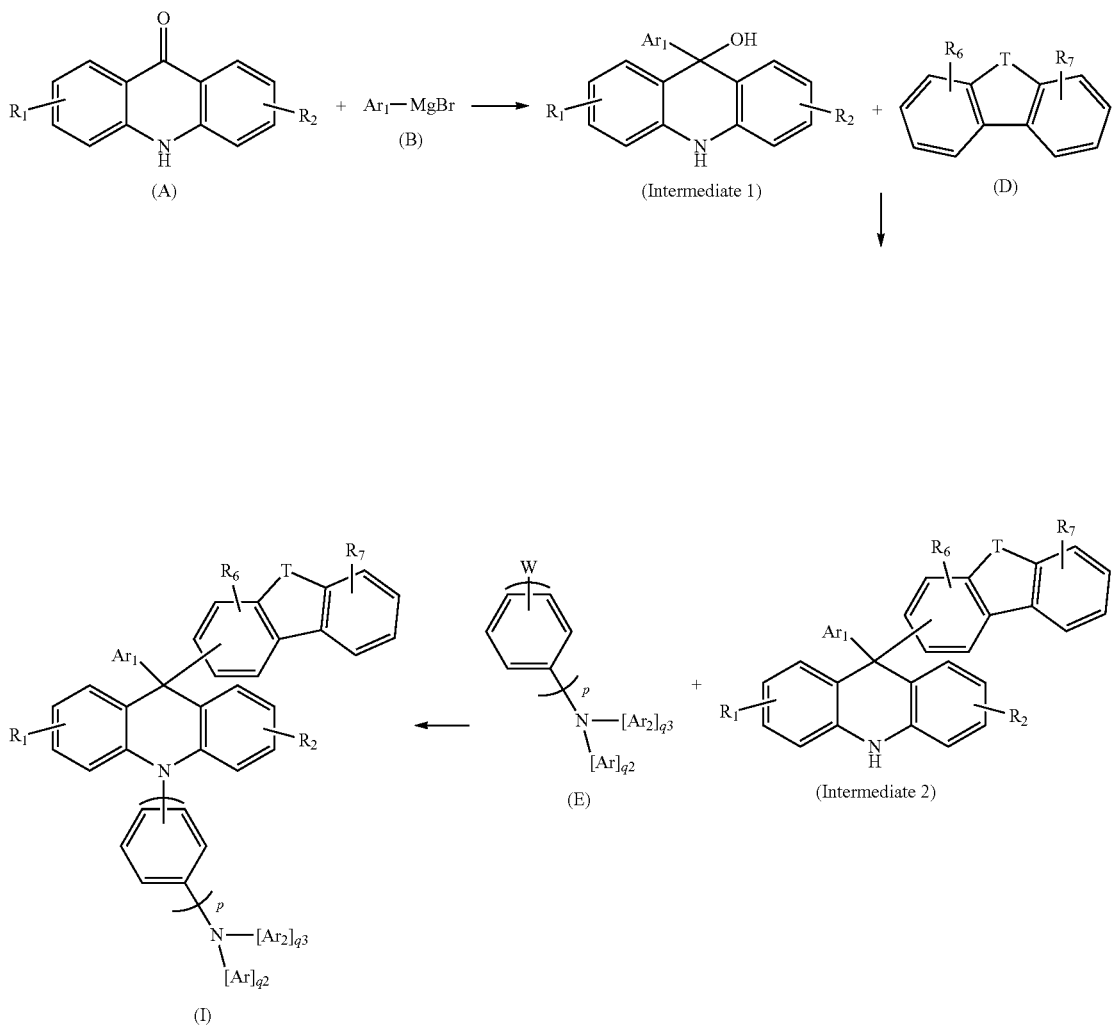

or subjecting the compound of Formula (A) and the compound of Formula (F) as starting materials to a nucleophilic addition reaction, to obtain an intermediate 3; subjecting the intermediate 3 to a nucleophilic substitution reaction, to obtain an intermediate 3'; subjecting the intermediate 3' and a compound of Formula (G) to a Suzuki reaction, to obtain an intermediate 4; and subjecting the intermediate 4 and the compound of Formula (E) to a coupling reaction in the presence of a catalyst, to obtain the compound of Formula (I);

where the synthesis route for the compound of Formula (I) is shown below:

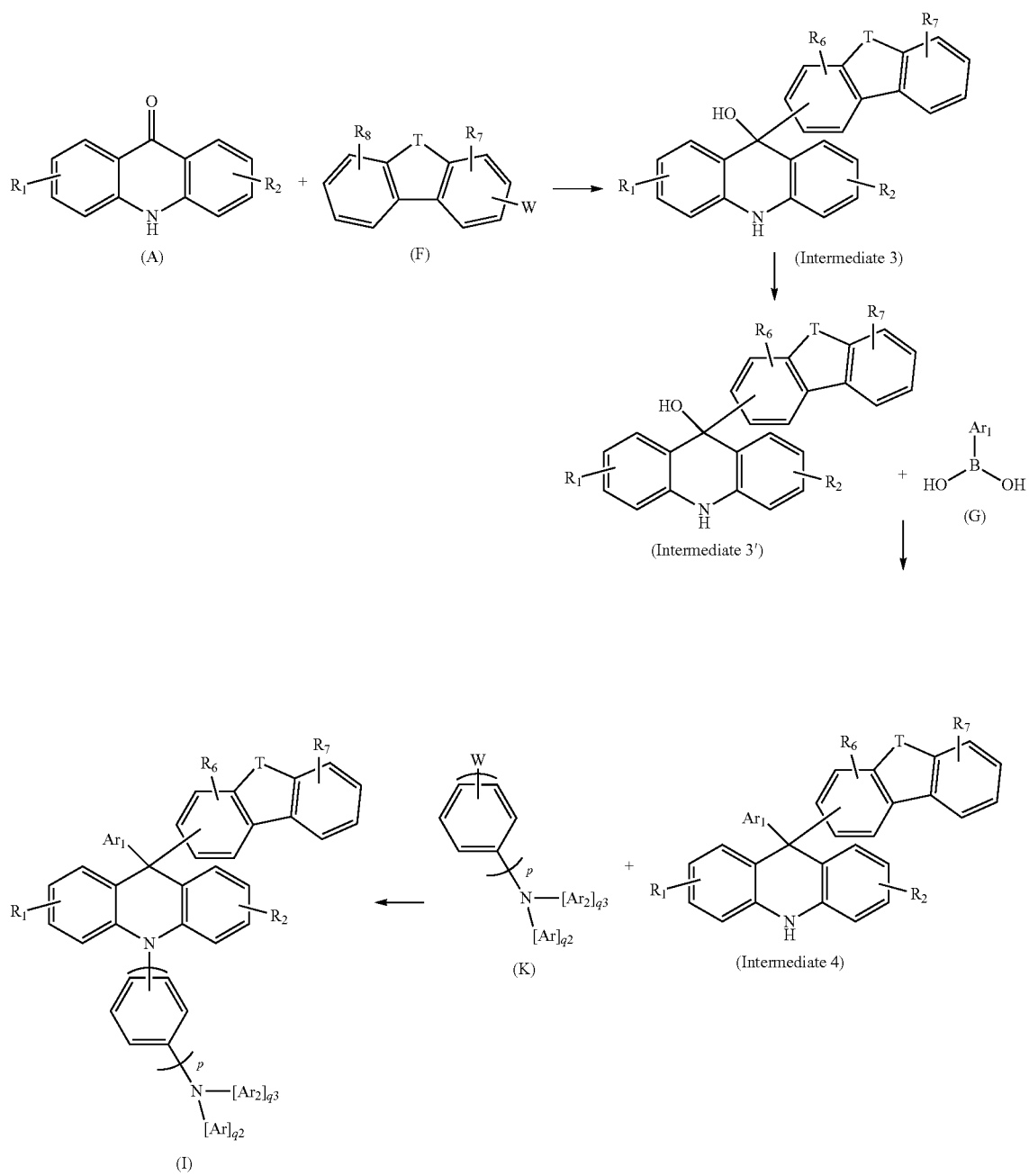

in which W is selected from hydrogen, fluoro, chloro, bromo or iodo, and -OTf is triflate.

8. An organic light-emitting device, having at least one functional layer containing a 9,10-dihydro-acridine derivative, having a structure of Formula (I):

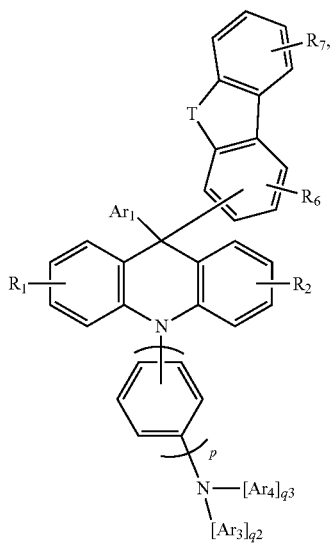

wherein T is selected from O, S, $C(R_3)(R_4)$ or $N(R_5)$;

$R_1$-$R_4$ and $R_6$-$R_7$ are each independently selected from hydrogen;

$R_5$ is a $C_6$-$C_{60}$ substituted or unsubstituted aryl group;

$Ar_1$ is a $C_6$-$C_{60}$ substituted or unsubstituted aryl group;

p is an integer from 1 to 5, $q_2$ is an integer from 1 to 4, and $q_3$ is an integer from 1 to 4;

$Ar_3$ and $Ar_4$ are each independently selected from the following groups that are unsubstituted or substituted with 1-4 $R_{1a}$:

phenyl, biphenylyl, terphenylyl, fluorenyl;

in which $R_{1a}$ is a $C_1$-$C_6$ alkyl group.

9. The organic light-emitting device according to claim 8, wherein the functional layer is a hole transport layer and/or an electron blocking layer.

10. The organic light-emitting device according to claim 8, wherein the functional layer is a light emitting layer.

* * * * *